United States Patent
Jin et al.

(10) Patent No.: US 11,969,123 B2
(45) Date of Patent: *Apr. 30, 2024

(54) DEVICES, COMPOSITIONS, AND METHODS FOR USE IN SURFACE DECONTAMINATION

(71) Applicant: Kinnos Inc., Brooklyn, NY (US)

(72) Inventors: Katherine Jin, Brooklyn, NY (US); Kevin Tyan, Brooklyn, NY (US); Jason Kang, Brooklyn, NY (US); Sarah-Marie Saatori, Brooklyn, NY (US); Aaron Chong, Brooklyn, NY (US); Joseph W. Pruitt, Brooklyn, NY (US); Donald A. Muntner, Brooklyn, NY (US); Noah McNeely, Brooklyn, NY (US); David R. Schiff, Brooklyn, NY (US); Jeremy M. Ridley, Brooklyn, NY (US); Reile M. Slattery, Brooklyn, NY (US); Tarun Srinivasan, Brooklyn, NY (US); Yuvprakash Singh, Brooklyn, NY (US)

(73) Assignee: Kinnos Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/962,526

(22) Filed: Oct. 9, 2022

(65) Prior Publication Data

US 2023/0109612 A1    Apr. 6, 2023

Related U.S. Application Data

(63) Continuation of application No. 17/257,997, filed as application No. PCT/US2019/041604 on Jul. 12, 2019, now Pat. No. 11,464,371.

(Continued)

(51) Int. Cl.
*A47K 10/42* (2006.01)
*A61L 2/18* (2006.01)
*A47K 10/32* (2006.01)

(52) U.S. Cl.
CPC .............. *A47K 10/421* (2013.01); *A61L 2/18* (2013.01); *A47K 2010/3233* (2013.01);
(Continued)

(58) Field of Classification Search
CPC ............................................. A47K 2010/3266
(Continued)

(56) References Cited

U.S. PATENT DOCUMENTS 2,058,489 A   10/1936  Murch et al.
3,609,075 A    9/1971  Barbera
(Continued)

FOREIGN PATENT DOCUMENTS

CA   2320536 A1   3/2001
CA   2665432 A1   5/2008
(Continued)

OTHER PUBLICATIONS

Extended European Search Report dated Aug. 1, 2019 for European Application No. 17750892.6 filed on Feb. 10, 2017. 10 pages.
(Continued)

*Primary Examiner* — Gene O Crawford
*Assistant Examiner* — Ayodeji T Ojofeitimi
(74) *Attorney, Agent, or Firm* — Elmore Patent Law Group; Joseph C. Zucchero

(57) ABSTRACT

Provided are devices, compositions, and methods for surface disinfection and decontamination; the devices generally adapted to contain a single or multi-component indicator composition, and optionally a disinfectant composition, and to dispense the indicator composition and optional disinfectant composition to a disinfectant solution, a surface, or a (Continued)

disinfectant article upon actuation of the device; also provided is an article of manufacture in the form of a removable cartridge adapted to fit a device described here, which may be pre-filled with a single or multi-component indicator composition as described here, and/or with a disinfectant composition, and one or more optional additives.

70 Claims, 32 Drawing Sheets

Related U.S. Application Data

(60) Provisional application No. 62/697,278, filed on Jul. 12, 2018, provisional application No. 62/799,459, filed on Jan. 31, 2019.

(52) U.S. Cl.
CPC ... *A47K 2010/3273* (2013.01); *A61L 2202/14* (2013.01); *A61L 2202/25* (2013.01)

(58) Field of Classification Search
USPC ................................................ 221/33–63
See application file for complete search history.

(56) References Cited

U.S. PATENT DOCUMENTS

| | | | |
|---|---|---|---|
| 4,071,463 A | 1/1978 | Steinhauer | |
| 4,229,410 A | 10/1980 | Kosti | |
| 4,249,274 A | 2/1981 | Kitko | |
| 4,308,625 A | 1/1982 | Kitko | |
| 4,346,120 A | 8/1982 | Morley et al. | |
| 4,353,866 A | 10/1982 | Wong | |
| 4,390,342 A | 6/1983 | Bruttel et al. | |
| 4,420,412 A | 12/1983 | Wong | |
| 4,474,677 A | 10/1984 | Foxlee | |
| 4,605,534 A | 8/1986 | Meloy | |
| 4,623,476 A | 11/1986 | Nayar et al. | |
| 4,639,326 A | 1/1987 | Czempik et al. | |
| 4,678,658 A | 7/1987 | Casey et al. | |
| 4,822,854 A | 4/1989 | Ciolino | |
| 4,898,681 A | 2/1990 | Burton | |
| 5,034,150 A | 7/1991 | Smith | |
| 5,064,635 A | 11/1991 | Casey | |
| 5,110,492 A | 5/1992 | Casey | |
| 5,257,711 A | 11/1993 | Wirtz-odenthal | |
| 5,358,653 A | 10/1994 | Gladfelter et al. | |
| 5,547,662 A | 8/1996 | Khan et al. | |
| 5,556,835 A | 9/1996 | Inaoka et al. | |
| 5,670,469 A | 9/1997 | Dingus et al. | |
| 6,213,424 B1 | 4/2001 | Helfer-Grand | |
| 6,305,576 B1 | 10/2001 | Leoncavallo | |
| 6,321,937 B1 | 11/2001 | Desimone et al. | |
| 6,362,156 B1 | 3/2002 | Hsu et al. | |
| 6,447,757 B1 | 9/2002 | Orlowski et al. | |
| 6,503,877 B2 | 1/2003 | Grande et al. | |
| 6,525,237 B1 | 2/2003 | Purdon et al. | |
| 6,677,287 B1 | 1/2004 | Willman et al. | |
| 6,814,816 B2 | 11/2004 | Achar et al. | |
| 6,900,167 B2 | 5/2005 | Griese et al. | |
| 7,179,779 B1 | 2/2007 | Hauser et al. | |
| 7,271,137 B2 | 9/2007 | Tucker et al. | |
| 7,276,468 B2 | 10/2007 | Tucker | |
| 7,648,046 B2 | 1/2010 | Sosalla et al. | |
| 7,750,199 B1 | 7/2010 | Tucker | |
| 8,389,463 B2 | 3/2013 | Mohs et al. | |
| 8,600,547 B2 | 12/2013 | Petersen et al. | |
| 9,101,134 B2 | 8/2015 | Huang et al. | |
| 9,155,310 B2 | 10/2015 | Agrawal et al. | |
| 9,458,414 B2 | 10/2016 | Rieth et al. | |
| 9,717,669 B2 | 8/2017 | Cozean et al. | |
| 10,052,398 B2 | 8/2018 | Kang et al. | |
| 10,246,671 B2 | 4/2019 | Kang et al. | |
| 10,329,520 B2 | 6/2019 | Kang et al. | |
| 10,344,251 B2 | 7/2019 | Kang et al. | |
| 11,464,371 B2 * | 10/2022 | Jin | C11D 17/049 |
| 2001/0051567 A1 | 12/2001 | Schaschke | |
| 2003/0059483 A1 | 3/2003 | Sowle et al. | |
| 2003/0100101 A1 | 5/2003 | Huth et al. | |
| 2003/0168489 A1 | 9/2003 | Formon et al. | |
| 2004/0014875 A1 | 1/2004 | Russo et al. | |
| 2004/0251375 A1 | 12/2004 | Denen et al. | |
| 2005/0019090 A1 | 1/2005 | Takasu | |
| 2006/0147482 A1 | 7/2006 | Chang | |
| 2006/0222675 A1 | 10/2006 | Sabnis et al. | |
| 2008/0067470 A1 | 3/2008 | Thangaraj et al. | |
| 2008/0193650 A1 | 8/2008 | Lyon | |
| 2008/0202953 A1 | 8/2008 | Mueller et al. | |
| 2008/0227856 A1 | 9/2008 | Melker | |
| 2009/0032636 A1 | 2/2009 | Orlandi et al. | |
| 2009/0099054 A1 | 4/2009 | Smith et al. | |
| 2010/0032443 A1 * | 2/2010 | Mueller | A45D 34/04 221/34 |
| 2010/0069274 A1 | 3/2010 | Ebine et al. | |
| 2010/0134296 A1 | 6/2010 | Hwang | |
| 2011/0062178 A1 | 3/2011 | Godsell | |
| 2012/0021068 A1 | 1/2012 | Barness et al. | |
| 2012/0138625 A1 | 6/2012 | Case et al. | |
| 2013/0058867 A1 | 3/2013 | Moro et al. | |
| 2013/0071488 A1 | 3/2013 | Suekuni et al. | |
| 2013/0100101 A1 | 4/2013 | Li et al. | |
| 2014/0057987 A1 | 2/2014 | Vinson et al. | |
| 2014/0100153 A1 | 4/2014 | Martinez-Crowley et al. | |
| 2015/0044144 A1 | 2/2015 | Lin et al. | |
| 2015/0093425 A1 | 4/2015 | Moore | |
| 2015/0335598 A1 | 11/2015 | Buchalova et al. | |
| 2015/0366416 A1 | 12/2015 | Hoefte et al. | |
| 2017/0333586 A1 | 11/2017 | Kang et al. | |
| 2017/0336372 A1 | 11/2017 | Kang et al. | |
| 2017/0336373 A1 | 11/2017 | Kang et al. | |
| 2018/0010080 A1 | 1/2018 | Kang et al. | |
| 2018/0338894 A1 | 11/2018 | Nocker et al. | |
| 2019/0001010 A1 | 1/2019 | Kang et al. | |

FOREIGN PATENT DOCUMENTS

| | | |
|---|---|---|
| CA | 2865682 A1 | 3/2015 |
| CN | 1817072 A | 8/2006 |
| CN | 1817972 A | 8/2006 |
| CN | 101155539 A | 4/2008 |
| CN | 101222871 A | 7/2008 |
| CN | 102065696 A | 5/2011 |
| CN | 102450381 A | 5/2012 |
| CN | 103766402 A | 5/2014 |
| CN | 104054750 A | 9/2014 |
| CN | 105593149 A | 5/2016 |
| DE | 10318009 A1 | 11/2004 |
| EP | 0018344 A1 | 10/1980 |
| EP | 1290121 A2 | 3/2003 |
| EP | 1457529 B1 | 6/2007 |
| EP | 1846111 A2 | 10/2007 |
| EP | 1926808 A1 | 6/2008 |
| EP | 2170149 B1 | 10/2015 |
| FR | 2988731 A1 | 10/2013 |
| GB | 1032151 A | 6/1966 |
| GB | 2326340 A | 12/1998 |
| RU | 2458706 C1 | 8/2012 |
| WO | 8201319 A1 | 4/1982 |
| WO | 0078911 A1 | 12/2000 |
| WO | 0123510 A2 | 4/2001 |
| WO | 03001931 A1 | 1/2003 |
| WO | 2004091356 A2 | 10/2004 |
| WO | 2005055963 A2 | 6/2005 |
| WO | 2005065509 A1 | 7/2005 |
| WO | 2007010562 A1 | 1/2007 |
| WO | 2007063372 A2 | 6/2007 |
| WO | 2008060778 A2 | 5/2008 |
| WO | 2008147904 A2 | 12/2008 |
| WO | 2009007924 A2 | 1/2009 |
| WO | 2013134327 A1 | 9/2013 |
| WO | 2015106044 A1 | 7/2015 |

(56) References Cited

FOREIGN PATENT DOCUMENTS

| WO | 2016093882 A1 | 6/2016 |
|---|---|---|
| WO | 2017139670 A1 | 8/2017 |
| WO | 2018022621 A1 | 2/2018 |

OTHER PUBLICATIONS

International Search Report dated Sep. 10, 2015 for international Application No. PCT/US2015/032325, filed May 23, 2015.
International Preliminary Report on Patentability dated Jun. 22, 2017 for International Application PCT/US2015/032325 filed May 23, 2015.
International Search Report dated Apr. 13, 2017 for International Application No. PCT/US2017017509, filed Feb. 10, 2017.
International Search Report dated Nov. 27, 2017 for International Application No. PCT/US2017/043733, filed Jul. 25, 2017.
Transcript of "Kinnos Co-Founder Jason Kang Reveals the Story Behind a Life-Saving Product", by GoDaddy, Apr. 21, 2020.
Transcript of Kevin Tyan's TedMed Talk "What if we could highlight invisible threats for our lifesavers?" Mar. 22, 2017.
Transcript of NPR interview "Innovation in the Battle Against Ebola" aired on Nov. 3, 2014.
Transcript of PBS Newshour interview "Helping student inventors turn big ideas into the next big thing" aired on Aug. 31, 2016.
Transcript of UN Web TV interview "International Day of Women and Girls in Science", Feb. 10, 2017.
Written Opinion of the International Searching Authority dated Apr. 13, 2017 for International Application PCT/US2017/017509, filed Feb. 10, 2017. 13 pages.
Transcript of "Jason Kang: Ebola Design Challenge, Highlight Bleach Project," by Columbia Engineering, Apr. 1, 2015.
Transcript of "Celebrate Invention 2017," by AAAS-Lemelson Invention Ambassador Program,, Aug. 7, 2017.
Transcript of "TRANS Conference 2017 Press Room Interview with Katherine Jin, COO and Co-Founder of Kinnos," by H. Spectrum, Dec. 13, 2017.
Transcript of "Katherine Jin Explains the Evolution of Highlight," by Lemelson-MIT,, Jul. 13, 2016.
Transcript of "Kinnos: E-Team Program Gives you a Chance to Think About the Business," by VentureWell, Jul. 19, 2016.
Transcript of "Jason Kang, CEO of Kinnos," featured on Cheddar, Mar. 9, 2017.
Transcript of "ScIQ Interviews: Katherine Jin and Keith Comito, Challenges in American Innovation," by ScIQ, Sep. 2, 2017.
Transcript of "Kinnos Colorized Disinfectant," Disrupt SF 2017, by TechCrunch, Sep. 24, 2017.
Brickman, , "All Hands on Deck", The New Yorker, Oct. 27, 2014.
Burns, , "STEM Student Spotlight: Jason Kang", Scientific American Blog Network, Mar. 15, 2016.
Cooper, , "Blue dye could help keep Ebola doctors safe", Engadget.com article, Oct. 13, 2016.
Farmer, M. A. , "Columbia Confronts the Ebola Crisis", article published on Columbia University Fu Foundation School of Engineering and Applied Science website, Oct. 17, 2014.
Kanno-Youngs, Z. , "Student Invention Helps Safeguard Health-Care Workers Treating Ebola", Columbia students develop a powder that turns bleach blue to ensure fully sterilized suits, Wall Street Journal, (https://www.wsj.com/articles/student-invention-helps-safeguard-health-care-workers-treating-ebola-1464300345?cb=logged0.13334920427976615#)., May 26, 2016.

* cited by examiner

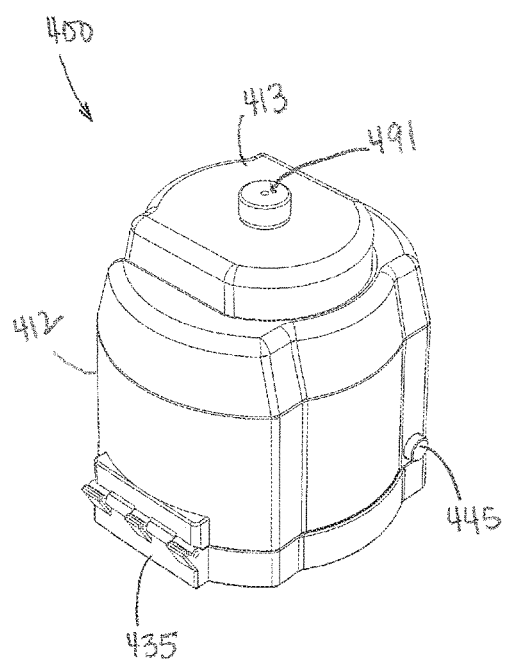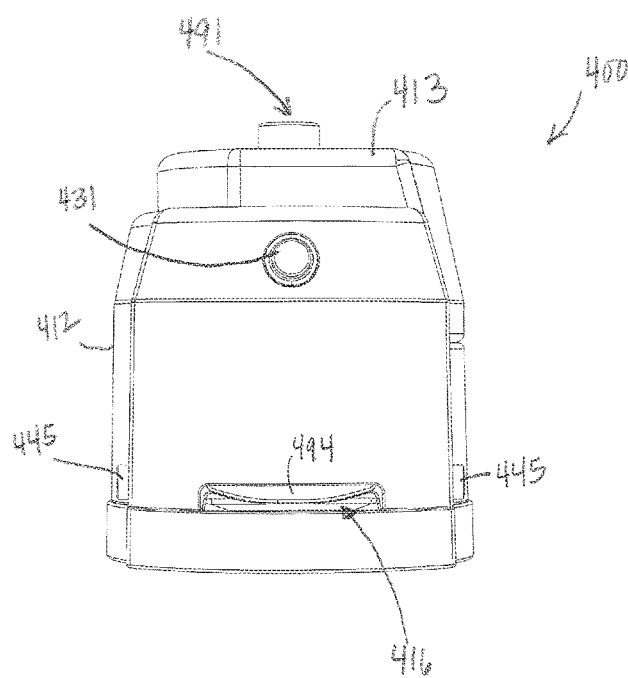
FIG. 12A
FIG. 12B

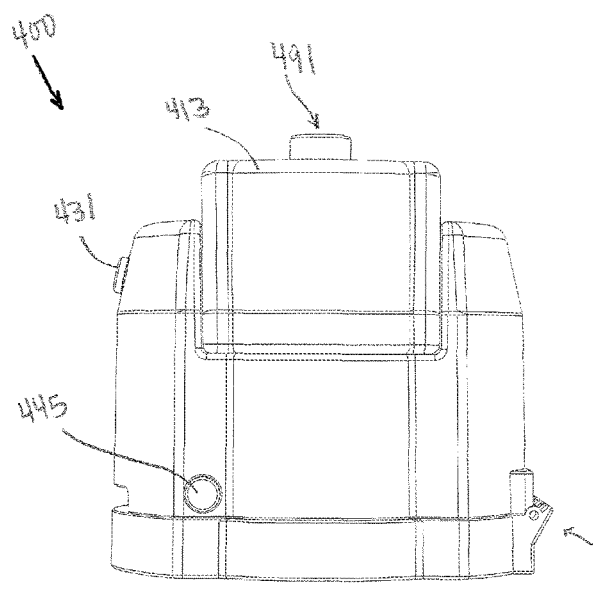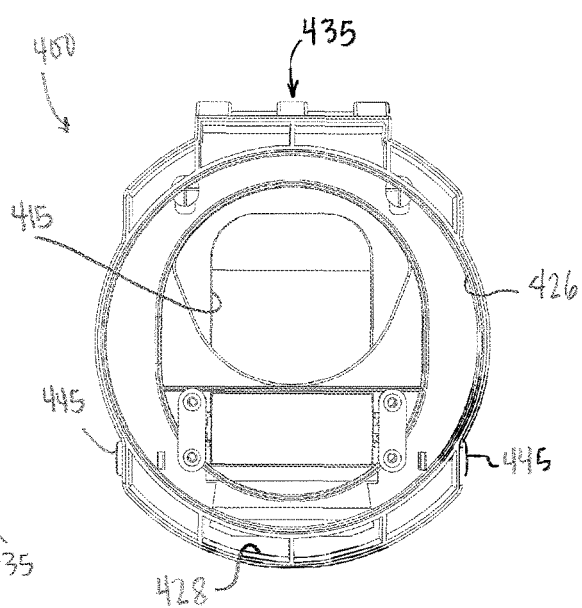
FIG. 12C
FIG. 12D

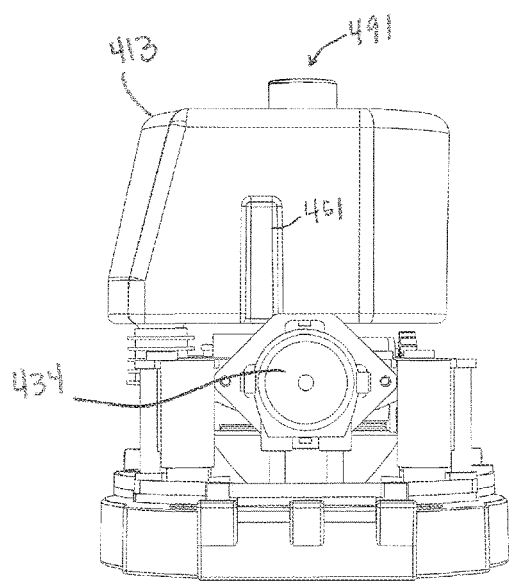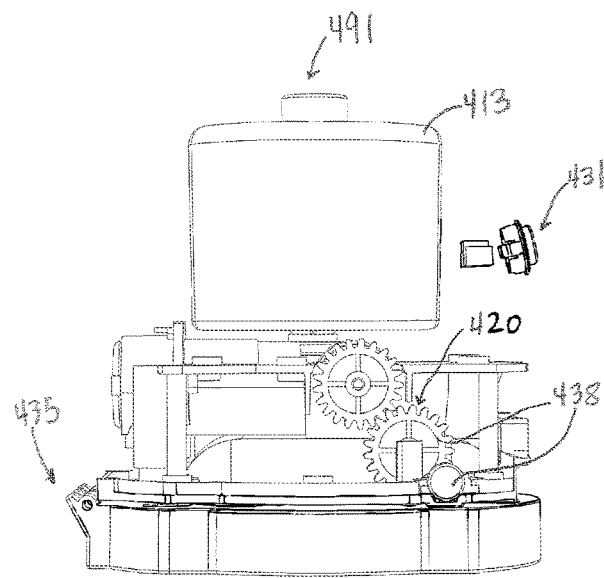
FIG. 12E
FIG. 12F

DEVICES, COMPOSITIONS, AND METHODS FOR USE IN SURFACE DECONTAMINATION

RELATED APPLICATIONS

This application is a continuation of U.S. application Ser. No. 17/257,997, filed Jan. 5, 2021, which is a U.S. National stage entry of International Application No. PCT/US2019/041604, which designated the United States and was filed on Jul. 12, 2019, published in English, which claims the benefit of U.S. Provisional Application No. 62/697,278, filed on Jul. 12, 2018 and U.S. Provisional Application No. 62/799,459, filed on Jan. 31, 2019. The entire teachings of the above applications are incorporated herein by reference.

TECHNICAL FIELD

The subject matter described herein generally relates to devices, indicator compositions, and methods for use in surface decontamination, specifically, in dispensing, monitoring, visualizing, and controlling application of indicator compositions to wipes, such as disinfectant wipes for surface decontamination.

BACKGROUND

A recent report published in *JAMA Internal Medicine* found that contamination of skin and clothing occurs during glove and gown removal in 60% of cases (ME Tomas, et al. (2015). Contamination of Health Care Personnel During Removal of Personal Protective Equipment. *JAMA Intern Med.* 175(12):1904-10.) When using educational intervention and visual feedback, the study found that the rate of contamination fell to 18.9%. However, providing training on proper personal protective equipment removal is not always feasible, especially in resource-limited settings or during epidemics, and many commonly used disinfectants do not provide visual feedback. Thus, there exists a need for improved compositions, methods and techniques to ensure proper disinfection of a variety of surfaces to reduce the rate of contamination.

Commercially available products such as Glo Germ™ have demonstrated the importance of visualizing disinfection. For instance, Glo Germ™ has been used in the Mount Sinai Health System to ensure that surfaces are completely disinfected (*The Wall Street Journal*, (2015 Nov. 2)). However, Glo Germ™ requires the use of an ultraviolet light for visualization, which may not be readily available in the field, and requires a power source. In addition, the need to apply Glo Germ™ before every disinfection and to carry around or install an ultraviolet light source can be tedious and infeasible for checking all disinfected surfaces in a fast-paced hospital setting.

Further studies have also demonstrated that improving compliance with decontamination protocols, include waiting sufficient contact time for a disinfectant to inactivate a pathogen can reduce the rate of hospital-acquired infections by more than 80% (R Orenstein, et al. (2011). *Infect Control Hosp. Epidemiol.* 32(11):1137-9.) This strongly suggests that a method for improving compliance with contact time is urgently needed to reduce the rate of infection in hospitals, as well as for consumer use.

There remains a need for new devices, compositions, and methods to ensure the thorough and efficient disinfection of surfaces. The present invention addresses this need.

SUMMARY OF THE INVENTION

In an aspect, described is a device for applying a composition to a wipe dispensed through the device. The device includes a housing at least partially surrounding an interior volume. An exterior wall of the housing defines a dispensing aperture extending through the exterior wall. A lower end region of the housing includes an opening through which at least one wipe of a plurality of wipes is drawn into the interior volume of the housing from a canister holding the plurality of wipes. One or more connecting features are on the lower end region of the housing. The device includes a dispensing mechanism positioned within the interior volume of the housing. The dispensing mechanism includes a plurality of rollers configured to capture and direct the at least one wipe through the interior volume of the housing towards the dispensing aperture. The device includes an application mechanism positioned within the interior volume of the housing relative to the dispensing aperture. The device includes a processor in operative communication with a sensor and an input. The sensor is configured to communicate to the processor information related to the at least one wipe directed towards the dispensing aperture.

The processor can be configured to monitor, analyze, and record in a memory of the device the information. The processor can be configured to control automatically at least one function of the device based on the information. The information communicated from the sensor to the processor can be synchronized with a time log. The information synchronized with the time log can indicate productivity of a user and/or activity of the device. The information communicated from the sensor to the processor can be analyzed by software program running on the processor. The information communicated from the sensor can indicate a number of the plurality of wipes dispensed through the dispensing aperture. The number of the plurality of wipes dispensed can be based on an amount time spent actuating the input of the device. The number of the plurality of wipes dispensed can be based on a number of revolutions made by the plurality of rollers. The number of the plurality of wipes dispensed can be based on perforations between each of the plurality of wipes dispensed detected by the sensor. The number of the plurality of wipes dispensed can be synchronized with a time log. The information communicated from the sensor to the processor can indicate timing between when a first wipe of the plurality of wipes is dispensed and a second wipe of the plurality of wipes is dispensed. The information communicated from the sensor to the processor can indicate a frequency of wipes dispensed over time. The information communicated from the sensor to the processor can indicate when multiple wipes are dispensed simultaneously.

The sensor can be an optical sensor or a mechanical sensor. The information communicated can be a presence of the at least one wipe of the plurality of wipes within the dispensing aperture. At least a portion of the at least one wipe can interface with the sensor. The device can further include a movable, mechanical cover located relative to the dispensing aperture that is configured to interface with the sensor. The information communicated by the sensor can be displacement of the cover relative to the dispensing aperture. The processor can be programmed to inactivate one or both of the application mechanism and the dispensing mechanism based on the information communicated from the sensor. The information communicated from the sensor can indicate the cover is displaced and has not moved for a period of time.

The processor can be programmed to cause the plurality of rollers to automatically withdraw the at least one wipe of the plurality of wipes away from the dispensing aperture after the period of time. The period of time can be between 10 seconds and 30 seconds, between 30 seconds and 1 minute, between 1 minute and 2 minutes, between 1 minute and 5 minutes, or between 1 minute to about 20 minutes, or between 1 minute to about 60 minutes.

The device can further include a user interface and the period of time can be programmable by a user on the user interface. The sensor can include a first sensor configured to interface with the at least one wipe of the plurality of wipes within the dispensing aperture. The device can further include a second sensor configured to interface with a movable, mechanical cover located relative to the dispensing aperture.

The exterior wall of the housing can form an upper surface of the device or a side surface of the device. The lower end region of the housing can be sized to couple to the canister holding the plurality of wipes. The one or more connecting features on the lower end region can be configured to removably couple the lower end region to the canister. When the device is coupled to the canister, an interior of the canister can be in fluid communication with the interior volume of the housing through the opening. The device can form a removable lid for the canister.

The device can further include an adapter having a first lip on an upper region of the adapter and a second lip on a lower region of the adapter. The first lip can be sized to reversibly couple to the lower end region of the housing and the second lip can be sized to reversibly couple to the canister. The one or more connecting features on the lower end region of the housing can be configured to removably couple the lower end region of the housing to an adapter. The adapter can include a sensor configured to interface with one or both of the device and the canister. The sensor of the device can be configured to interface with a corresponding element on the canister holding the plurality of wipes. The sensor of the device can be a mechanical sensor or an optical sensor. The corresponding feature on the canister can be a tactile series of ridges and bumps forming a code configured to be detected by the sensor. The code can provide information about the plurality of wipes contained within the canister. The code can delineate one or both of a chemistry of the plurality of wipes and wipe dimension.

The device can further include a removable cartridge configured to be coupled to the housing. The cartridge can include a cartridge housing defining a reservoir; and a penetrable barrier extending through a portion of the housing. The cartridge can include a sensor configured to detect liquid volume within the reservoir of the cartridge. The sensor of the cartridge can be an optical sensor or a mechanical sensor. The reservoir can be refillable. The reservoir can include two or more chambers sized to contain two or more separate compositions in each chamber. For example, the reservoir may contain 2, 3, 4 or more chambers adapted to contain 2, 3, 4, or more separate compositions that are separate components of a multi-component composition described infra. In some implementations, the reservoir can include a first chamber sized to contain a first composition and a second chamber sized to contain a second composition separate from the first composition. In some implementations, the reservoir can include a first chamber sized to contain a first composition, a second chamber sized to contain a second composition separate from the first composition, a third chamber sized to contain a third composition separate from the first two compositions, and optionally a fourth chamber sized to contain a fourth composition separate from the first three compositions. In some implementations, the reservoir can include more than 4 chambers. The application mechanism can be configured to apply each of the separate compositions to the at least one of the plurality of wipes. For example, in some implementations, the application mechanism can be configured to apply the first and second composition to the at least one of the plurality of wipes; or the application mechanism can be configured to apply the first, second, and third, or optionally fourth composition to the at least one of the plurality of wipes, and so on, where there are more than 4 separate compositions. It should be understood that the separate compositions are components of a multi-component indicator composition described here, in which each component is kept separate from the others until they are combined, e.g., at the point of use. In some implementations, the application mechanism is configured to apply each of the separate compositions to an article or surface simultaneously. In some implementations, a single application mechanism is configured to apply each of the separate compositions; in some implementations, two or more of the separate compositions are applied by different applicators. For example, the application mechanism can be configured to apply the first and second compositions simultaneously, or to apply the first, second, and third compositions simultaneously, and so on, for four or more compositions. The application mechanism can also include a first applicator for the first composition and a second applicator for the second composition, or three applicators for the first, second, and third compositions, etc. In some implementations where the application mechanism comprises two applicators, the first and second applicators can be arranged to dispense in parallel, in series, or in combination.

In some implementations, the multi-component indicator composition comprises at least two components contained in separate chambers of a cartridge, or two separate cartridges. In some implementations, the first component of the composition comprises a colorant and optionally an acidic agent or acidifying agent, and/or a corrosion inhibitor; and the second component comprises a disinfectant composition and optionally one or more surfactants and/or a rheology modifier. In some implementations, the colorant is selected from any of a triarylmethane, azo, indigoid, or acid dye, preferably selected from indigo carmine, Acid Blue 1, Direct Blue 1, or FD&C Blue 1; the optional acidic agent or acidifying agent is selected from citric acid, benzoic acid, acetic acid, hydrochloric acid, sulfuric acid, nitric acid, hydrofluoric acid, hydrobromic acid, perchloric acid, chloric acid, hydroiodic acid, sulfurous acid, methanoic acid, phosphoric acid, nitrous acid, benzenesulfonic acid, metaperiodic acid, ascorbic acid, trimethoxybenzoic acid, peracetic acid, oxalic acid, formic acid, glucaric acid, gluconic acid, tartaric acid, lactic acid, boric acid, carbonic acid, acrylic acid, phenylsuccinic acid, succinic acid, propanoic acid, and acidic buffers within the range of pH 0-7 comprised of acids and their necessary conjugate bases as well as optional stabilizing salts; and the optional corrosion inhibitor is sodium carbonate; and in the second composition, the disinfectant is a hypochlorite based disinfectant and the surfactant, if present, comprises one or more of sodium xylene sulfonate, disodium decyl phenyl ether disulfonate, and disodium oxybis[decylbenzenesulfonate].

In some implementations, the application mechanism can include at least one applicator; and a transfer element including a pump. The transfer element can transfer the amount of the first and second compositions from the reservoir towards the at least one applicator. The transfer element can create a pressure differential relative to an interior of reservoir to transfer the amount. The input can be an actuator configured to simultaneously activate the pump of the dispensing mechanism and the application mechanism. The dispensing mechanism can further include a motor. The actuator can activate the motor. The device can further include a removable cover positioned over the dispensing aperture. The actuator can open the cover exposing the dispensing aperture. The device can further include one or more grippers configured to engage the wipes during dispensing. The actuator can activate the one or more grippers. The actuator can activate one or more of the transfer element, the at least one applicator, the motor, the cover, and the grippers simultaneously. The pump of the transfer element can be powered by an electric motor upon actuation of the input to create a pressure differential relative to the interior volume of the reservoir. The pump can be a positive displacement pump, reciprocating pump, rotary pump, piston pump, diaphragm pump, peristaltic pump, dynamic pump, centrifugal pump, or hydraulic pump. The at least one applicator can be configured to apply the amount of first and second composition to the wipe by directly contacting the wipe. The application mechanism can provide for one-sided or two-sided application of the amount of the first and second composition to the wipe.

BRIEF DESCRIPTION OF THE FIGURES

These and other aspects will now be described in detail with reference to the following drawings. Generally speaking, the figures are not to scale in absolute terms or comparatively, but are intended to be illustrative. Also, relative placement of features and elements may be modified for the purpose of illustrative clarity.

FIG. 12A is a perspective view of an implementation of a device configured to apply an indicator solution to a wipe;

FIG. 12B is a front view of the device of FIG. 12A;

FIG. 12C is a side view of the device of FIG. 12A;

FIG. 12D is a bottom view of the device of FIG. 12A;

FIG. 12E is a back inside view of the device of FIG. 12A;

FIG. 12F is a side inside view of the device of FIG. 12A;

Figure 1A:
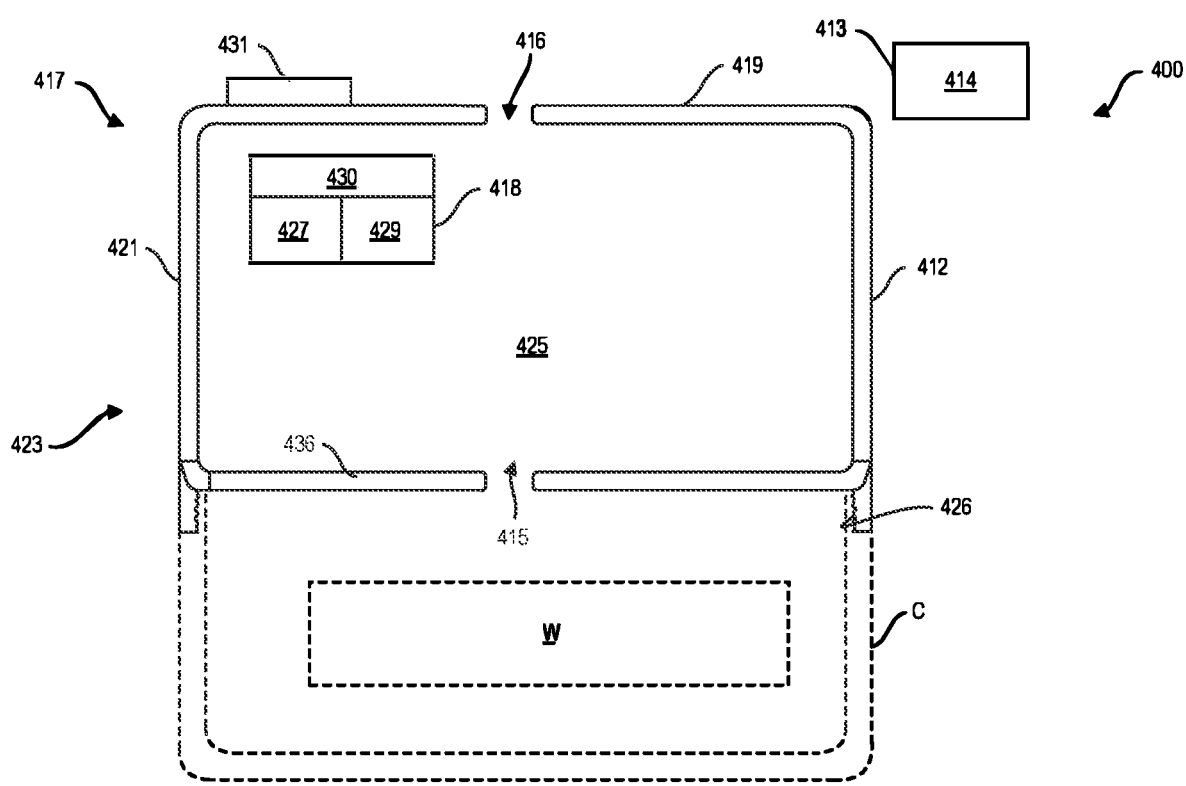
FIG. 1A is a schematic of an implementation of a device configured to apply an indicator solution to a wipe.

Generally speaking, the figures are not to scale in absolute terms or comparatively but are intended to be illustrative. Also, relative placement of features and elements may be modified for the purpose of illustrative clarity.

DETAILED DESCRIPTION

The present disclosure provides devices, compositions, and methods for surface disinfection and decontamination. The devices described here are generally adapted to contain a single or multi-component indicator composition, and optionally including a disinfectant composition, and to dispense the indicator composition and optional disinfectant composition to a disinfectant solution, a surface, or a disinfectant article upon actuation of the device. In some implementations, the disclosure provides an article of manufacture in the form of a removable cartridge adapted to fit a device described here, which may be pre-filled with a single or multi-component indicator composition as described here, and optionally with a disinfectant composition. As discussed infra, in some implementations the cartridge comprises two or more chambers adapted to keep the contents of the chambers separate until the device is actuated. In some implementations, the disinfectant composition is separate from the one or more components of a single or multi-component indicator composition, for example the disinfectant composition is contained in a separate chamber of a multi-chambered cartridge from the indicator composition, or components thereof. In some implementations, the disinfectant composition and one or more of the components of a multi-component indicator composition may be combined, for example in the same chamber of a multi-chambered cartridge with at least one of the components of the multi-component indicator composition.

In some implementations, the device takes the form of an adjustable and removable lid adapted to fit a canister containing a disinfectant solution or article such as a woven or non-woven fabric or sponge, which may optionally be in the form of a continuous sheet optionally perforated for ease of separation into smaller sheets, e.g., in the form of perforated cloths, towels, or wipes. In the context of the present disclosure, the article may also be referred to simply as a "wipe," which is understood to be a general term for an article that may take any of a variety of forms, including that of a cloth, pad, towel, or towelette, and which may be comprised of any of a variety of materials including a woven or non-woven fabric, sponge, gauze, cellulose, or polypropylene material. In some implementations, the device is adapted to dispense the indicator composition into a disinfectant solution contained in the canister, or onto at least one article of a plurality of articles contained in the canister.

The compositions described here are adapted to impart a visible color to a disinfectant composition, for example a hypochlorite based disinfectant, a hypochlorous acid based disinfectant, a dichloroisocyanurate based disinfectant, such as sodium dichloroisocyanurate, a quaternary ammonium based disinfectant, a quaternary ammonium/alcohol based disinfectant, an alcohol based disinfectant, an acid/alkali based disinfectant, a heavy metal based disinfectant, an aldehyde based disinfectant, a peroxide based disinfectant, for example a hydrogen peroxide based disinfectant, or a peracetic acid based disinfectant, which color fades to clear after application of the colored disinfectant to a surface, thereby providing an indication of both surface coverage and time of contact with the surface which together provide an indication of adequate decontamination and/or disinfection of the surface. Accordingly, the compositions described here are generally referred to as 'indicator compositions'. In some implementations, the disinfectant composition is an aqueous solution comprising a disinfectant selected from sodium hypochlorite, sodium dichloroisocyanurate, potassium dichloroisocyanurate, hypochlorous acid, hydrogen peroxide, ethyl alcohol, a quaternary ammonium compound, a mixture of a quaternary ammonium compounds, a mixture of a quaternary ammonium compound(s) and an alcohol(s), an alcohol, peracetic acid, accelerated hydrogen peroxide, chlorine dioxide, calcium hypochlorite, chlorhexidine gluconate, glutaraldehyde, formaldehyde, and phenol. In some implementations, the disinfectant composition may comprise aldehydes (e.g., formaldehyde, glutaraldehye, and ortho-phthalaldehyde), hydrogen peroxide-peracetic acid combinations, iodophors, and phenols or phenolics.

In some implementations, an indicator composition according to the disclosure is a single component composition, or alternatively, is formed from the combination of two or more separate components which are kept physically separated prior to use, optionally within a container or reservoir having a plurality of separate compartments and adapted to fit within a device, for example in the form of an integral or removable cartridge, as described herein. In some implementations, a device as described herein may accommodate two or more cartridges, each adapted to contain a single composition, or one or more components of a multi-component composition described here.

In some implementations, an indicator composition is provided along with a disinfectant composition in a device adapted to combine the indicator composition(s) and the disinfectant composition at the point of use, for example upon actuation of the device. The indicator composition may be a single or multi-component composition. Where the indicator composition is a multi-component composition, it may be provided in an article of manufacture, such as a removable cartridge, adapted to fit removably within a device configured to mix the several components of the multi-component composition upon actuation of the device, thereby forming a single component indicator composition at the point of use. The device may also be adapted to dispense the resulting single component indicator composition onto a surface or article, or into a disinfectant composition, such as a hypochlorite based disinfectant, a quaternary ammonium or alcohol based disinfectant, a hydrogen peroxide based disinfectant, or a peracetic acid based disinfectant. In some implementations, the device is adapted to dispense the single or multi-component indicator composition along with a disinfectant composition which may be dispensed from a further compartment or reservoir of the device, or which may be dispensed through another mechanism, onto the surface or article.

In some implementations, the device is configured to apply a single or multi-component indicator composition as described herein onto an article, such as a woven or non-woven fabric or sponge article, where the article is optionally dry or pre-saturated with a disinfectant composition. In some implementations, the single or multi-component indicator composition is applied to the disinfectant composition or article upon actuation of a device containing the indicator composition, and optionally also containing the disinfectant composition. For example, where a woven or non-woven fabric or sponge article, such as a wipe, is housed within a container, a device as described here is adapted to couple securely to the open top of the container and configured to permit threading of the article into the device in a manner that brings the article into proximity with a means for dispensing the single or multi-component indicator composition, and optionally a disinfectant composition, onto the article and then dispensing the article through an opening of the device for use in application to a surface.

The single and multi-component indicator compositions described here contain a colorant, generally in the form of a water soluble dye or lake pigment, a catalyst which modulates the transition of the colorant from a visible color to colorless, and one or more optional additives. In this context, the term 'catalyst' is used to refer to an agent that directly or indirectly modulates the loss of color from the colorant, or the 'fade time' of the colored disinfectant composition following addition of the indicator composition thereto, meaning the time required for the colored disinfectant composition to fade to clear, for example after application to a surface. In some implementations, the catalyst may be provided by the disinfectant composition itself. In some implementations, the catalyst is a component of the indicator composition. The colorants and catalysts which may be used in the present compositions are described in more detail in the "Compositions and Methods" section below.

In some implementations, the colorant of the indicator composition does not include fluorescent substances and instead includes only substances that impart color by the selective absorption or scattering of light. In some implementations, the colorant is a water soluble oxidizable dye or pigment. In some implementations, the colorant is not a pH sensitive dye or pigment. In some implementations, a single or multi-component indicator composition as described here does not contain a pH sensitive dye or an alkaline builder in combination.

In some implementations the one or more optional additives is selected from one or more of a pH modulator such as an acidic agent, an alkaline builder or base, or a suitable buffer system adapted to maintain a desired pH, a surfactant, a corrosion inhibitor, a perfume or fragrance, which may be an oil, a humectant, and a rheology modifier. In some implementations the one or more additional additives serves to improve the aesthetics of the composition, for example, a perfume, fragrance, or humectant, or to enhance the disinfectant and/or decontamination properties of the composition, including for example, one or more of a pH modulator, a surfactant or combination of surfactants, a corrosion inhibitor, and a rheology modifier. The optional additives which may be used in the present compositions are described in more detail in the "Compositions and Methods" section below.

The indicator compositions described here can be formulated as a liquid, gel, or powder.

In some implementations, a multi-component indicator composition as described here may also further comprise a disinfectant composition. In some implementations, the colorant of a multi-component indicator composition comprising a disinfectant composition is not a pH sensitive dye and the composition does not comprise an alkaline builder.

In some implementations, the indicator composition and the disinfectant composition are contained in at least two separate compartments formed by at least one interior wall of a container or reservoir and adapted to fit within a device as described herein, for example in the form of a removable cartridge.

In some implementations, the disinfectant composition may be pre-applied to an article, such as a wipe or cloth, or the article may be saturated with the disinfectant composition, or the disinfectant composition may be pre-applied to a surface, for example by wiping or spraying onto a surface, before addition of an indicator composition of the present disclosure; or the disinfectant solution and the indicator solution may be mixed together before application to the article or surface.

In accordance with any of the implementations described here, the disinfectant composition may be selected from an aqueous or non-aqueous solution of sodium hypochlorite, calcium hypochlorite, sodium dichloroisocyanurate, didecyldimethylammonium chloride, chlorhexidine gluconate, a phenol, an aldehyde, a terpene, hydrogen peroxide, chlorine dioxide, peroxy and peroxo acids such as peracetic acid, quaternary ammonium compounds, inorganic compounds such as metals and acids, and alcohols such as ethanol and isopropyl alcohol. In some implementations, the disinfectant composition is selected from an aqueous solution of hypochlorite, dichloroisocyanurate, hydrogen peroxide, peracetic acid, a quaternary ammonium compound (including mixtures of quaternary ammonium compounds and mixtures with alcohol), and an alcohol.

In the context of the present disclosure, the term "about" in reference to a numerical value is meant to encompass variations of +/−25%, preferably +/−15% or +/−10% from the stated value.

Devices

FIG. 1A is a schematic of an implementation of a device configured to apply one or more fluid compositions to a wipe as the wipe is dispensed from its canister. In some implementations, the fluid composition comprises an indicator composition and/or a disinfectant composition as described herein. However, other fluid compositions may also be applied and the device is not limited by the nature of the fluid composition, which may comprise, for example, an all-purpose cleaner, soap, detergent, metal cleaner, window cleaner, hand-surface cleaner, paint, primer, polish, lotion, etc. It should also be appreciated that the environment in which the devices and compositions described herein can vary and may include the home, food business, hospital, nursing or other care facility, etc.

The device 400 can include a housing 412 having a dispensing aperture 416 and an application mechanism 418 configured to be in fluid communication with a reservoir 414. The application mechanism 418 can be a direct contact type application mechanism or a non-contact application mechanism, which will be described in more detail below. The device 400 can optionally include a dispensing mechanism 430 configured to dispense the wipes W from the canister C. Each of the components will be described in more detail below.

Again with respect to FIG. 1A and as also shown in FIGS. 4A-4M, FIGS. 11A-11G, and FIGS. 12A-12I, the housing 412 can at least partially surround an interior volume 425 and have a wall defining the dispensing aperture 416 extending through a wall of the housing 412. The location of the dispensing aperture 416 can vary. For example, the dispensing aperture 416 can extend through an upper surface 419 or a side surface 421 of the housing 412 near an upper end region 417 of the housing 412. A lower end region 423 of the housing 412 can define an internal aperture or opening 415 such that when the housing 412 is coupled to a region of the canister C of wipes W, such as an upper end of the canister C, the wipe W stored within the interior of the canister C can be drawn into the interior 425 of the housing 412 through the opening 415. When the device 400 is coupled to the canister C of wipes W, an interior of the canister C can communicate with or be placed in communication with the interior 425 of the housing 412 through the opening 415. The wipe W stored within the interior of the canister C can enter the interior 425 of the housing 412 from the lower end region 423 through the opening 415 and fed towards the dispensing aperture 416 in the upper end region 417. The dispensing aperture 416 need not be in the upper end region 417 and can also be found near a lower end region 423 of the housing.

The dispensing aperture 416 can be configured to allow single or multiple wipes W to be dispensed through it. The dispensing aperture 416 can be a slit having a rectangular, cross, x, flower petal, or zig-zag shape. The size and shape of the dispensing aperture 416 can vary depending on whether the device 400 is configured for manual dispensing or automatic dispensing. For example, the device 400 can optionally include a dispensing mechanism 430 that is an automatic dispensing mechanism or manual. The dispensing mechanism 430 can be configured to arrange the wipe W in a manner that encourages uniform application of the composition to the wipe W as the wipe W is fed through the interior 425 of the housing 412 towards the dispensing aperture 416. The dispensing aperture 416 for the automatic dispensing mechanism 430 can be a rectangular-shaped dispensing aperture 416 whereas the manually dispensed configuration may incorporate a zig-zag shaped dispensing aperture 416. The size and shape of the dispensing aperture 416 can be selected to assist in separating the wipes W from one another. Wipes W can be packaged such that they are stacked in interlocking folds or are arranged such that each sheet is connected to the other and separated by perforations. Depending on the overall configuration of the dispensing aperture 416, a plurality of flaps can be formed that are configured to compress the wipe W as it extends through the dispensing aperture 416. This can provide more or less volume of a liquid composition, such as an indicator composition and/or a disinfectant composition described herein, or other composition as described above, to be applied to the wipe W, or leave more or less volume of the composition impregnated on wipe W, as it is dispensed. The larger the space between the flaps of the dispensing aperture 416 the greater the volume of the composition maintained on the wipe W and vice versa.

The device 400 can optionally include a mechanism that aids in separating sheets of wipes W from one another. For example, a pincher mechanism can be included that pivots towards the wipes W as they extend through the interior of the device 400 to capture the sheets of wipes W and allow for easier separation. In some implementations, the wipe W is dispensed through the device 400 manually such as by a user pulling the wipe W through the dispensing aperture 416 (e.g. through a top surface 419 or a side surface 421). In some implementations, the wipe W is dispensed through the device 400 by a dispensing mechanism 430 that is an automatic feed system including a powered motor. Regardless of the mechanism by which the wipe W is dispensed through the device 400, the wipe W that is dispensed has a composition applied, for example an indicator composition and/or a disinfectant composition described herein, or other composition as described above.

Figure 4A:
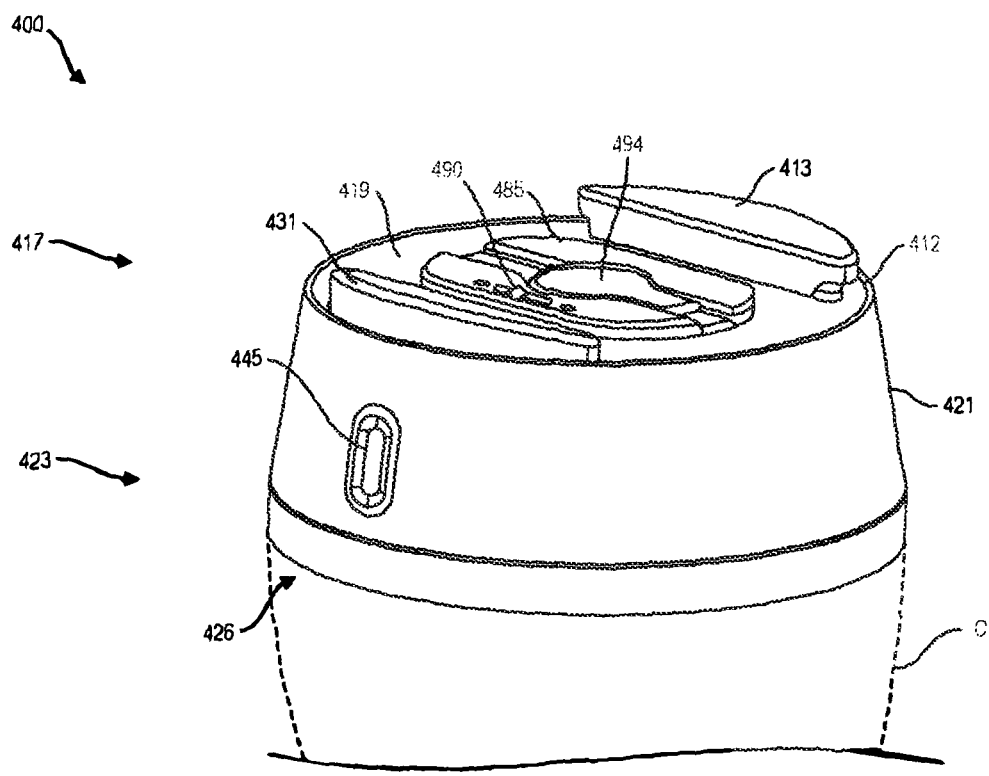
FIG. 4A is a perspective view of an implementation of a device configured to apply an indicator solution to a wipe.
Figure 4B:
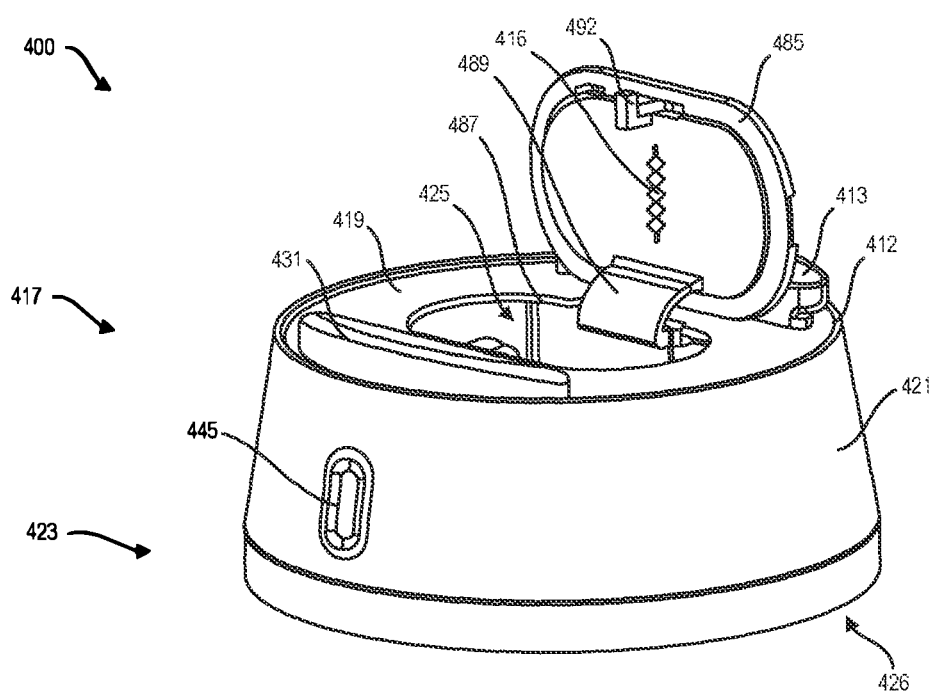
FIG. 4B is a perspective view of the device of FIG. 4A exposing an interior of the device housing.
Figure 4C:
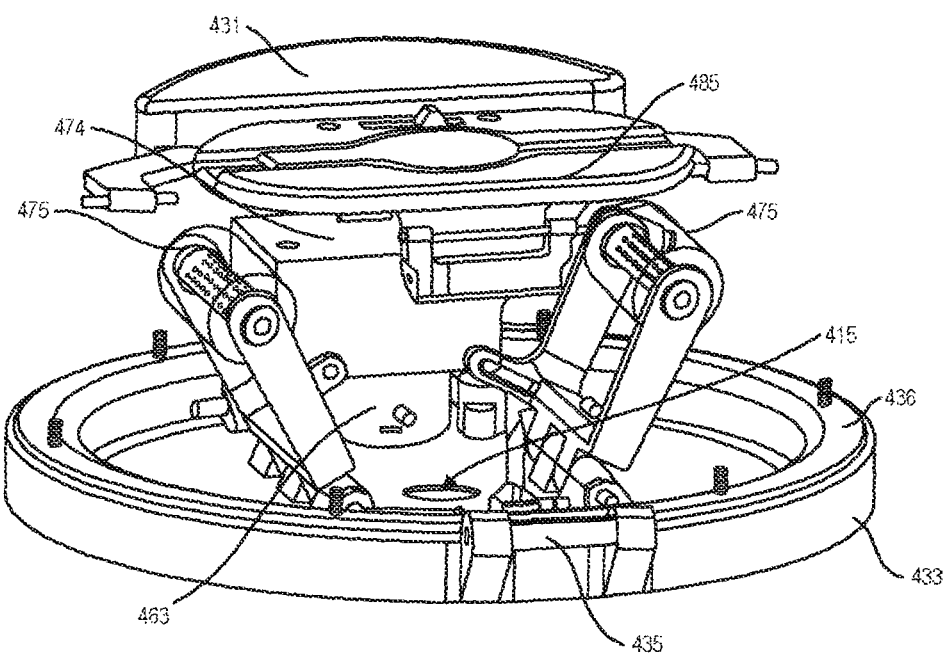
FIG. 4C is an exploded, partial perspective view of the device of FIG. 4A.
Figure 5A:
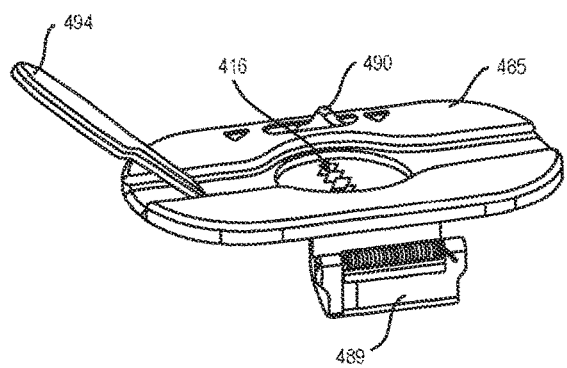
FIGS. 5A-5B are various views of a dispensing aperture in a cap of the device of FIG. 4A.
Figure 5B:
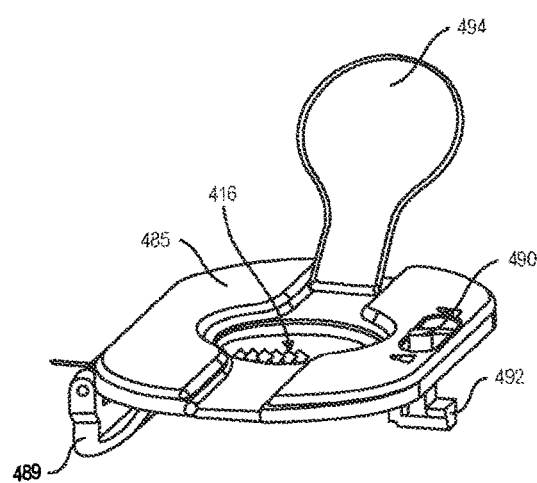

In some implementations, the dispensing aperture 416 extends through a cap 485 movably coupled to an upper surface 419 of the housing 412 (see FIG. 4B and also FIGS. 5A-5B). The upper surface 419 of the housing 412 can define an opening 487 that is covered by the cap 485. The cap 485 can be coupled to the upper surface 419 of the housing 412 by a hinge 489 such that the cap 485 can be opened revealing an interior 425 of the housing 412 through the opening 487. The cap 485 can also include a locking element 490 having a latch 492 that can be toggled between a locked configuration keeping the cap 485 in the closed position over the opening 487 and unlocked configuration allowing the cap 485 to hinge open revealing the interior 425 through the opening 487. Opening the cap 485 can be helpful, for example, to thread the first wipe W into the device 400. The cap 485 can additionally include a cover 494 over the dispensing aperture 416 to avoid inadvertent drying out of the wipes W in their canister C. The cover 494 can be hinged such that the cover 494 can be manually or mechanically opened. For example, the cover 494 can include a spring-loaded hinge that opens when an actuator is pushed. In some implementations, the actuator 431 can simultaneously release the cover 494, activate the transfer element 427 to pump a fluid composition towards the applicator 429, and activate the applicator 429 to apply the transferred composition to the wipe W. The actuator 431 can also simultaneously activate any gripper, pincher elements so that the fluid saturated wipe W is released and ready for use. The cover 494 can also automatically close (and the gripper automatically released) when the actuator 431 is released to prevent the wipes W within the canister C from drying out. Consolidating the various mechanisms into a single actuation simplifies use of the device 400 such that it can be used with a single hand. It should be appreciated, however, that the various components can also include their own actuator and/or be configured for manual use.

The lower end region 423 of the housing 412 can incorporate one or more connecting features 426 configured to removably or detachably couple the device 400 to the canister C of wipes W. The connecting feature 426 can include a thread corresponding to a thread of the canister C, a snap-fit connection, fitting, fastener, or coupling feature sized to fit a region of the canister C. In some implementations, the device 400 is configured to connect to the canister C such that the device 400 functions as a lid on an open end of the canister C. The device 400 can be used to replace an existing lid on the canister C. As such, the connecting feature 426 can be designed according to dimensional standards for container closures. The connecting feature 426 also can be adjustable such that it can fit variable sizes of canisters. In other implementations, the device 400 is configured to connect to the canister C already enclosed with a lid having a dispensing aperture. In this implementation, the device 400 can function as an auxiliary attachment to the already enclosed canister C. The device 400 need not be removable from the canister C and can be a single-use device affixed to a canister C of wipes W. The connecting feature 426 can include a bottom ring 433 sized to surround and engage with an upper rim of the canister C of the wipes W (see FIG. 4D). The bottom ring 433 can include one or more grooves, threads, snap-fit feature, or other coupling features that allows the device 400 to be attached to the canister C. In some implementations, the bottom ring 433 is a universal coupler that allows it to be attached to canisters C of various sizes. The bottom ring 433 can incorporate a drain hole 428 (see FIG. 12D) that allows for any excess liquid from the dispensed wipe W to drain back into the canister C.

Figure 4D:
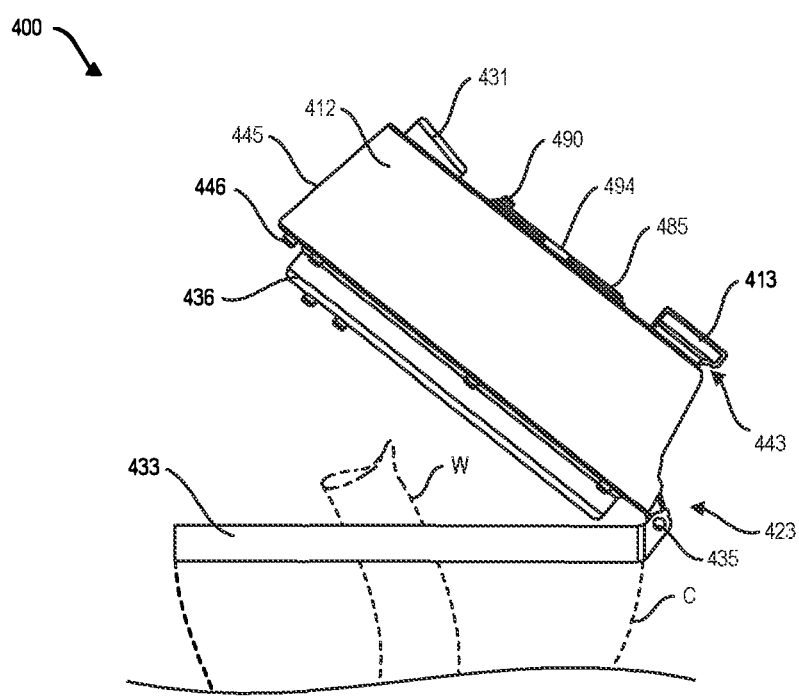
FIG. 4D is a side view of the device of FIG. 4A showing the housing in an articulated position.

Still with respect to FIG. 4D, the bottom ring 433 can be coupled by a hinge element 435 to an upper plate 436 affixed to a lower end region 423 of the housing 412. The upper plate 436 defines the internal opening 415 through which the wipe W extends into the interior 425 of the device 400. A release button 445 can be incorporated that when actuated releases a latch 446 engaging the bottom ring 433. Actuation of the release button 445 moves the latch 446 thereby releasing engagement between the lower end region 423 of the housing 412 and the bottom ring 433. This allows the housing 412 to be opened and hinge relative to the bottom ring 433 when the device 400 is coupled to a canister C. This exposes the upper end of the canister C through the aperture 415 without removing the entire device 400 from the canister C. Hinging the device 400 into an opened position in this way may be helpful when a user needs to assist with priming the lead or first wipe W into the device 400, which will be described in more detail below. In some implementations, the hinge 435 can include stoppers to limit the angle at which the lid can be opened. The hinge stopper can prevent the container from tipping backwards upon articulating the upper portion relative to the lower portion of the device 400.

FIGS. 12A-12I illustrate an implementation of the device 400 having a pair of release buttons 445 positioned on either side of the housing 412. The pair of buttons 445 can be squeezed by a single hand toward one another to release and open the housing 412 to expose the upper end of the canister C through the aperture 415. Additionally, upon hinging open the housing 412, the upper portion can include a sealed gasket or other element to enclose the components of the housing 412. The gasket can minimize noise of the components as well as providing better aesthetics and protection for the components. Additionally, one or more of the moving parts within the housing 412 (e.g. motor, gearbox, pumping element) can be in a sealed enclosure or encased to maintain a quieter functioning device that is more robust.

The reservoir 414 (which can be a removable reservoir) can have at least one reservoir chamber sized to contain an amount of a composition, for example an indicator composition and/or a disinfectant composition described herein, or other composition as described above. The device can include more than one reservoir 414 or a single reservoir 414 divided into two or more separate chambers sized to hold volumes of different compositions. The volume of the reservoir 414 can be sufficient to dispense enough of a composition for the number of wipes in the bucket the lid fits onto. In embodiments where the device includes at least two reservoirs 414 or a single reservoir 414 divided into at least two separate chambers, the different compositions may include, for example, two solutions which, when applied to the wipe by actuation of the device, form an indicator composition in situ, on the wipe. Examples of two-part and multi-part indicator compositions are described in more detail below. In other embodiments, the different compositions which are held either in two or more reservoirs 414 or in a single reservoir 414 divided into at least two separate chambers may include an indicator composition and another composition, such as a disinfectant composition, which are both applied simultaneously to the wipe by actuation of the device. The disinfectant composition is preferably a solution comprising a suitable amount of a disinfectant material selected from an aqueous or non-aqueous solution of sodium hypochlorite, calcium hypochlorite, sodium dichloroisocyanurate, didecyldimethylammonium chloride, chlorhexidine gluconate, a phenol, an aldehyde, a terpene, hydrogen peroxide, chlorine dioxide, a peroxy and peroxo acid such as peracetic acid, a quaternary ammonium compound, an inorganic compound such as metals and acids, and alcohols such as ethanol and isopropyl alcohol.

In embodiments, the amount of composition applied to the wipe is in the range of from 0.0001-0.1 ml per square centimeter ($cm^2$) of the wipe, preferably from 0.001-0.05 ml/$cm^2$ of wipe. Accordingly, where the reservoir is referred to herein as a single reservoir it should be appreciated that the reservoir can be configured to hold a sufficient amount of a composition for application to a plurality of wipes.

Figures 4E, 4F:
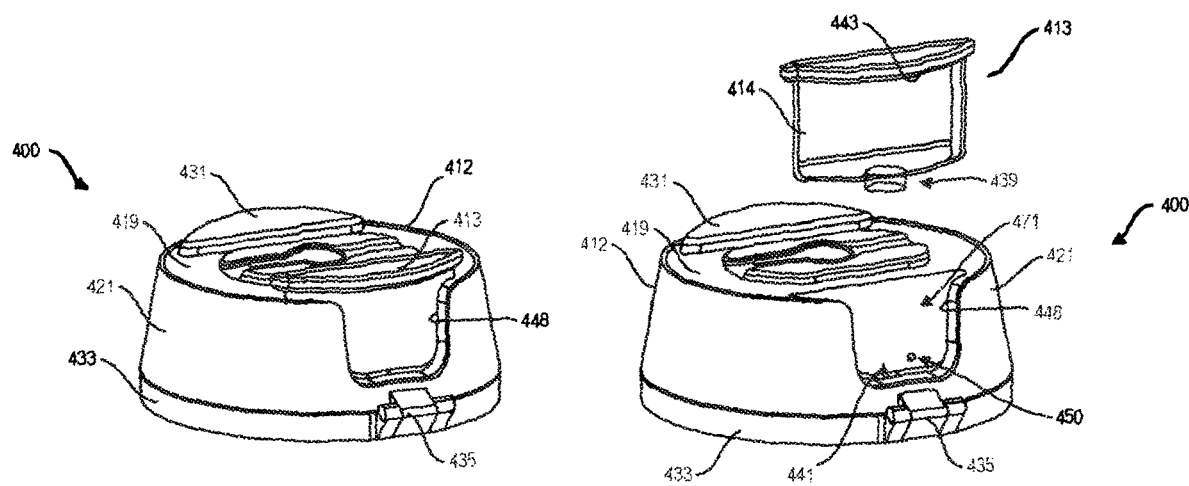
FIG. 4E is a perspective view of the device of FIG. 4A.
FIG. 4F is a partially exploded view of the device of FIG. 4E with a cartridge removed from the housing.
Figure 4G:
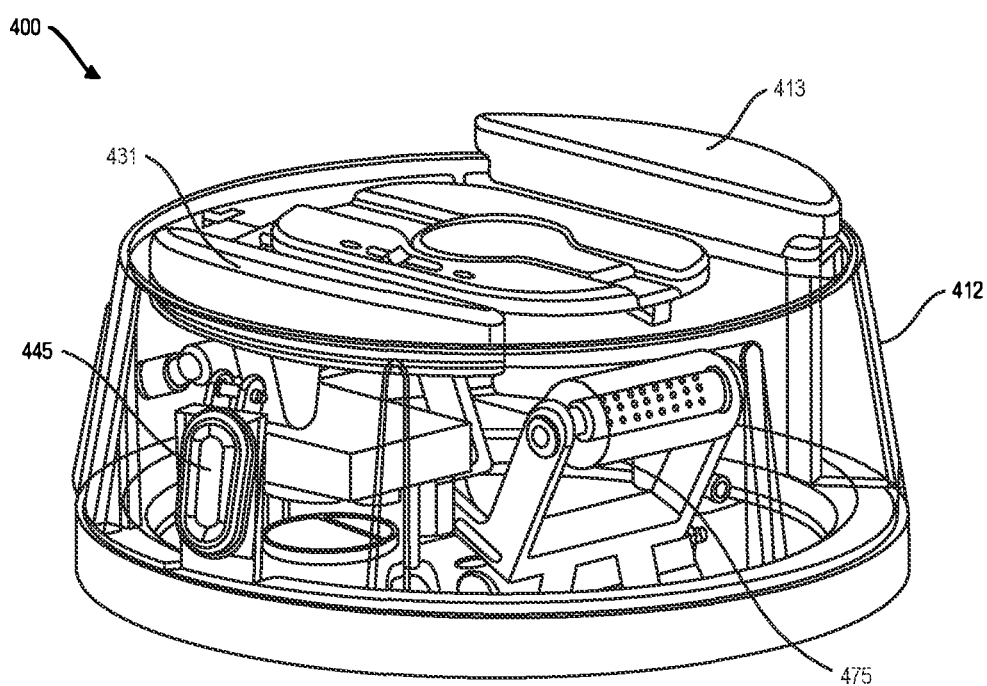
FIG. 4G is a perspective view of the device of FIG. 4A in which the housing is transparent.
Figure 4H:
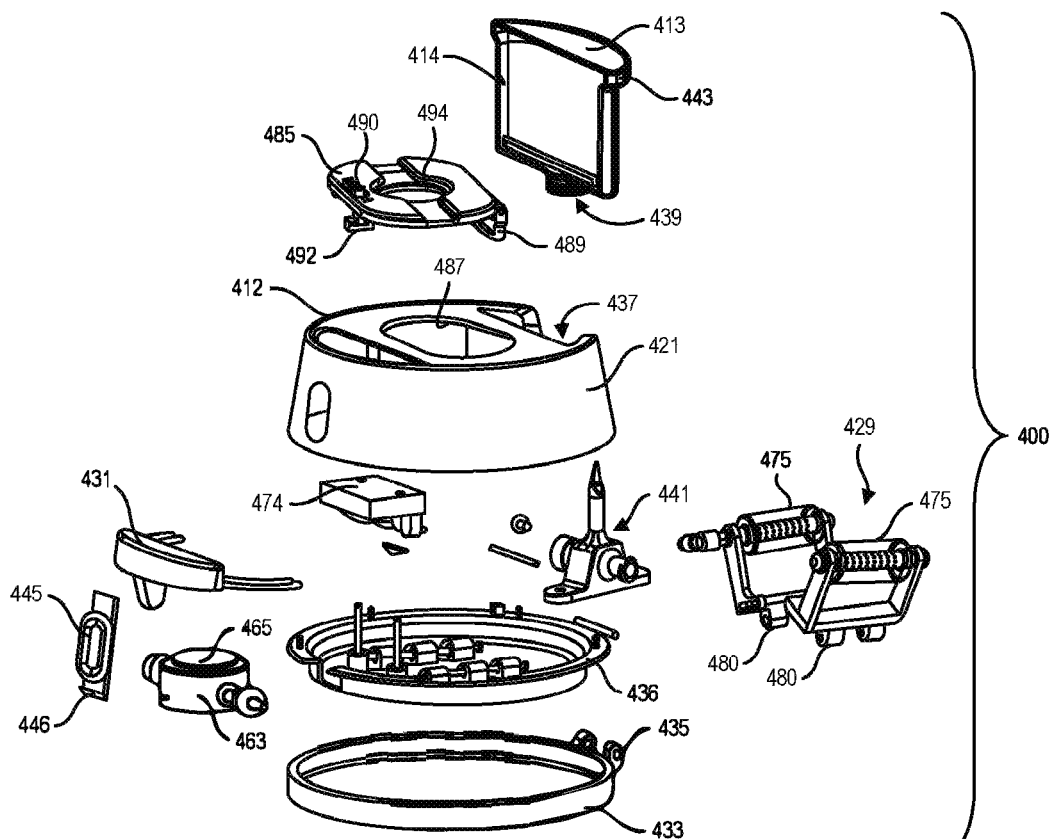
FIG. 4H is an exploded view of the device of FIG. 4A.

The reservoir 414 can be located at least partially within the housing 412. The reservoir 414 can be refillable and/or removable from the housing 412. In some implementations, the reservoir 414 can be contained within a cartridge 413 having a housing configured to removably couple to a region of the housing 412, which will be described in more detail below. As best shown in FIGS. 4E-4F and also FIGS. 6A-6B, the cartridge 413 is configured to removably couple with a region of the housing 412. In some implementations, the housing 412 can include a receptacle region such as a slot 437 sized and shaped to receive at least a portion of the cartridge 413. The cartridge 413 can slide with the slot 437 from the top surface 419 of the housing 412 such that a coupling feature 439 of the cartridge 413 engages with a corresponding coupling feature 441 within the slot 437 of the housing 412. Engagement between the coupling features 439, 441 can result in the interior of the reservoir 414 being placed in fluid communication with at least a portion of the application mechanism 418. In some implementations, the coupling feature 439 of the cartridge 413 includes a septum or other penetrable barrier and the coupling feature 441 within the slot 437 of the housing includes a spike or other element configured to penetrate the septum. In some implementations, the housing may include a receptacle region sized and shaped to receive two or more cartridges.

Figure 12G:
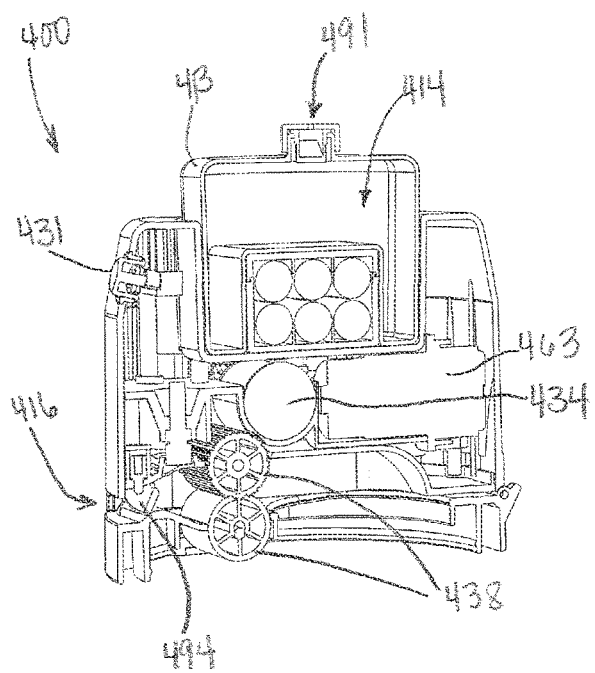
FIG. 12G is a vertical, cross-sectional view of the device of FIG. 12A.
Figure 12H:
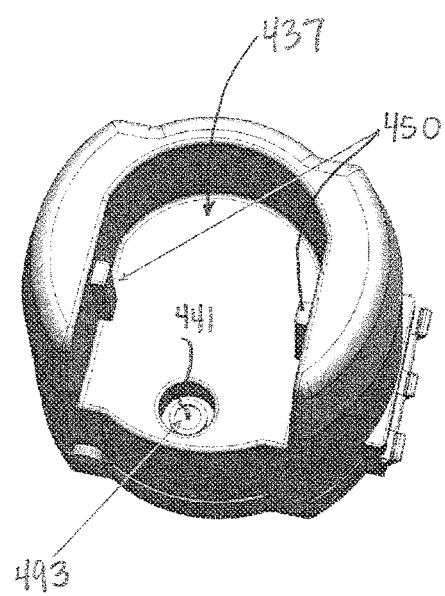
FIG. 12H is a top view of the device of FIG. 12A without a cartridge installed.
Figure 12I:
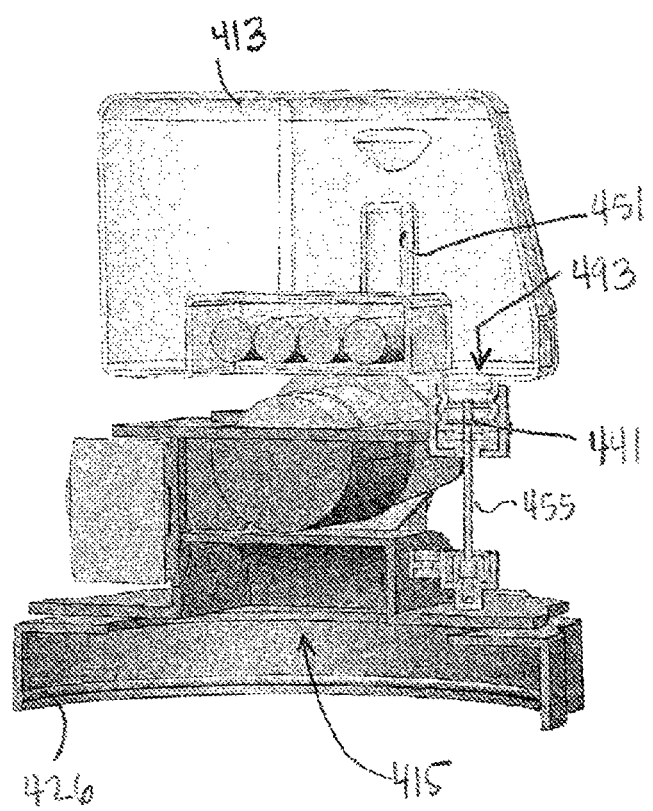
FIG. 12I is a partial cross sectional view of the device of FIG. 12H with a cartridge installed.

FIG. 4F shows the distal tip of the coupling feature 441 extending upward from within the receiver slot 437. The receiver slot 437 creates an inset surrounding the coupling feature 441 such that upon insertion and removal of the cartridge 413 solution from the reservoir 414 does not leak out of the slot 437. FIGS. 12H-12I illustrate an implementation of the device 400 in which the receiver slot 437 has an inset 493 surrounding the coupling feature 441. The inset 493 is as deep as the portion of the coupling feature 441 available to penetrate coupling feature 439 of the cartridge 413 is long. This prevents the coupling feature 441 from extending into the slot 437 and eliminates the possibility of solution leaking onto the outside surface of the housing 412.

Figure 6A:
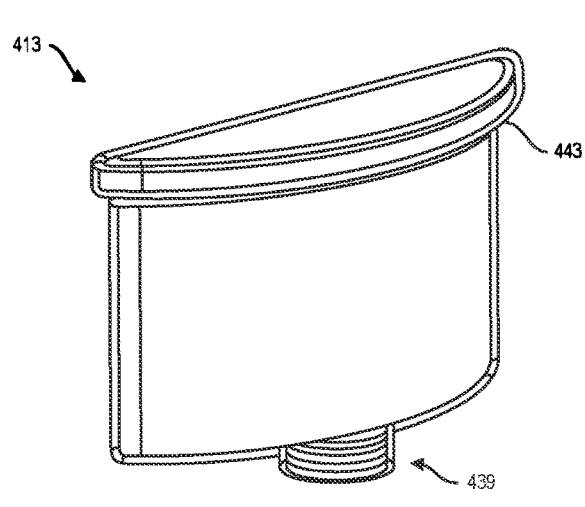
FIGS. 6A-6B are perspective views of a cartridge of the device of FIG. 4A.
Figure 6B:
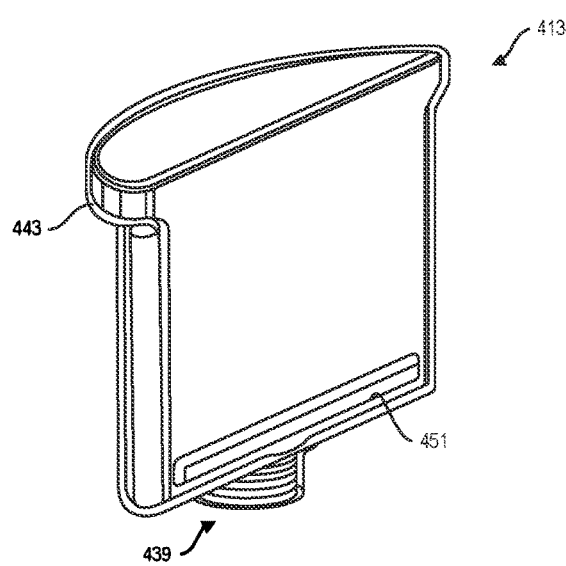

The slot 437 can also include one or more alignment features 450 configured to engage with one or more corresponding surface features 451 on the cartridge 413. Engagement between the alignment feature(s) 450 and the surface feature(s) 451 provides a snap-in feel so the user is aware the cartridge 413 is properly in place within the slot 437. FIGS. 6A-6B show an implementation of the cartridge 413 having a horizontal groove 451 extending along a lower surface of the cartridge 413. FIG. 12E and FIG. 12I illustrate another implementation of a cartridge 413 having a pair of surface features 451 that are grooves extending vertically along opposite sides of the cartridge 413. The grooves engage with corresponding alignment features 450 within the slot 437 to aid in sliding the cartridge in the correct orientation relative to the device 400. The engagement between the alignment features 450 and the surface features 451 can vary. The cartridge 413 can be removed by pulling upward relative to the device 400 and snapped in by pushing downward on the cartridge 413 relative to the device 400. The cartridge 413 can include additional surface features that aid a user's grip during insertion and removal of the cartridge 413. It should be appreciated that the cartridge 413 can engage with the housing 412 in various ways and is not limited to sliding. For example, the cartridge 413 can snap onto an exterior wall of the housing 412, can be threaded relative to the housing 412, or can be dropped into a fully enclosed channel into the interior 425 of the housing 412. Additionally, the cartridge 413 need not be inserted from an upper surface 419 of the device and can be inserted from a side or elsewhere on the cartridge 413. The features of the cartridge 413 described herein can be incorporated with any of a variety of the devices 400 and should not be limited to any particular device 400 having any particular feature (i.e. contact or non-contact style applicator mechanism 418 of dispensing mechanism 430).

The application mechanism 418 of the device 400 can include a transfer element 427 and at least one applicator 429. The transfer element 427 is configured to transfer an amount of a liquid composition from the reservoir 414 to the applicator 429, which in turn is configured to apply the amount of the composition to the wipe W dispensed through the dispensing aperture 416 of the device 410. The transfer element 427 thus drives the amount of composition in a direction towards the applicator 429. The transfer element 427 can create a pressure differential between the inside of the reservoir 414 where the composition is being stored and a region outside the reservoir 414. The pressure differential can be created by the transfer element 427 due to creation of a positive pressure within the reservoir 414 pushing the amount of the composition towards the applicator 429. The pressure differential can be created by the transfer element 427 due to creation of a negative pressure outside of the reservoir 414 pulling the amount of composition towards the applicator 429. In some implementations, the transfer element 427 creates a positive pressure within the reservoir 414 by pressing on a region of the reservoir 414 or the fluid inside the reservoir 414 and causing displacement of the volume from the reservoir 414 through an outlet. The transfer element 427 can shrink the chamber volume of the reservoir 414 forcing a volume of the composition from the reservoir 414. The transfer element 427 can also expand a chamber volume outside the reservoir 414 causing a volume of the composition from the reservoir 414 to flow towards the expanded chamber. The transfer element 427 creates the pressure differential by a pumping action, either a manual pumping action or by an electric- or battery-powered motor to create the pumping action. In some implementations, a battery can be coupled to the reservoir 414 to drive the motor to create the pumping action. In the case of a manually-created pumping action, the transfer element 427 can include a trigger, button, actuator, or other manual input or actuator 431 that creates the pressure differential relative to the interior of the reservoir chamber 414 directly when pressed or squeezed or otherwise manually actuated. In the case of an electrically-powered pumping action, the transfer element 427 can include a motor-powered mechanism to create the pressure differential relative to the interior of the reservoir chamber 414 upon actuation such as by a trigger, button, actuator, or other input that can be electrical or manual such as actuator 431. The transfer element 427 can also use gravity to transfer an amount of the composition towards the applicator 429 and need not incorporate pumping action.

As mentioned above, the applicator 429 is configured to apply the amount of a liquid composition transferred by the transfer element 427 to the wipe W dispensed through the device 400. The configuration of the at least one applicator 429 of the application mechanism 418 can vary. In some implementations, the applicator 429 applies a composition to the wipe W by directly contacting the wipe W such as with one or more rollers, brushes, ball-bearing devices, or other contact elements known in the art. FIGS. 4A-4K show implementations of devices incorporating direct contact style applicators. In other implementations, the applicator 429 applies a composition to the wipe W without the applicator 429 making direct contact with the wipe W, such as a sprayer, drip, atomizer, or other indirect application mechanism. FIGS. 11A-11G show implementations of devices incorporating non-contact style applicators. Each of the implementations will be described in more detail below. As mentioned above, in certain implementations the device may include at least two reservoirs 414 or a single reservoir 414 divided into at least two separate chambers which hold volumes of different compositions which may include, for example, two solutions which when applied to the wipe by actuation of the device form the indicator composition in situ on the wipe; or a indicator composition and a disinfectant composition which are both applied simultaneously to the wipe by actuation of the device. In accordance with these implementations, the applicator 429 may be configured to apply an amount of at least two different compositions to the wipe. For example, the direct contact style applicator may be in the form of at least two rollers, brushes, ball-bearing devices, or other contact elements known in the art, such that each contact element is adapted to deliver an amount of a different composition to the wipe. Preferably, the applicator 429 is in the form of two rollers. Similarly, the non-contact style applicator may include at least two sprayers, drips, atomizers, or other indirect application mechanisms configured to apply an amount of at least two different compositions to the wipe.

As will be described in more detail below, in some implementations, the disclosure provides multi-component indicator compositions which provide for improved point of use disinfection by keeping separate until point of use actuation of a device as described herein certain components that when combined become unstable. For example, unstable components may be stored within separate compartments of the reservoir 414 of the cartridge 413 in their stable form and combined at the time of use to provide higher potency without the drawbacks of instability.

The reservoir 414 can be divided into two, three, four, or more separated chambers within the cartridge 413. The number of chambers can vary and may depend upon the number of components and the need to keep certain components physically separate from one another prior to use by application to a surface. It should be appreciated that the cartridge 413 may have more reservoirs 414 than is used at any particular time. For example, a cartridge 413 may have four reservoirs 414, but only three reservoirs 414 are needed to formulate an appropriate disinfecting wipe.

In some implementations, the cartridge 413 can be a single chamber cartridge containing a single liquid composition, such as a single component indicator composition or disinfectant composition as described herein, or other composition as described above. Alternatively, the cartridge 413 can be divided into two or more chambers 414 containing two or more components of a multi-component liquid composition, such as a multi-component indicator composition as described herein. In some implementations, the dispensing cartridge 413 can be divided into more than two chambers 414, including three or more chambers 414, each of the plurality of chambers 414 containing a different component of a multi-component composition and separated from each other such that no pre-mixing of the separate components occurs.

In some implementations, each of the chambers can be associated with its own nozzle for dispensing its contents. As such, the device 400 can include more than a single applicator 429 for each chamber. A dual-chambered reservoir 414 can have two applicators 429, a tri-chambered reservoir 414 can have three applicators 429, and so on. Alternatively, a single applicator 429 can be configured to deliver the contents of each of the chambers. For example, a single nozzle can articulate relative to an outlet from each reservoir chamber 414. The single nozzle can move to the outlet to dispense solution from the first reservoir chamber 414 before moving to a second chamber outlet to dispense solution from the second reservoir chamber 414, and so on. The applicator(s) 429 can dispense these solutions at appropriate volumes for the end use. For example, a first applicator 429 can dispense a first volume of fluid from the first reservoir chamber. A second applicator 429 can dispense a second volume of fluid from the second reservoir chamber. The second volume of fluid can be the same or different from the first volume of fluid. As described elsewhere herein, the first and second applicators 429 can be dedicated applicators for their particular reservoir chamber to avoid intermixing of solutions and inadvertent chemical reactions from occurring within the device 400. A single applicator 429 can be programmed to dispense the appropriate fluid volume from each reservoir chamber depending on its contents. To provide an example of the combinations of solutions and volumes, the first volume dispensed can be 1 mL of bleach and the second volume dispensed can be 9 mL water to create a 1:10 dilution for bleach disinfection. It should be appreciated that any number of combinations of solutions and volumes are considered herein and this is provided as an example.

In an implementation, each reservoir chamber incorporates a separate, dedicated applicator 429. Each applicator 429 can be programmed to dispense to a particular region of a wipe rather than directly on top of the same part of the wipe. Thus, the applicators 429 can be arranged to dispense in parallel, in series, or in combinations of both. In an implementation, the applicator 429 is a sprayer having a nozzle as described elsewhere herein. The applicator 429 can include a plurality of nozzles arranged to dispense according to a particular pattern. The plurality of nozzles can be arranged in pairs, 3 to a row, 4 to a row, 4 to a column, a grid of 2×2 nozzles, 3×2 nozzles, etc. The plurality of nozzles can be arranged according to a shape such as a rectangle, diamond, pentagon, hexagon, heptagon, octagon, circle, etc. Any desirable nozzle configuration may be designed and used to dispense the solutions from the chambers.

Additionally, the plurality of nozzles can be configured to dispense their respective solutions at different times. A first nozzle can dispense from a first chamber for a first time (e.g. 0.5 seconds) and a second nozzle can dispense from a second chamber for a second time, where the times are the same or different. The nozzles can be configured to dispense simultaneously or in series. For example, the first nozzle may dispense for a first period of time after which a second nozzle is activated to dispense for a pre-determined time. Each nozzle can be configured to dispense at different times and for different lengths of time. For example, a first nozzle can dispense a solution for 1 second, pause for a pre-determined time, and then may dispense for 1, 2, 3, or more additional seconds.

The plurality of nozzles can be configured to spray their respective solution in a spray, fine mist, thick stream, or otherwise. The configuration of application provided by the plurality of nozzles can be due to orifice size, flow rate, pressure, and/or orifice shape. It should be appreciated that the various configurations of dispensing fluid can be due to the programming of the computing system 495 and can be optimized, customized, or otherwise adjusted based on the desired result.

In still further implementations, the device 400 can incorporate a mixing chamber such that the solutions from different chambers can be mixed together prior to be dispensed. The mixing chamber can be near an area where the solutions from the chambers can combine. In some implementations, the mixing chamber can be positioned within a region of the cartridge 413. The mixing chamber can include a mixing mechanism such as a stir bar or other movable component to ensure the solutions combined within the mixing chamber are more homogenously dispensed. In some implementations, the nozzle can communicate with the mixing chamber to dispense the mixed solutions. In some implementations, the mixing chamber can be positioned within the device 400 such that a wipe can be pulled through the mixing chamber to be soaked with the mixed solution rather than sprayed or pumped out of the mixing chamber onto the wipe.

Again with respect to FIGS. 4E-4F, the reservoir 414 of the cartridge 413 can be pre-filled prior to use with a single or multi-component liquid composition, such as an indicator composition and/or a disinfectant composition as described herein, or other composition as described above. The cartridge 413 can be a single-use disposable element or can be refilled upon emptying. The cartridge 413 can be filled in various ways such as a septum or other feature configured to be penetrated or opened for filling. For example, the cartridge 413 can be filled through the septum of the coupling feature 439. The volume of the reservoir 414 contained within the cartridge 413 can vary, but generally, the volume is sufficient to accommodate the number of wipes A provided by a single canister C. The cartridge 413 can include a fill line or other metering system 411 (see FIG. 11B) visible from an exterior of the device 400 so a user can easily ascertain the remaining volume of the composition in the reservoir 414 of the cartridge 413. In some implementations, the side wall 421 of the housing 412 can have a cut-out 448 or other feature that reveals an outer wall of the cartridge 414 through the cut-out 448 from outside the housing 412 when the cartridge 413 is positioned within the slot 437. The cartridge 413 can include a lip 443 near the top that facilitates pulling the cartridge 413 out of the slot 437. The shape of the cartridge 413 can vary, but generally the cartridge 413 is shaped to conform to the overall shape of the housing 412 when engaged with the slot 437. The cartridge 413 can include mechanical interlocking features such that the device 400 can only be used with a specific cartridge 413 keyed to connect with the device 400. The cartridge 413 can include a data element 424 or an encoder strip such as a bar code, QR code, RFID chip, or other feature that allows the cartridge 413 to be scanned and read by a reader device. The reader device can be a separate device or a part of the device 400. The element 424 can also for a user to assess information about the cartridge 413 as will be described in more detail below.

The cartridge 413 can also include more than a single reservoir 414. For example, the cartridge 413 can include multiple reservoir chambers within a single cartridge 413. The different reservoir chambers can be formed by one or more septa or inner walls extending within the interior of the cartridge 413 separating the interior into individual reservoir chambers configured to contain the different components of a multi-component indicator composition, a single component indicator composition, and/or a disinfectant composition and one or more optional additives, such as a surfactant. The different compositions, and/or components and/or additives can then be dispensed simultaneously from their respective chambers.

The reservoir 414 and the application mechanism 418 are arranged to work in concert to apply an amount of a liquid composition, such as the disinfectant composition and/or indicator composition described herein, or other composition as described above, which is stored within the reservoir 414 to a wipe W as it is dispensed from its canister C through the dispensing aperture 416 of the device 400. As with respect to other implementations described herein, the wipe W can be dispensed from the device 400 manually such as by a user pulling the wipe W through the dispensing aperture 416 in the top surface 419. The wipe W may also be dispensed through the device 400 by an automatic feed system that includes a powered motor. The application mechanism 418 of the device 400 can include a transfer element 427 and at least one applicator 429. The transfer element 427 is configured to transfer an amount of a liquid composition, such as the disinfectant composition and/or indicator composition described herein, or other composition as described above, from the reservoir 414 to the applicator 429, which in turn is configured to apply an amount of the composition to the wipe W dispensed through the dispensing aperture 416 of the device 400. The transfer element 427 drives the amount of composition in a direction towards the applicator 429. The transfer element 427 can create a pressure differential between the inside of the reservoir 414 where the composition is stored and a region outside the reservoir 414. The pressure differential can be created by the transfer element 427 due to creation of a positive pressure within the reservoir 414 pushing the amount of composition towards the applicator 429. The pressure differential can be created by the transfer element 427 due to creation of a negative pressure outside of the reservoir 414 pulling the amount of composition towards the applicator 429. The transfer element 427 can create the pressure differential by a pumping action, either a manual pumping action or by an electric- or battery-powered motor to create the pumping action. In some implementations, a battery can be coupled to the cartridge 413 and/or the reservoir 414 contained in the cartridge 413 to drive a motor to create the pumping action. In the case of a manually-created pumping action, the transfer element 427 can include a trigger, button, actuator, or other manual input 431 that creates the pressure differential relative to the interior of the reservoir chamber 414 directly when pressed, squeezed, or otherwise manually actuated. In some implementations, the transfer element 427 can include a pumping element 463 that is electrically-powered by a motor to create the pressure differential relative to the interior of the reservoir chamber 414 upon actuation of a trigger, button, or other input, which will be described in more detail below.

The actuators described herein for dispensing the liquid composition can be a dispense button that is easy to actuate and well within view of a user. The button can have a particular distinguishing color, such as blue where the remainder of the device is primarily another color. It should be appreciated that the inputs for dispensing the liquid composition can be a mechanical button or actuator that causes movement of another component of the device. The actuator may also be an electrical input that causes dispensing by communicating a signal to a controller as will be described elsewhere herein. Reference to an actuator or an input is not intended to be limiting and may be used interchangeably.

The actuator 431 can cause the transfer element 427 and the applicators 429 to engage such that a liquid composition, such as the disinfectant composition and/or indicator composition described herein, or other composition as described above, can be applied to the wipe W being dispensed through the device 400. The configuration of the at least one applicator 429 of the application mechanism 418 can vary. The applicator 429 can apply the liquid composition to the wipe W by directly contacting the wipe W. In this implementation, the applicator 429 can be one or more rollers, brushes, ball-bearings, or other direct contact element known in the art. The one or more applicators 429 can also include a sprayer, or other non-contact configuration, which will also be described in more detail below. The transfer element 427 and applicators 429 work in concert with one another and with the reservoir 414 to control flow of the composition from the reservoir 414 to the wipe W.

Figure 7A:
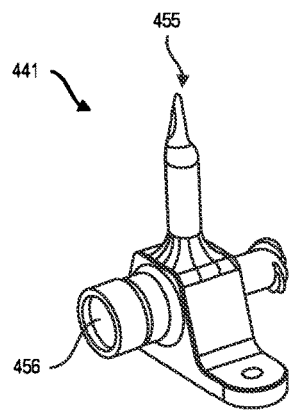
FIGS. 7A-7C are various views of a pneumatic tap of the device of FIG. 4A.
Figure 7B:
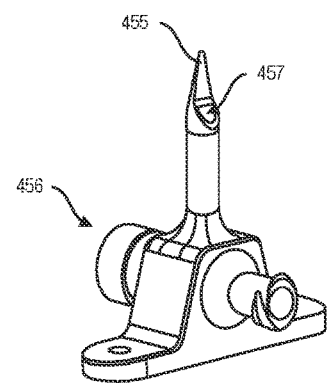
Figure 7C:
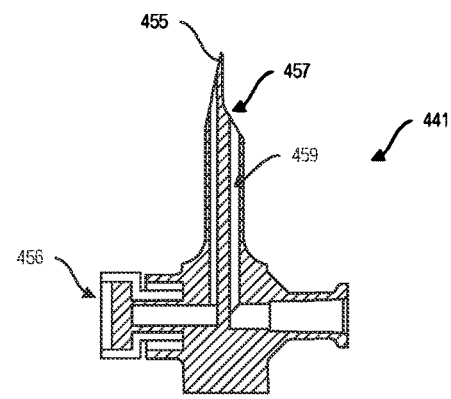

As mentioned above, the slot 437 within which the cartridge 413 is received by the housing 412 can include a coupling feature 441 configured to penetrate a lower end region of the cartridge 413. As best shown in FIGS. 7A-7C, the coupling feature 441 can be a pneumatic tap 455 having an end configured to penetrate the coupling feature 439 of the cartridge 413. The tap 455 can include at least one opening 457 into a lumen 459 extending through the tap 455 such that when the tap 455 inserts through the septum of the coupling feature 439 on the cartridge 413, the interior of the reservoir 414 is put into fluid communication with the lumen 459 of the tap 455 through the at least one opening 457. The lumen 459 of the tap 455 is configured to be in fluid communication with a conduit 461 leading to the applicator 429. A pumping element 463 (which can be part of the transfer element 427) can be activated to urge the liquid composition from the reservoir 414 towards the applicator 429 through the conduit 461, for example due to creation of a pressure differential relative to the reservoir 414. The pumping element can urge fluid from the reservoir 414 by positive and/or negative pressure.

The tap 455 can also include a vent 456 or other feature to allow equilibration of pressure within the reservoir 414 upon displacement of fluid by the pumping element 463 (see FIGS. 7A-7C). A vent 491 can additionally be positioned within a region of the cartridge 413 (see FIGS. 12A-12E). The vent 491 can incorporate a one-way valve that allows equalization of pressure on either side of the valve. In some implementations, the valve is a duckbill valve configured to break open upon generation of a certain threshold amount of negative pressure within the reservoir 414 placing the interior of the reservoir 414 in fluid communication with the atmosphere. The vent 491 prevents the creation of a vacuum within the reservoir 414.

Figures 8A, 8B:
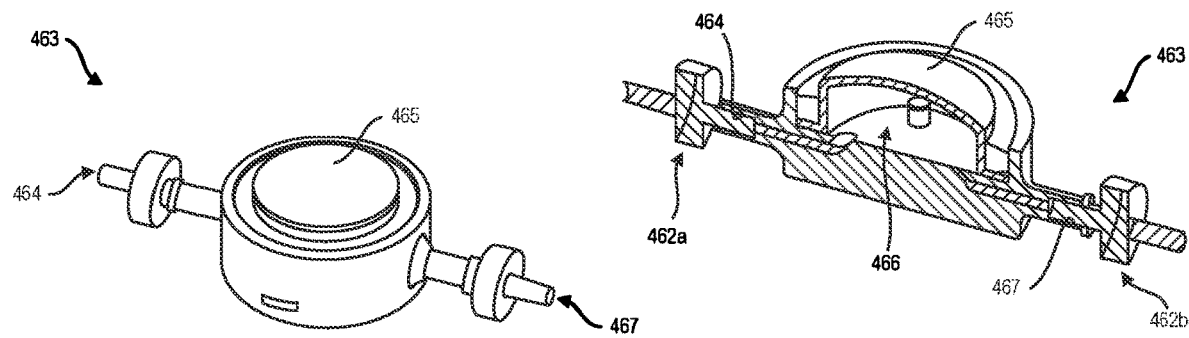
FIGS. 8A-8B are perspective and cross-sectional views, respectively, of the pumping element of the device of FIG. 4A.

The configuration of the pumping element 463 can vary. The pumping element 463 can be a positive displacement, reciprocating, rotary, piston, diaphragm, peristaltic, dynamic, centrifugal, hydraulic, valved-gravity feed, or other pump type. In some implementations, the pumping element is a peristaltic pump. The peristaltic pump can provide a quieter and more durable operation that is resistant to clogging and drips. The pumping element 463 can urge fluid from the reservoir 414 by positive or negative pressure. The pumping element 463 can incorporate a dosed valve that allows for gravity feed of the liquid composition towards the applicator 429. FIGS. 8A and 8B illustrate one implementation of a pumping element 463 that can cause fluid displacement from the reservoir 414 towards the applicator 429.

Figure 9:
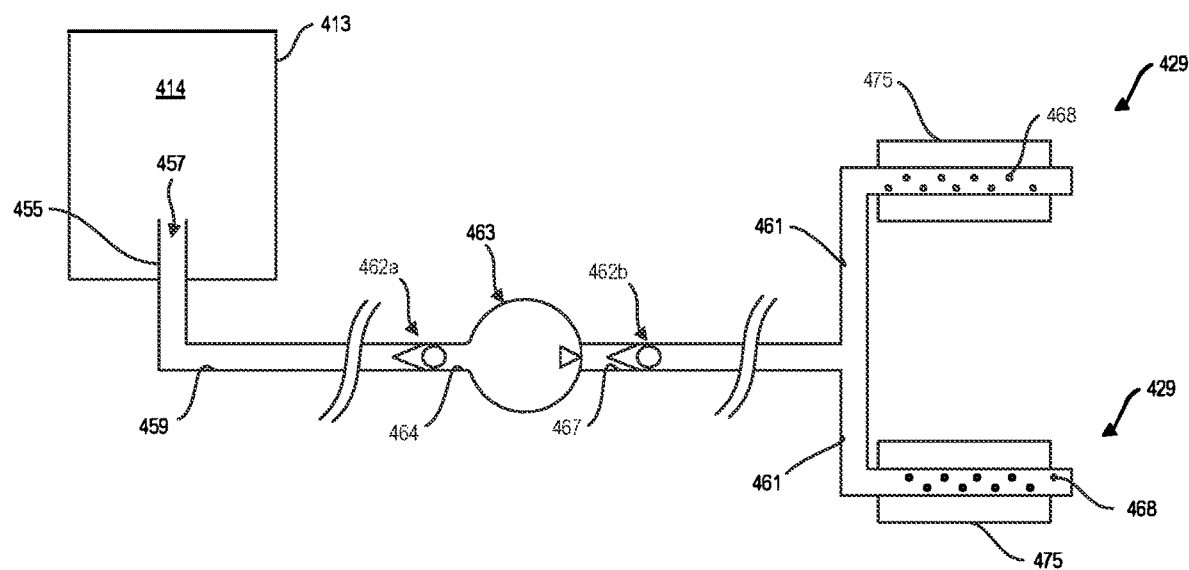
FIG. 9 is a schematic of the fluid flow through the device of FIG. 4A.

In some implementations, the pumping element 463 can include a diaphragm 465, an internal chamber 466, an inlet conduit 464 leading toward the internal chamber 466, and an outlet conduit 467 leading from the internal chamber 466. The pumping element 463 can include a one-way valve 462a upstream from the internal chamber 466 within the inlet conduit 464 as well as a one-way valve 462b downstream from the internal chamber 466 within the outlet conduit 467 (see FIG. 9). The one-way valves 462a, 462b can ensure unidirectional fluid flow from the reservoir 414 towards the applicator 429. The configuration of the valves 462a, 462b can vary. In some implementations, the valves 462a, 462b are check valves. The cartridge 413 can be coupled to the device 400 such that the lumen 459 of the tap 455 is placed into fluid communication with the interior of the reservoir 414 via opening 457. As the diaphragm 465 of the pumping element 463 is displaced inward, a pressure differential is created that draws fluid from the reservoir 414 into lumen 459 via the opening 457. The fluid is directed past one-way valve 462a into the inlet conduit 464 leading to the internal chamber 466 of the pumping element 463. Fluid is ejected from the internal chamber 466 through outlet conduit 467 past one-way valve 462b toward conduit 461 leading to the one or more applicators 429. The applicator 429 can include at least one outlet 468 through which the amount of the liquid composition displaced from the reservoir 414 is released.

In other implementations, the pumping element 463 can include a manual spray mechanism that pumps the liquid composition from the reservoir 414 towards the applicator 429 by user depression of the actuator 431, such as like a manual spray bottle mechanism (see FIG. 12E). For example, a user pushing on the actuator 431, such as a lever or other manual mechanism, can trigger the sprayer applicator 429 mechanically that pumps/sprays the indicator solution from the reservoir 414 onto the wipe W. Additional pushes of the actuator 431 result in additional amounts of the liquid composition being transferred and applied as it is pulled out from the upper surface 419 or side surface 421.

Figure 10:
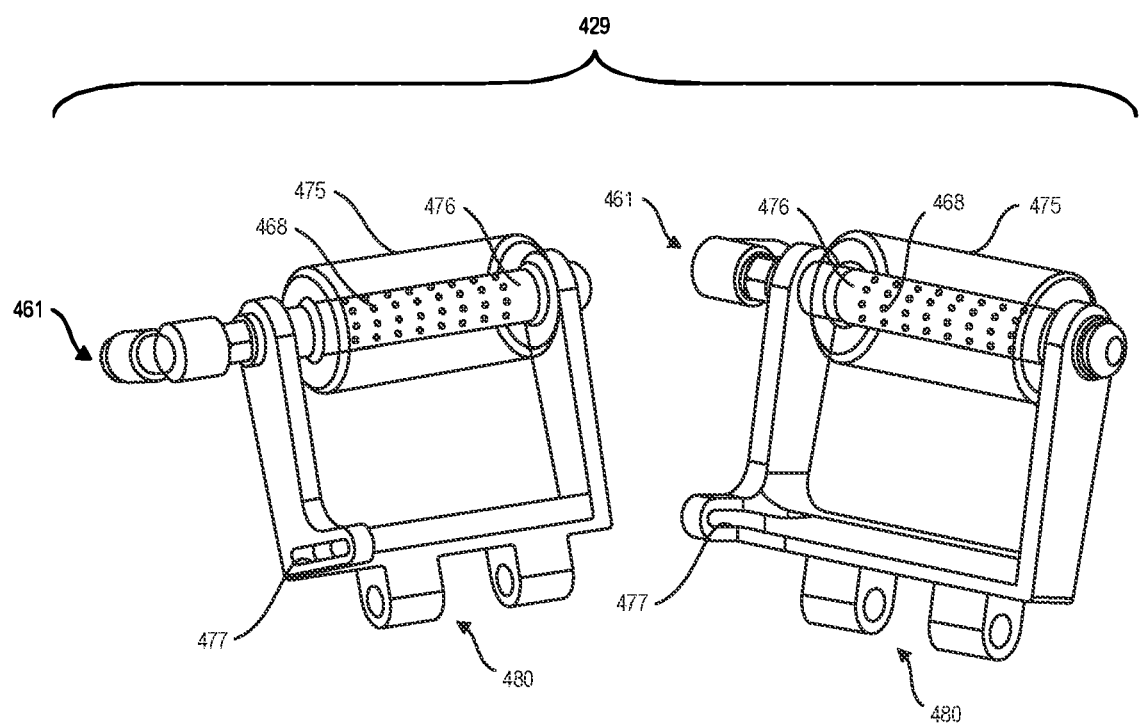
FIG. 10 is a perspective view of a pair of applicators of the device of FIG. 4A.

The one or more applicators 429 of the device 400 can allow for one-sided or two-sided application of the liquid composition to the wipe W. In some implementations, the device 400 can include a pair of applicators 429 (see FIG. 10). The pair of applicators 429 allows for two-sided application of the composition to the wipe W. Each applicator 429 can include a roller 475 near an upper end and a hinge element 480 at a lower end. The hinge element 480 allows the applicator 429 to be moved as will be described in more detail below. In some implementations, the hinge element 480 can be shoulder bolts and include a pair of knuckles configured to receive a pin. The roller 475 can surround an inner shaft 476 through which the conduit 467 extends leading to the one or more outlets 468 formed in a wall of the inner shaft 476. As the liquid composition is directed through the conduit 467 and out the outlets 468, the material of the roller 475 is saturated with the liquid composition. The material of the roller 475 can vary. Generally, the material has wicking and transfer properties and is relatively durable. The material can be relatively durable even in oxidizing or reducing environments such as in the presence of bleach. The material can have a relative high coefficient of friction with the wipe W. The material of the roller 475 can include foam rubber, knit, sponge formed of one or more of melamine-, polyester-, polyurethane-, polyimide-, polyethylene-, vinyl-, and polyolefin-based materials. The material of the roller 475 can include Essentra PT X-6981C, Essentra Cloth, CAPUCELL, and Magic Sponge. The material of the roller 475 can include ethylene propylene diene monomer (EPDM) foam rubber as well as various other foams such as polyimide foam, polyethelene foam, vinyl foam, Viton foam, silicone foam, ionomer foam, natural gum foam, ECH foam, and neoprene. The material of the roller 475 can include cellulose sponge and polyester wrapped fibers. The material of the roller 475 can include a coating to improve its transfer and wicking properties such as a hydrophilic coating. In some implementations, the material of the roller 475 is EPDM with a hydrophilic coating. In some implementations, the roller 475 can be a two-part roller in which an inner core of highly absorbent material, such as foam, is wrapped with a thin cloth-like material that can transfer fluid well while being very durable and have a coefficient of friction that is higher than a coefficient of friction of the wipe W.

Figure 4I:
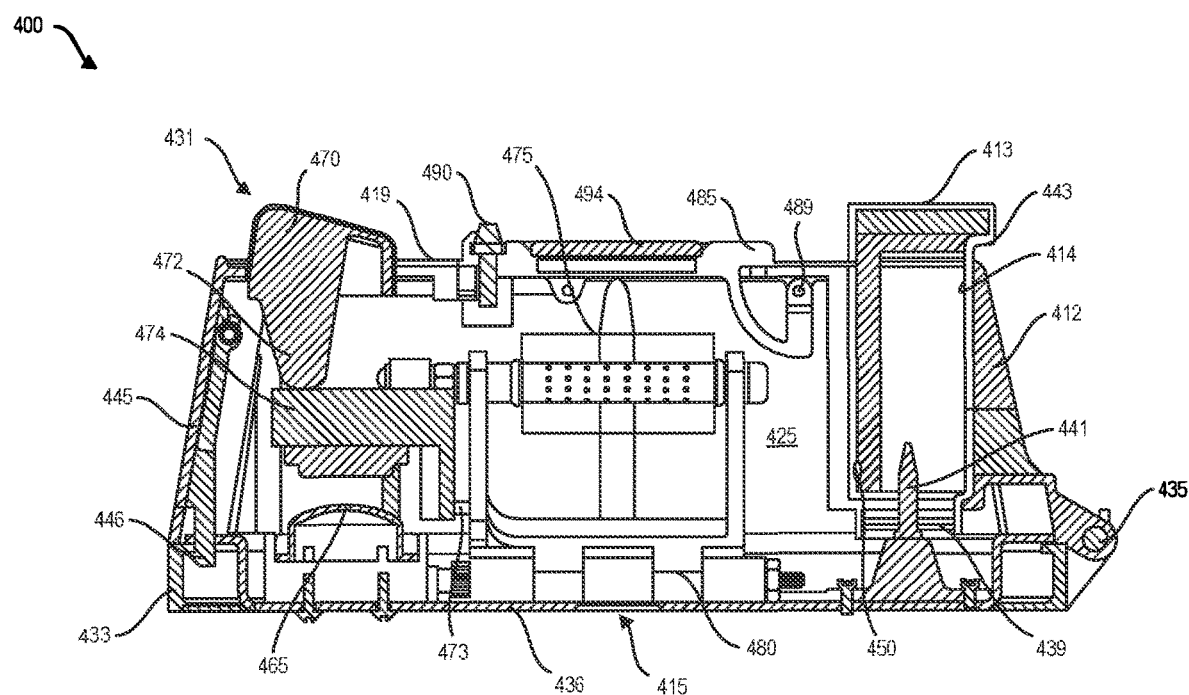
FIGS. 4I-4K are cross-sectional views of the device of FIG. 4A.
Figure 4J:
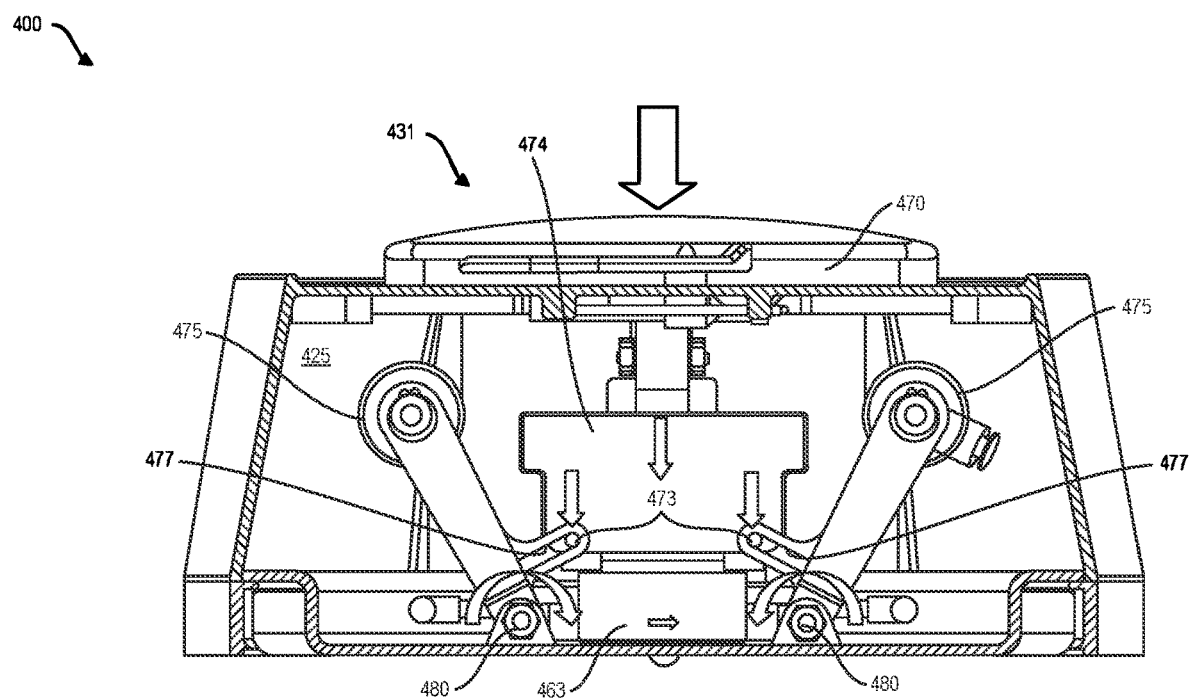
Figure 4K:
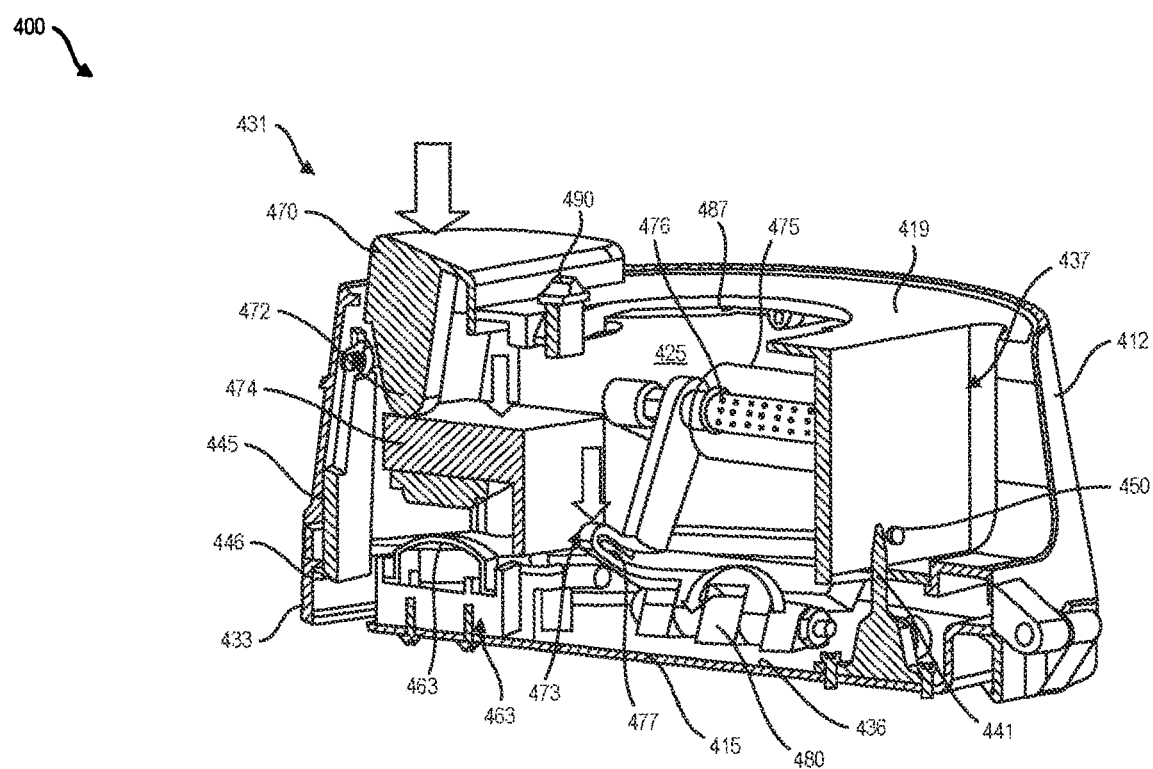

As described above, actuating an input of the device 400 can simultaneously activate or move the applicators 429 and activate the transfer element 427 to pump fluid toward the applicators 429. The mechanism by which the actuator 431 engages the transfer element 427 and applicators 429 can vary. In some implementations and as shown in FIGS. 4I-4K, the actuator 431 can be mechanical and have an outer portion 470 that extends outside the interior 425 of the housing 412, such as through the upper surface 419 of the housing 412, and an inner portion 472 that resides within the interior 425 of the housing 412. The actuator 431 can be biased in an upward position. The actuator 431 returns to its initial upward position after being depressed by a user to a downward position and released. The inner portion 472 of the actuator 431 can lie adjacent to a slider 474 that engages both the applicators 429 and the pumping element 463. The actuator 431 is urged against an upper surface of the slider 474 or otherwise moves the slider 474 when it is depressed by a user. The slider 474 can be coupled to the applicator 429 so that the actuator 431, the slider 474, and the applicator 429 move in concert with one another. The slider 474 also activates the pumping element 463 as it is moved. This arrangement moves the rollers 475 together and pumps fluid towards the applicator 429 with a single depression of the actuator 431. It should be appreciated that the activation of the applicators 429 and/or transfer element 427 need not be mechanical and can incorporate electrical circuitry to activate the various components of the device 400, as described in more detail below.

In some implementations, the slider 474 has a pin 473 configured to insert through and slide within an elongate slot 477 of the applicator 429 (see FIGS. 4I-4K). As mentioned above, each applicator 429 can include a roller 475 at an upper end and a lower end movably coupled to the plate 436 by a hinge element 480. The pair of applicators 429 can be coupled to the plate 436 on opposite sides of the internal opening 415 through which a wipe W can extend into the interior 425 of the housing 412. The applicators 429 are movably coupled to the plate 436 via their hinge element 480. The rollers 475 can be moved in a rocking motion toward and away from each other depending on whether the actuator 431 is depressed. The actuator 431 and the applicators 429 are biased into a first position where the actuator 431 is urged upward and the rollers 475 are angled outward and separated a distance away from one another. Upon depressing the actuator 431, the inner portion 472 of the actuator 431 is urged downwards against the slider 474, which in turn moves it downwards. The pin 473 slides within the slot 477 of the applicator 429 as the slider 474 is urged downwards. This causes the applicators 429 to rock from the first position in which the rollers 475 are angled outward away from one another to a second position in which the rollers 475 rock towards one another above the opening 415. As described above, the wipe W extends from its canister C through the opening 415 into the interior 425 of the device 400. The rollers 475 rocked into the second position thereby contact the wipe W therebetween in order to transfer or imbue the liquid composition onto the wipe W as the wipe W is advanced past the rollers 475. The actuator 431 is depressed as the wipe W is advanced through the interior 425 and out the dispensing aperture 416. A single wipe W can be advanced or multiple wipes A can be advanced with a single actuation of actuator 431. As mentioned elsewhere herein, the wipe W can be advanced manually such as by pulling action or can be advanced by a power feed system, which will be described elsewhere herein. In addition to causing the rollers 475 to rock towards one another, the movement of the actuator 431 and thus, the slider 474 can activate the pumping action of the transfer element 427 to saturate the rollers 475 with the liquid composition stored within the reservoir 414. As mentioned above, the transfer element 427 can include a pumping element 463. In some implementations, the pumping element 463 is a diaphragm pump positioned underneath the slider 474. As the slider 474 is moved downwards and urges the rollers 475 towards one another, the underside of the slider 474 is simultaneously urged against a diaphragm 465 (or otherwise activate the pumping element 463 if another type of pumping element 463). This generates a pressure differential causing fluid to be displaced from the reservoir 414 into the conduit 461 towards the rollers 475 of the applicators 429, which are being rocked towards one another to grab the wipe W therebetween.

As mentioned above, hinging at least a portion of the device 400 into an opened position may be helpful when a user needs to assist with priming the first wipe W into the device 400. For example, the lead wipe W in the canister C may be primed or engaged with the device 400 by unlocking the release button 445 to expose at least a region of the interior 425. Upon unlocking the release button 445, the upper portion 417 of the housing 412 can be opened by rotating it around the hinge element 435 exposing the opening 415 in the plate 436. The lead wipe W of the interconnected sheets in the canister C can be pulled through the opening 415 into the interior 425 of the housing 412. The lead wipe W is then threaded through the interior 425 such that the wipe W is brought into proximity with the applicator 429 of the application mechanism 418 (e.g. rollers or sprayer in the case of non-contact applicator). Threading the lead wipe W through the opening 415 can help to limit the angle at which the wipe W is positioned between the applicators 429, such as the rollers 475 of the applicators 429. The lead wipe W can be thread up between the pair of applicators 429 without coming into direct contact with the rollers 475. The leading edge of the lead wipe W is inserted then through the dispensing aperture 416. The locking element 490 can help thread the first or lead wipe W into the cap 485. After the lead wipe W is primed, the locking element 490 need not be used again until all the wipes W in the canister C are depleted and a new lead wipe W is to be primed. In other implementations, the lead wipe W can be threaded through the plurality of guide rollers 538 so that the wipe W is brought into proximity with the applicator 429 of the application mechanism 418 by threading the wipe W through the plurality of guide rollers 438 so that the wipe W lies horizontally underneath the flow diverter 469 such that the diverter directs the solution onto the wipe W (see FIG. 11D). The leading edge of the lead wipe W is inserted then through the dispensing aperture 416.

As mentioned above, the devices described herein can include applicators configured to apply the amount of the liquid composition transferred by the transfer element to the wipe dispensed through the device. The configuration of the applicators can vary depending on whether the applicator contacts the wipe directly or avoids coming into contact with the wipe. Described above are applicators that apply a liquid composition to the wipe by directly contacting the wipe such as with a roller, brush, ball-bearing, or other direct contact device. In an interrelated implementation, the applicator can apply a liquid composition to the wipe without the applicator making direct contact with the wipe, such as with a sprayer head as will be described in more detail below. It should be appreciated that features described above in the context of the contact applicator devices can also be incorporated, where appropriate, with the non-contact applicator devices.

FIGS. 11A-11G illustrate an interrelated implementation of a device having a non-contact applicator or an applicator configured to apply the amount of a liquid composition to the wipe without directly contacting the wipe. As with other implementations described herein, the device 400 can include a housing 412 having a dispensing aperture 416 and an application mechanism 418.

In the implementation shown in FIGS. 11A-11G the dispensing aperture 416 is shown in a side surface 421 of the housing 412. A lower end region 423 of the housing 412 can define an internal aperture or opening 415. When the housing 412 is coupled to a region of a canister C of wipes W, the wipe W stored within the interior of the canister C can be drawn into the interior 425 of the housing 415 through the opening 415. The wipe W can be fed through the interior 425 towards the dispensing aperture 416 in the housing 412.

The device 400 can include a dispensing mechanism 430 that is an automatic dispensing mechanism or manual. The dispensing aperture 416 for the automatic dispensing mechanism 430 can be a generally rectangular-shaped dispensing aperture 416 whereas the manually dispensed configuration may incorporate a zig-zag shaped dispensing aperture 416 although it should be appreciated that other shapes can be used. The dispensing aperture 416 can include a cover 494 positioned over the dispensing aperture 416 to avoid inadvertent drying out of the wipes W in their canister C and within the device 400 (see FIG. 11E). The cover 494 can be hinged such that the cover 494 can be manually or mechanically opened.

The cover 494 can include a spring-loaded hinge that opens when an actuator is pushed. The actuator 431 can simultaneously release the cover 494, activate the transfer element 427 to pump a liquid composition towards the applicator 429, and activate the applicator 429 to apply the transferred a liquid composition to the wipe A. The actuator 431 can also simultaneously activate any gripper, pincher elements 432 so that the saturated wipe W is released and ready for use. The cover 494 can also automatically close (and the gripper automatically released) when the actuator 431 is released to prevent the wipes W within the canister C from drying out. Consolidating the activation of the various mechanisms into a single actuation simplifies use of the device 400 such that it can be used with a single hand. It should be appreciated, however, that the various components can also include their own actuator and/or be configured for manual use.

The one or more applicators 429 of the device 400 can allow for one-sided or two-sided application of the liquid composition to the wipe W. The applicator 429 can include a conduit 461 having at least one outlet 468 through which the amount of the liquid composition displaced from the reservoir 414 is released through the applicator 429. The applicator 429 can include any of a variety of sprayers, including the liquid sprayers described in U.S. Pat. No. 8,602,386, WO 2006/101730, and WO 2009/085175, which are each incorporated by reference herein.

The applicator 429 can be arranged relative to the dispensing aperture 416 such that spray from the outlet 468 can be directed toward the wipe being dispensed through the dispensing aperture 416. In some implementations, the applicator 429 includes a spray diverter 469 positioned across from the outlet 468. The spray diverter 469 can include a surface shaped to re-direct the sprayed composition exiting from the outlet 468 onto a surface of a wipe W being dispensed or fed through the dispensing aperture 416. In some implementations, the spray diverter 469 is arranged above the wipe W such that the spray diverter 469 re-directs the sprayed liquid composition downward onto an upper surface of the wipe W. The surface of the spray diverter can re-direct the sprayed liquid composition directly onto the wipe W or at an angle such as by incorporating a spray diverter 469. The spray diverter 469 can allow for an even distribution of the liquid composition onto the wipe W. The spray diverter 469 can re-direct the sprayed composition along any number of angles such that it drips down onto the wipe W. In some implementations, the angle of re-direction is between 45 degrees and 90 degrees relative to an axis of the spray discharge from the outlet 468. In other implementations, the angle of re-direction is less than 45 degrees relative to an axis of the spray discharge or greater than 90 degrees relative to an axis of the spray discharge from the outlet 468. The spray diverter 469 can have a curved surface configured to receive a liquid composition from the outlet 468 against an upper region of the curved surface such that the liquid composition drips down or waterfalls along the curved surface onto the wipe W to achieve a more even distribution than could potentially be achieved by spraying directly onto wipe W. In other embodiments, outlet 468 can be coupled with a diffuser to achieve a more even distribution with or without spray diverter 468. The upper surface of the wipe W and the applicator 429 can be positioned generally parallel to each other and horizontal relative to the plate 436 of the device 400. An overflow container 458 can be positioned below the wipe W and sized to collect excess liquid composition that is not imbued into the wipe W.

Figure 11A:
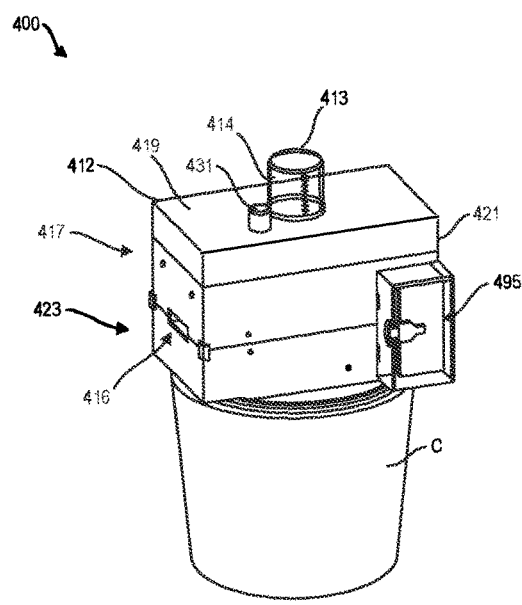
FIG. 11A is a perspective view of another implementation of a device configured to apply an indicator solution to a wipe.
Figure 11B:
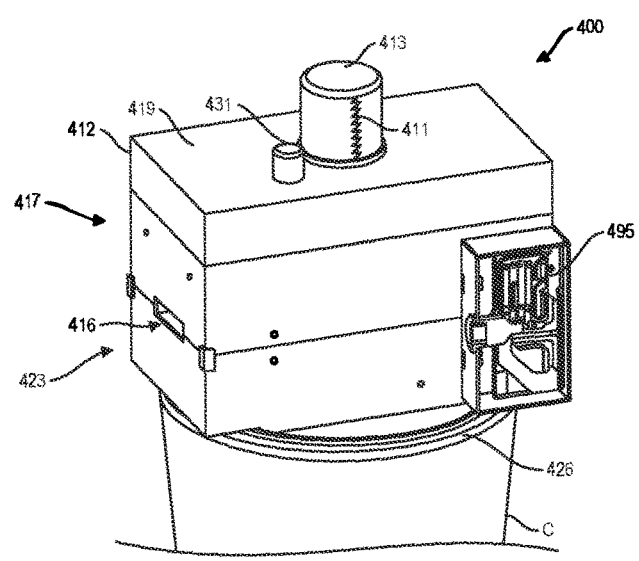
FIG. 11B is a perspective view of the device of FIG. 11A.
Figure 11C:
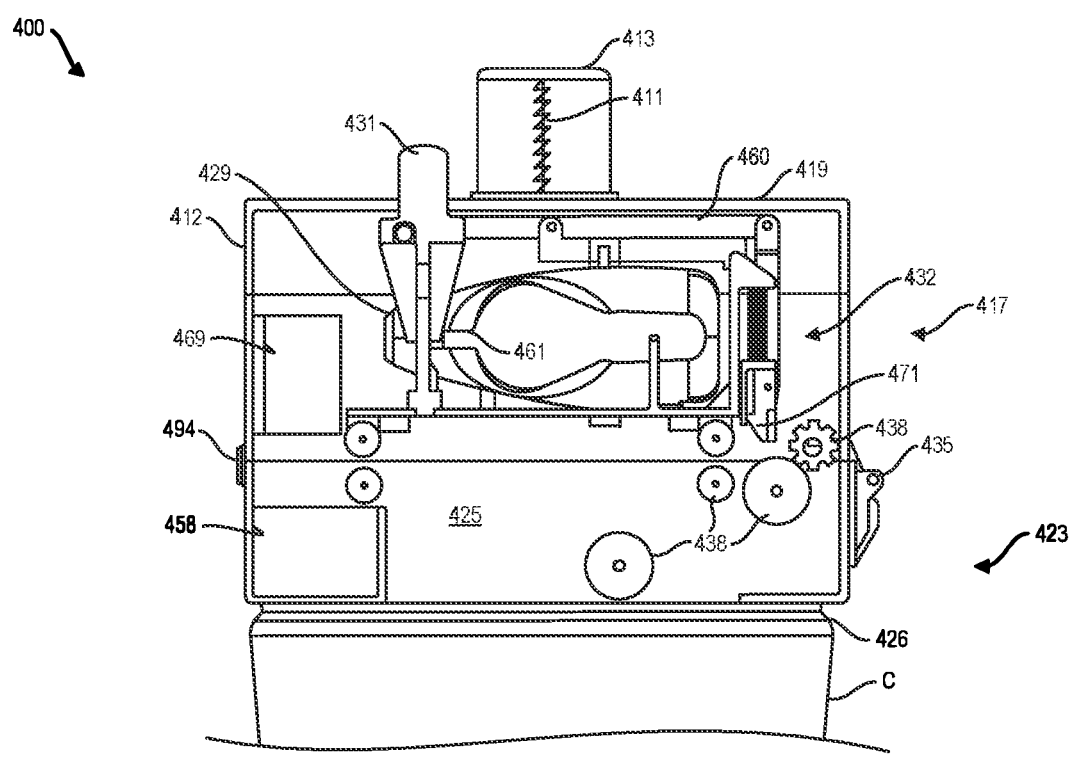
FIG. 11C is a side, cut-away view of the device of FIG. 11A.
Figure 11D:
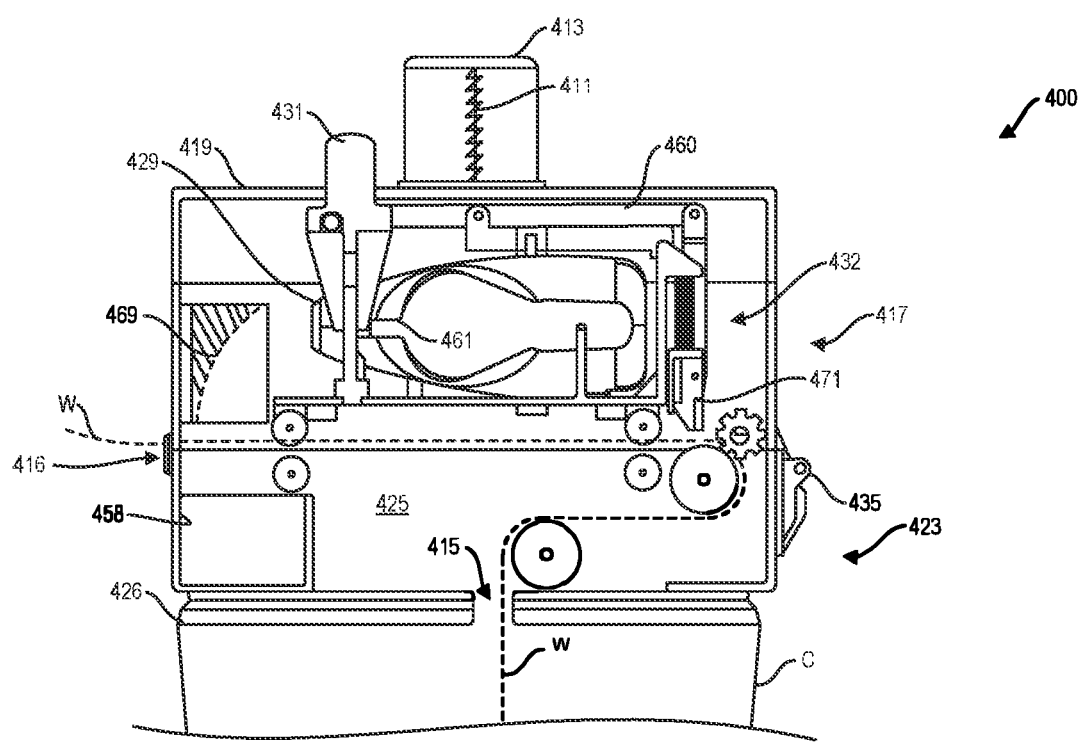
FIG. 11D is a side, cut-away view of the device of FIG. 11A showing the path of a wipe through the interior.
Figure 11E:
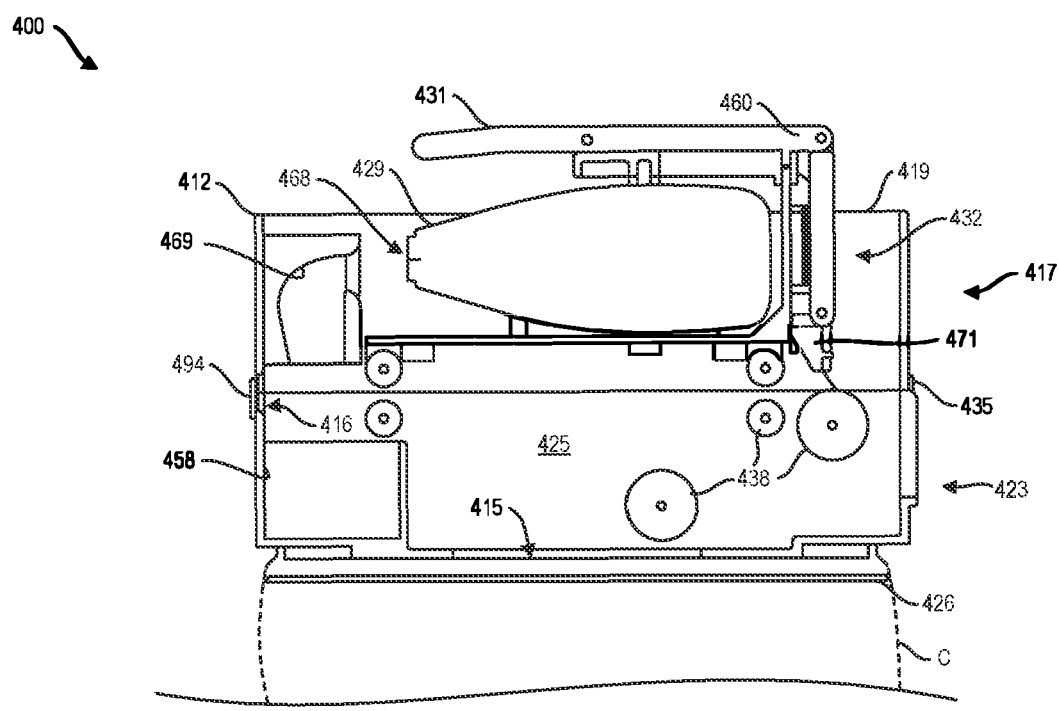
FIG. 11E is a side, cut-away view of the device of FIG. 11A incorporating an alternative actuator.
Figure 11F:
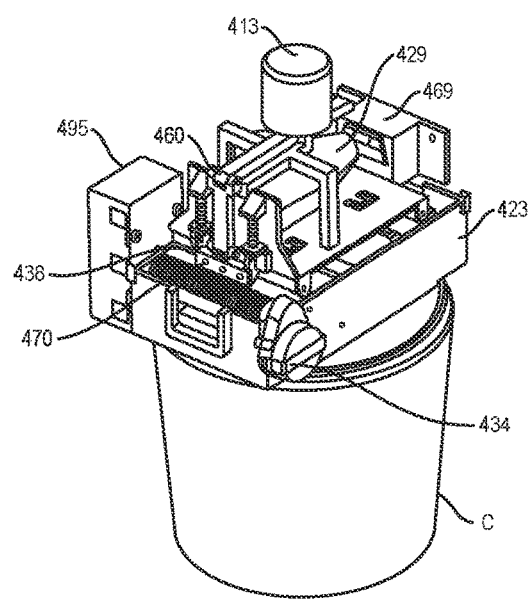
FIG. 11F is a perspective, partial view of the device of FIG. 11A.
Figure 11G:
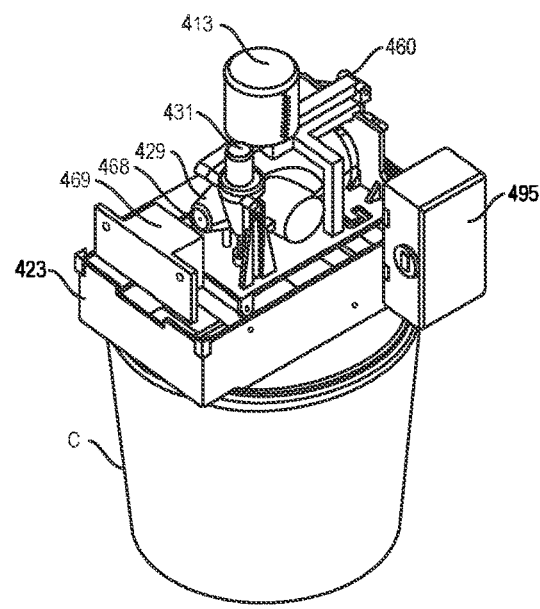
FIG. 11G is a perspective, partial view of the device of FIG. 11A.

As mentioned above, the device 400 can have a dispensing mechanism 430 that is configured for a user to manually pull the wipe through the dispensing aperture 416 and/or a dispensing mechanism 430 that includes an automatic feed system having a powered drive motor 434 and a plurality of gear rollers 438. The gear rollers 438 are configured to capture and direct the wipe W through the interior 425 of the device 400 towards the dispensing aperture 416. As shown in FIG. 11D, the wipe W can extend from its canister C through the opening 415 into the interior 425 of the device 400. At least a first gear roller 438 of the automatic dispensing mechanism 430 can contact the wipe W and direct it toward one or more additional gear rollers 438 towards the dispensing aperture 415.

The gear roller 438 can have teeth or grooves 420 for providing friction to engage with the gear driven by the motor as well as with other gear rollers 438 involved in feeding the wipe W out of the device 400. For example, FIG. 12G shows an implementation of the device 400 including a motor 434 having a gear that drives a gear roller 438. The gear roller 438 can include grooves 420. The grooves 420 provide friction with the other rollers 438 that work in coordination to dispense out the wipe W. One or more of the rollers 438 can be spring-loaded to help roll the wipes out and apply some pressure to keep the wipes stabilized as they dispense.

Figure 13A:
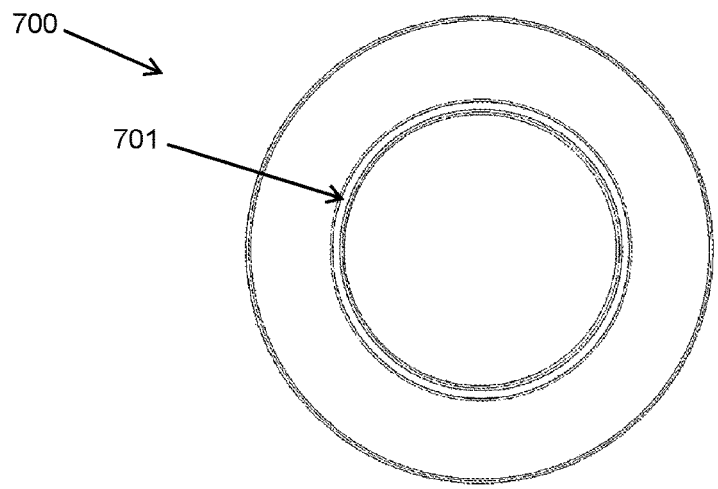
FIG. 13A-C shows top (A), side (B), and perspective (C) views of an adapter for the lid device.
Figure 13B:
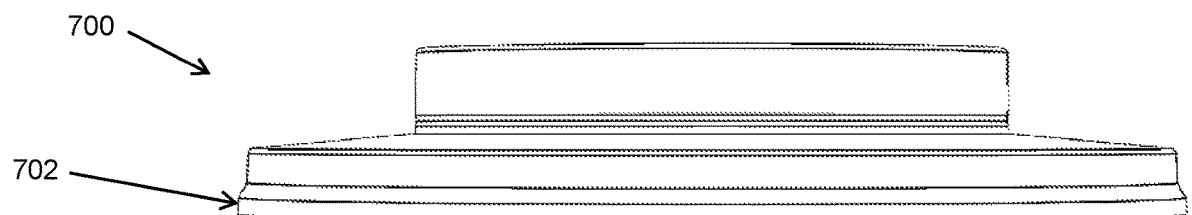
Figure 13C:
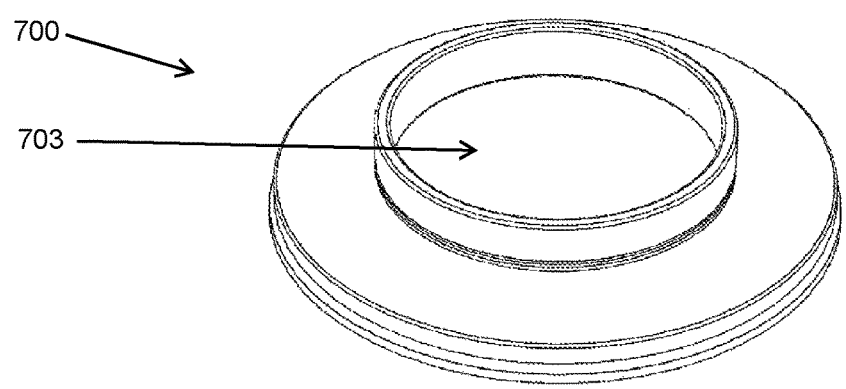

Device 400 can removably attach to adapter 700 to removably or detachably couple device 400 to a range of sizes of canister C of wipes W. The top of adapter 700 features an adapter lip 701 (FIG. 13A) where device 400 removably attaches. The bottom of adapter 700 (FIG. 13B) features an adapter lip 702 where canister C removably attaches. Adapter 700 contains an aperture 703 (FIG. 13C) through which wipes W go through to communicate with device 400.

The upper lip 701 of the adapter 700 is sized and shaped to interface with a lower end region of the device 400 housing such that the adapter 700 and the device 400 can be reversibly coupled together. For example, the inner diameter of the upper lip 701 can be sized and shaped to encircle the lower end region of the device housing. Alternatively, the outer diameter of the upper lip 701 can be sized and shaped to be received within an interior of the lower end region of the device housing. In some implementations, one or more connecting features on the lower end region of the housing of the device 400 can removably attach to the upper lip 701 of the adapter 700. Similarly, the lower lip 702 of the adapter 700 is sized and shaped to interface with an upper end region of the canister such that the adapter 700 and the canister can be reversibly coupled together. For example, the inner diameter of the lower lip 702 can be sized and shaped to encircle the upper end region of the canister. Alternatively, the outer diameter of the lower lip 702 can be sized and shaped to be received within an interior of the upper end region of the canister. In some implementations, one or more connecting features on the upper end region of the canister can removably attach to the lower lip 702 of the adapter 700. The upper lip 701 of the adapter 700 can have a first dimension and the lower lip 702 of the adapter 700 can have a second, larger dimension such that the adapter 700 can be used to connect the device 400 with larger sized canisters.

The device 400 can include one or more connecting features on the lower end region of the housing that are configured to removably couple the device to the adapter 700. The adapter 700 can include one or more sensors 705 (see FIGS. 14A-14D) configured to interface with the device 400 and/or the canister and will be described in more detail below.

Regardless whether the wipe W is advanced using a manual dispensing mechanism 430 or an automatic or powered dispensing mechanism 430, the device 400 can include one or more grippers 432. The gripper 432 allows for a user to more easily tear the wipe W after dispensing. The gripper 432 can be formed of a gripper lift arm 460 and a gripper blade 471. The gripper lift arm 460 can be spring-loaded and actuated by the actuator 431. Depressing the actuator 431 can release the gripper lift arm 460 from engagement with the wipe W releasing it from being trapped between the gripper lift arm 460 and the gripper blade 471. The gripper blade 471 can hold the wipe W once a spray cycle is complete thereby preventing a user from inadvertently pulling multiple wipes A through the dispensing aperture 416.

The actuator 431 can simultaneously activate the application mechanism 418, the dispensing mechanism 430, and the gripper 432. The user upon depressing the actuator 431 can advance (e.g. manually pulling or by powered gear rollers 438) the wipe W out the dispensing aperture 416 as a liquid composition is sprayed onto the wipe W. Upon releasing the actuator 431, the gripper lift arm 460 of the gripper 432 is released to return to its starting position engaged with the wipe W allow for easy tearing off of the wipe W from the remainder of the sheets.

The actuator 431 can activate the application mechanism 418, including the transfer element 427 to pump fluid toward the applicators 429, and simultaneously activate the dispensing mechanism 430 (if applicable). The mechanism by which the actuator 431 activates the application mechanism 418 and the dispensing mechanism 430 can vary. The spraying rate of the applicators 429 can be linked to the feed rate of the dispensing mechanism 430 such that the device 400 provides consistent spray volumes to the wipe W. The transfer element 427 can also include one or more valves, such as a piston pump with check valves that allow for consistent spray volumes. Thus, the device 400 can be a battery-powered motorized sprayer that allows for control of the amount of a liquid composition applied to each wipe W being dispensed, which will be discussed in more detail below. Depressing the actuator 431 activates the applicators 429 of the application mechanism 429 and also the transfer element 427 such that the spraying of a liquid composition is initiated. Depressing the actuator 431 also releases the gripper 432. This allows the wipes W to be pulled (or advanced automatically by motor 434) horizontally through the dispensing aperture 416 to get coated in a liquid composition. When the actuator 431 is released, the gripper lift arm 460 is allowed to travel down towards the wipe W to clamp the wipe W against the gripper blade 471 such that the lead wipe W extending beyond the dispensing aperture 416 can be torn off or released entirely. Thus, the device 400 can be fully automated with a push of a button and without any manual pulling of the wipe. Activation of the device 400 also need not include mechanical actuation and can incorporate electrical circuitry to activate any of the various components of the device 400. The input need not be a mechanical actuator or button that is physically depressed by a user. For example, the input (as well as any of the actuators described herein) can be a motion sensor such that upon waving of a hand over the sensor the input is electronically actuated in a "touchless" manner.

The device 400 can additionally incorporate one or more locks or switches to prevent inadvertent dispensing and/or application. For example, the system can incorporate an actuation lock to prevent oversaturation of the applicator 429 and/or the wipe W due to excessive pumping when a wipe W is not removed from the device 400. In another example, cover 494 is attached to a limit switch that can detect the presence of wipe W and prevent dispensing and/or running of motor 434 if no wipe W is detected.

Electronics and Data Tracking

Figure 1B:
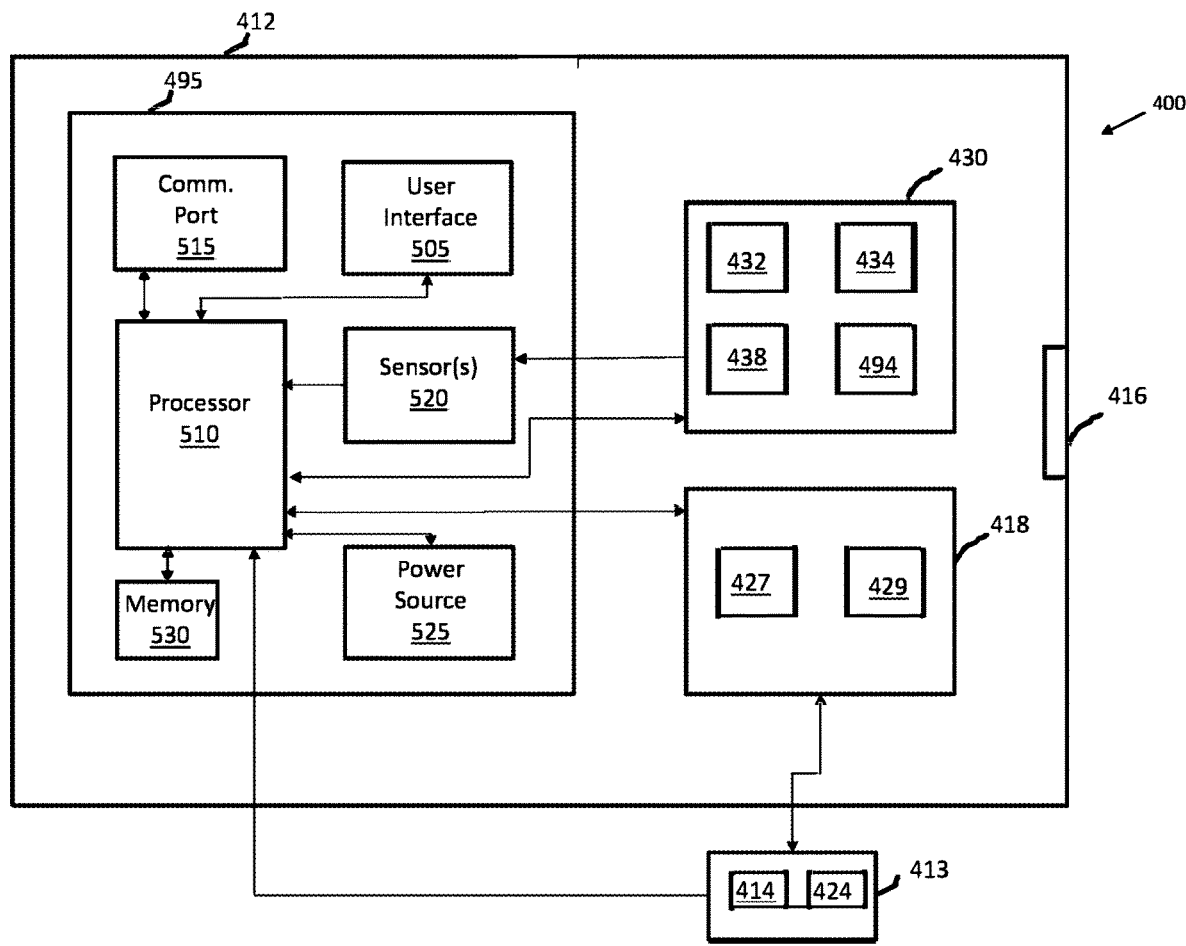
FIG. 1B is a box diagram showing an implementation of a device having computer system.

FIG. 1B is a block diagram showing an implementation of a device including a computing system 495. The computing system 495 can be configured to power, sense, monitor, and/or control one or more functions of the device 400. FIG. 1B shows the application mechanism 418 of the device 400 can include the transfer element 427, such as a peristaltic pump, and at least one applicator 429, such as a sprayer.

As described in more detail above, the application mechanism 418 of the device 400 can incorporate a powered motor, such as a battery-powered motor sprayer system. The motor for such an application mechanism 418 can be under the control of the computing system 495. The dispensing mechanism 430 of the device 400 can include an automatic feed system including a powered drive motor 434 and a plurality of gear rollers 438 configured to drive the wipes upon actuation of an input. The motor 434 can drive (directly or via one or more gears) the gear roller 438 configured to capture and direct the wipe W towards the dispensing aperture 416. The dispensing mechanism 430 can additionally include the gripper 432 that allows for a user to more easily tear the wipe W after dispensing and the cover 494 configured to close the dispensing aperture 416. The drive motor 434 for the dispensing mechanism as well as the gripper 432 can be under the control of the computing system 495. It should be appreciated that the one or more grippers 432 can be incorporated regardless whether the dispensing mechanism 430 is a manual mechanism as described elsewhere herein or a powered dispensing mechanism. Actuation of the input can simultaneously activate the application mechanism 418, the dispensing mechanism 430, including the gripper 432. Each of the application mechanism 418 and the dispensing mechanism 430 can be in communication with and under the control of the computing system 495. The computing system 495 in the device 400 allows for the device 400 to connect and exchange data thereby allowing the device 400 to more directly integrate with the environment within which it will be used. The computing system 495 allows for remote monitoring and control of the various functions of the device 400 thereby increasing its usefulness beyond merely applying a solution to a wipe at the indicator.

It should be appreciated that the computing system 495 can be incorporated within any of the various devices described herein regardless the method of application (i.e. contact or non-contact). Thus, any of the device embodiments described herein can incorporate one or more functions of the computing system 495, which will be described in more detail below. Certain features that are described in this specification in the context of separate embodiments and implementations can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or a variation of a sub-combination.

Again with respect to FIG. 1B, the computing system 495 of the device 400 can include a user interface 505, a processor 510, a communication port 515, one or more sensors 520, a power source 525, and a memory 530.

The processor 510 is capable of processing instructions for execution within the computing system 495. Such executed instructions can implement one or more of the methods described herein. The processor 510 can process instructions stored in the memory 530 as is known in the art.

The memory 530 is a computer readable medium such as volatile or non-volatile that stores information within the computing system 495. The memory 530 can be any type of memory capable of storing data and communicating that data to one or more other components of the device, such as the processor. The memory 530 may be one or more of a Flash memory, SRAM, ROM, DRAM, RAM, EPROM, dynamic storage, and the like. The memory 530 can receive and store data acquired during use of the device 400, such as from the one or more sensors 520, the user input 505, and other information related to dispensing the wipes and applying a solution to the wipes. The memory 530 can store user information, history of use, and various other data as will be discussed in greater detail below.

One or more aspects or features of the subject matter described herein may be realized in digital electronic circuitry, integrated circuitry, specially designed ASICs (application specific integrated circuits), field programmable gate arrays (FPGAs) computer hardware, firmware, software, and/or combinations thereof. These various implementations may include implementation in one or more computer programs that are executable and/or interpretable on a programmable system including at least one programmable processor, which may be special or general purpose, coupled to receive signals, data and instructions from, and to transmit signals, data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, one or more aspects or features of the subject matter described herein can be implemented via the user interface 505. The user interface 505 is configured to receive one or more inputs from a user and to provide one or more outputs to the user. The input from the user can be received in any of form including acoustic, speech, motion, or tactile input. The inputs can vary including pushbuttons, keypads, actuators, touchscreens, or other inputs as described elsewhere herein. The actuator 431, described in more detail above, is an example of an input that is part of the user interface 505. The inputs of the user interface 505 can be a mechanical actuator or an electric element. In some implementations, the user interface 505 can include a motion or optical sensor as described above to allow for touch-free dispensing of a wipe. The motion or optical sensor can be triggered after reaching a minimum threshold. For example, the device can be programmed to require at least 2 seconds of continuous motion detected by the sensor in order to dispense, thereby preventing accidental dispensing. The touch-free dispensing can be controlled such that a length of wipe extended is suitable for the type of wipe within the canister C and automatically dispenses out the appropriate length. For example, a light sensor can track perforations between individual wipes and automatically dispense to the location of the perforations.

In other implementations, the user interface 505 can include a microphone capable of receiving auditory inputs from a user. The devices described herein are configured to provide feedback to the user. The feedback can be any form of sensory feedback, such as for example visual feedback, auditory feedback, or tactile feedback. The feedback provided of the user interface 505 can vary as well including any of a variety of lights, sounds, vibrations, displays, and other outputs. The feedback of the user interface 505 can alert the user and/or provide the user with information regarding function, status of the device 400 and its components. The feedback can also provide alerts regarding battery life as is known in the art. In some implementations, the device 400 can incorporate a light that is not related to feedback regarding function of the device. Rather, the device can incorporate an external light on the lid to illuminate it and the surrounding area. Other user friendly features can be incorporated on the device as well. For example, the device 400 can include one or more attachments that allow the device 400 and its attached canister to be positioned in a convenient manner in a location. Magnets, clasps, hooks, and other features are considered herein. A strong magnet located, for example, on a back face of the canister can allow for the device 400 (coupled to a cartridge 413 and a wipe canister) to be attached to a magnetic surface. Similarly, a hook (detachable or built-in) can be positioned on a region of the device 400 allowing it to be hung near a point of use, for example, from hooks or horizontal bars. In an implementation, the device 400 can incorporate a handle similar to a handle on a pail such that a user can conveniently hold and transport the device 400. The handle can extend out from the base of the device 400 and be sufficiently long to swing over the top of the cartridge 413. Any of a variety of configurations of the handle are considered herein and as is known in the art.

The power source 525 can include one or more batteries. The power source 525 can be self-contained such that the entire power source 525 can be removed from the device 400. A power source 525 within the device 400 (as opposed to the removable cartridge 413) allows for the device 400 to be used without a cartridge 413. For example, a user may want to dispense a wipe from the device 400 without adding the liquid composition from the reservoir 414 of the cartridge 413. For example, the power source 525 can include one or more batteries enclosed in a battery pack that is replaceable and/or rechargeable. The power source 525 can be recharged such as by a USB port, induction charger, and the like. The power source 525 can include rechargeable battery such as NiCad battery, LiPo battery, NiMH battery or the like. In some implementations, data transfer via a wired USB/Micro USB connection can also recharge the power source 525 as is known in the art. In some implementations, the power source 525 can be located within a portion of the removable cartridge 413.

The communication port 515 is configured to provide communication between the device 400 and one or more other components. The device 400 can communicate with one or more of the cartridge 413, an external computing device 600, or another device 400 in a wired or wireless manner. In some implementations, the communication port 515 of the device 400 can include a transmitter/receiver configured to communicate with a corresponding transmitter/receiver on the cartridge 413, device 600, or device 400. The communication can be one-way or two-way wireless communication. The wireless communication can include a transmitter and/or receiver, radiofrequency (RF) transceiver, WIFI connection, infrared or Bluetooth communication device. The wireless connection can use any suitable wireless system, such as Bluetooth, Wi-Fi, radio frequency, ZigBee communication protocols, infrared or cellular phone systems, and can also employ coding or authentication to verify the origin of the information received. The wireless connection can also be any of a variety of proprietary wireless connection protocols. The wired connection can vary as well including a RS22 connection, USB/microUSB connection, Firewire connections, proprietary connections, or any other suitable type of hard-wired connection configured to receive and/or send information to the external device.

Figure 2:
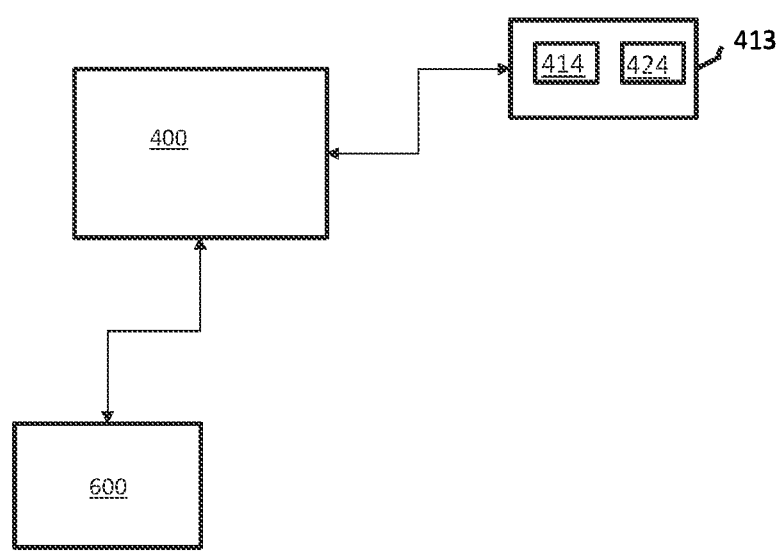
FIG. 2 is a schematic showing a device in communication with a remote computing device.

FIG. 2 illustrates an implementation of the device 400 having a communication port 515 configured to communicate with an external computing device 600. The external computing device 600 can include a communication port, a controller, and a user interface (such as a graphical user interface or GUI). The communication port 515 of the device 400 and also the communication port of the external computing device 600 can include a wired communication port. The communication mod port 515 and also the communication port of the external computing device 600 can alternatively or additionally include a wireless communication port such that information can be fed between the device 400 and the external computing device 600 via a wireless link. The external computing device 600 with which the device 400 communicates can vary including, but is not limited to, desktop computer, laptop computer, tablet computer, smartphone or other device capable of receiving data and running a software program to analyze the data. In an implementation, the external computing device 600 can be a remote server.

Figure 3:
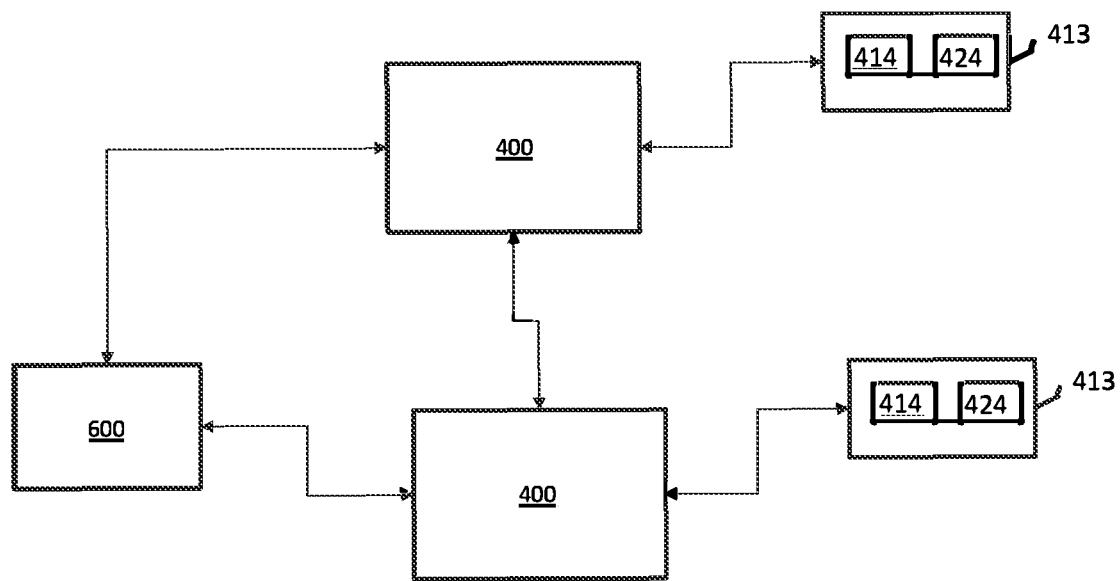
FIG. 3 is a schematic illustrating a plurality of devices in communication with a remote computing device and with one another.

The communication between the device 400 and external devices allows for the storage and analysis of such data transmitted. FIG. 3 illustrates an implementation of the device 400 having a communication port 515 configured to communicate with an external computing device 600 as well as at least one other device 400. The data from a single device 400 as well as aggregate data from a plurality of devices 400 can be transmitted, stored, and analyzed as will be described in more detail below. For example, the data can be analyzed by a software program to calculate wipe usage, duration between dispensing of wipes, battery level, device status, device performance, cartridge solution level, number of wipes remaining in a canister, expiration date of device and/or cartridge, total run time of a device, wipe data for rooms with outbreaks, etc. Any of a variety of data can be analyzed for a variety of reasons as described elsewhere herein. The software program can analyze the data to extrapolate cost metrics, trends over time, and make predictions regarding future usage in order to inform ordering and budget allocation decisions. For example, a first device in a particular location (e.g., operating room) may experience heavy use over a certain period of time. The devices purchased may need to be greater for that purchase period to cover the increase in use to compensate.

The communication between the device 400 and the external computing device can also allow for remote wireless control of the device 400. For example, a user can use the remote wireless control to adjust functions of the device 400 such as the speed of the dispensing mechanism 430, or volume of solution dispensed by the application mechanism 418. The remote wireless control of the device 400 can allow a user to dispense a wipe remotely or disable the device 400 altogether. The speed of dispensing, volume of solution dispensed, etc. can be adjusted manually on the device such as via an input like a button or switch as well as an interactive touchscreen on the device 400.

As mentioned above, the devices described herein can incorporate one or more sensors 520 configured to sense various functions of the device 400. The one or more sensors 520 can sense various events that occur and communicate with the processor 510 such that the processor 510 can monitor, analyze, record in memory the variety of data points such that one or more functions of the device 400 can be controlled. Data from the one or more sensors 520 can identify whether and how the device 400 is being used (e.g. whether a wipe is dispensed or ready to be dispensed, the number of wipes dispensed, when wipes are dispensed, timing between when wipes are dispensed, frequency of wipes dispensed over time, whether multiple wipes are dispensed simultaneously, etc). The data from the one or more sensors 520 can be communicated in real-time to the processor 510, which can analyze the data, display the data, and/or communicate the data to an external computing device 600. The data from the sensors can be processed into one or more processed signals representative of how the device 400 is being used, for example, for the purposes of tracking budget, inventory, efficiency, waste, whether safety protocols are being followed, etc. The various methods of use are described in more detail elsewhere herein.

In some implementations, the one or more sensors 520 can include a sensor configured to identify when a wipe has been dispensed from the device 400. The dispensing aperture 416 can contain a mechanical flap or cover 494 configured to cover the aperture 416 (see FIG. 12B). The sensor 520 can be an optical sensor or another type of sensor positioned relative to the cover 494 to detect the presence of a wipe within the passageway of the aperture 416 and cause the system to regulate whether or not a liquid composition can be applied upon actuation of the input. For example, the cover 494 can swing or be otherwise displaced when a wipe is present within the aperture 416. Movement of the door 494 can interface with the sensor 520. The sensor 520 can communicate with the processor 510 upon sensing a wipe, which can cause the processor 510 to inactivate the application mechanism 418 and/or the dispensing mechanism 430. For example, the inactivation can result in no liquid composition being dispensed even when the actuator 431 is pressed thereby preventing waste or drips. The actuator 431 can only dispense the liquid composition when the sensor 520 detects a wipe is ready to receive it. Position of the cover 494 relative to the dispensing aperture 416 (e.g. displacement or lack of displacement) can be detected by the sensor 520 and information regarding the position communicated to the processor 510. The processor 510, in turn, can modulate (i.e. deactivate or activate) the application mechanism 418 and/or the dispensing mechanism 430 such that liquid is dispensed (or not dispensed) onto the wipe upon actuation of the actuator 431. The sensor 520 can prevent inadvertent dispensing and waste of liquid from the device.

Additionally, if no movement of the cover 494 occurs for a selected period of time (e.g., 10 seconds-30 seconds, or 30 seconds-1 minute, or 1-2 minutes, or 1-5 minutes, etc.), the gear rollers 438 can turn in an opposite direction away from the aperture 416 to retract the wipe from the aperture 416 and back into the lid. Once the cover 494 is no longer displaced, the gear roller 438 can stop. The wipe enclosed within the lid prevents inadvertent drying out of wipes. In other implementations, the sensor 520 is an optical sensor that detects the present of the wipe hanging out of the aperture 416. Once the wipe is pulled away from the line of sight of the optical sensor, the gear roller 438 can stop retracting the wipe. The device can incorporate more than one sensor. For example, a first sensor configured to detect position of the cover 494 and a second sensor configured to detect the wipe hanging out of the aperture 416.

The period of time before automatic retraction of the wipe can be configured through software settings. In some implementations, the device 400 can be in communication with an external computer running a software program. In other implementations, the processor of the device 400 itself can run the software program. A user can program and/or interact with a user interface such as a touchscreen display on the device 400 (or the external computer) to set the period of the idle time before automatic wipe retraction occurs. Idle time before retraction programmed using the software can be a period of seconds (e.g., 10 seconds to 59 seconds) up to a period of minutes (e.g., 1 minute to about 60 minutes). Retraction of the wipe can also be manually activated such as by the user actuating an input on the device 400 to cause the wipe to retract on demand.

The automatic retraction of the wipe described above can coordinate with one or more alerts by the user interface 505 to indicate to a user the wipe is about to be retracted within the device 400. For example, the computing system 495 of the device 400 can additionally incorporate a timer. The user interface 505 (which can include one or more lights, displays, or a speaker, etc) can be configured to alert a user prior to the end of the selected period of time. The timer can also cause the device 400 to enter a sleep mode after a period of inactivity to preserve battery life.

Inadvertent drying out of wipes intended to be dispensed wet can lead to the wipe being insufficiently soaked with fluid to be effective in coating the surface. The device can incorporate features to prevent insufficiently wetted wipes from being dispensed or to alert to the user that wipes are insufficiently wet, through one or more alerts by the user interface 505. In some implementations, as the wipes are fed through the rollers, the amount of compression of one roller (e.g., the bottom roller) can be used to approximate the mass of the wipe being dispensed. The weight of the wipe can be used to determine its wetness. A notification such as an alarm or a message displayed on the lid can be triggered if the wipe being dispensed is below a weight threshold that indicates the wipe is insufficiently wetted. In some implementations, the amount of liquid being compressed out of the wipe as the wipe is fed through the rollers can be measured by a scale or detected by a sensor. The scale or sensor can be positioned near the one or more drainage holes (i.e., drainage holes 428) intended to drain excess liquid back into the canister as the wipe is dispensed. Data regarding weight of the liquid collected can be used to approximate wetness of the wipe being dispensed.

The computing system 495 can include a counter to monitor and record the number of wipes used over a period of time. One method includes counting based on the amount of time spent actuating an input of the user interface 505 to dispense the wipes. For example, pressing a button for 2 seconds may allow 1 wipe to be dispensed. If the button was pressed for a cumulative 120 seconds for one day, the data can show 60 wipes were dispensed that day. The method can also include counting based on the number of revolutions made by the gear roller 438. For example, if the number of revolutions by the gear roller 438 is 4 to dispense a single wipe, 120 revolutions in a day equals 30 wipes dispensed that day. Counting of wipes can also be based on an optical sensor positioned near the aperture 416 as described above. The optical sensor might detect the perforations between wipes to count how many are dispensed.

The counting data can be synchronized with time logs. When the data is accessed (e.g. after wirelessly synced into a software program), a breakdown of wipe usage can be performed based on time intervals (hours/shifts, days, months, year, etc). This sort of inventory data may be useful for a user (e.g., an EVS manager) to monitor how many wipes are being dispensed from a specific device 400 per shift, per week, etc. This data could allow the user to track upticks in wipe usage based on the season or during outbreaks and adjustment can be made. The data can allow a user to monitor compliance and identify whether staff is using enough wipes for each room. For example, housekeepers may change their wipes too infrequently leading to reduced efficacy and transfer of pathogens between surfaces. Conversely, the data can allow a user to determine whether too many wipes are being used per room leading to unnecessary waste. The data can allow for estimating inventory needs and budget allocation. The data can be used for cost-benefit analyses in research or financial studies.

The counting data can be useful for tracking inactivity or the duration of time between dispensing wipes. A time log can track when the input is activated and for how long. This data can provide information regarding frequency users dispense wipes and whether multiple wipes are dispensed simultaneously (e.g., 3-4 at a time) or only a single wipe dispensed at a time. The data from the time log can show inactivity between dispensing of the wipe and the length of those periods of inactivity. This can provide insight into how much time a user takes to use a wipe before dispensing a new wipe. The data can show whether too few or too many wipes are being dispensed. This sort of data can be useful for facilities having a cleaning protocol in place that requires wipes to be used for no more than 3 minutes continuously without changing to a fresh wipe. The data can show whether wipes are being dispensed at a significantly less frequent rate (i.e., every 15 minutes) and alert managers to staff errors. In the instance of longer periods of inactivity (e.g. 1 hours up to 1 day to 1 week), the processor 510 can cause the device 400 to enter sleep mode and turn off non-essential functions in order to preserve battery power. The period of inactivity can be user-selected depending on how frequently or infrequently a device 400 is typically used.

In some implementations, the cartridge 413 can include one or more sensors (e.g. near a bottom of the cartridge 413 and reservoir 414) configured to detect liquid volume of the reservoir of the cartridge 413 and communicate information regarding the liquid volume to the processor of the device. The device can provide an alert to notify a user when liquid volume within the cartridge 413 has dropped below a threshold level. The sensor configuration can be an optical sensor or a mechanical sensor. The sensor of the cartridge 413 can be a float-level sensor. In some implementations, slot 437 of the device 400 can incorporate a sensor that measures mass to determine the liquid volume within the cartridge 413.

The counting data in the log can provide additional information regarding activity of certain devices 400 and mapped to productivity. The usage of a device 400 can help a user determine whether cleaning is being handled inefficiently and according to protocol. The data can help to identify any of a variety of activity patterns and whether too many breaks are taken in between rooms, as well as inefficiencies in: the lay-out of the rooms, which rooms a particular user is assigned to clean, where the supply closet is located, poor performance from unmotivated staff, long lunch breaks, etc.

As mentioned above, data from the device can be analyzed by software programs to calculate various data points (e.g., wipe usage, duration between dispensing of wipes, number of wipes remaining in a canister, total run time of a device, etc.) The software program can be adapted to take into account details about the wipe that is being dispensed from the canister to improve the accuracy of these calculated data points. As an example, different wipes can have different dimensions and the different wipe dimensions can impact a user's understanding of the data. As an example, PDI Sani-Cloth Bleach wipes can have a shorter length (e.g., 6.5 inches) compared to the length of a Clorox Healthcare Germicidal Bleach wipe (e.g., 12 inches). The specific type of wipe contained within a canister and/or the length of the wipe being dispensed can be used in the calculation of the time needed to dispense a single wipe.

The device can detect certain brands of wipe such that the calculations of the various data points are adjusted depending on which canister of wipe the lid is coupled to. The method of detecting the different brands of wipe can vary including sensors on the device 400, the adapter 700, and/or the canister. As an example, the device 400 can include a sensor near its lower end region where the device 400 and the canister couple that is configured to interface with one or more feature of the wipe canister to provide information regarding the wipe to be dispensed from the canister. Similarly, a sensor 705 can be positioned on the adapter 700 coupling the device 400 to the canister. The sensor 705 can vary in configuration including mechanical, electronic, optical, magnetic, or other form of sensor. In some implementations, the sensor 705 is a mechanical switch or button. In other implementations, the sensor 705 is configured to interface with or detect a readable code. Different manufacturers of different types of wipes may incorporate slight differences between the wipe canisters that can be detected by the sensor of the device 400 or adapter 700 when the device 400 is attached to the canister. For example, manufacturers may elect to include a tactile series of ridges and bumps, notches, RFID tags, etc. to differentiate their wipes to be read by sensor 705. The sensor 705 can communicate information about the wipe canister to the processor of the device 400, which in turn can be programmed to automatically adjust the device mechanics based on the detected differences, for example, changing motor speed, volume dispensed, etc. to compensate for the differences in wipes being dispensed through the device 400. In some implementations, the sensor 705 near the lower end of the device 400

(FIG. 15) or the adapter 700 (FIG. 14A-14C) can be a mechanical rod or an electronic sensing element that informs the computing system of the device 400 that the wipes held in the canister are larger in size and/or being dispense from a larger canister size. The information detected by the sensor 705 of the device (or on the adaptor) provided by the corresponding feature (e.g. the code) on the canister can vary.

Figure 14A:
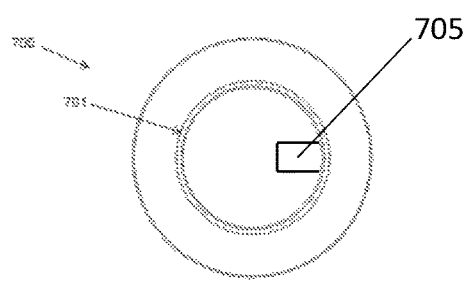
FIG. 14A-14C shows top (A), side (B), and perspective (C) views of an adapter for the lid device having a sensor.
Figure 14B:
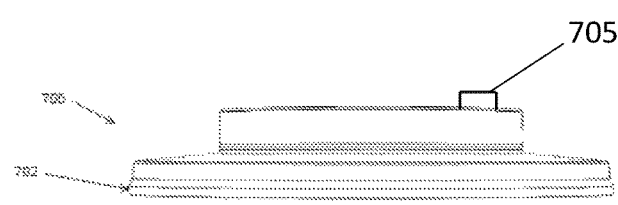
Figure 14C:
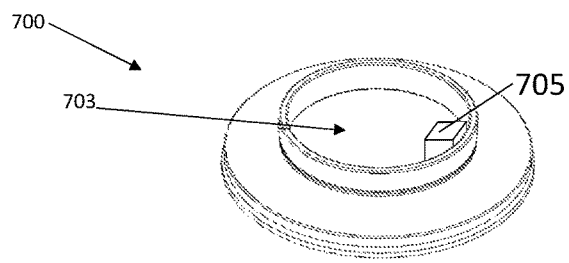
Figure 15:
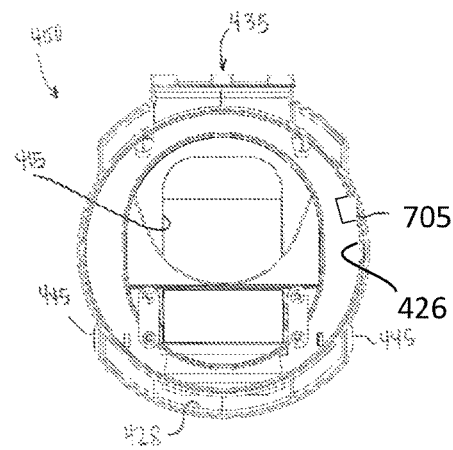
FIG. 15 shows a bottom view of a device having a sensor positioned near a lower end region.

FIGS. 14A-14C illustrate an implementation of a sensor 705 positioned on a region of the adapter 700. The adapter 700 can include an upper lip 701 that is sized and shaped to interface with a lower end region of the device 400. The sensor 705 can be a mechanical feature positioned on an inner surface of the upper lip 701 such that when the upper lip 701 encircles the lower end region of the device housing, the sensor 705 physically engages with the device housing. Alternatively, the sensor 705 can be positioned on an inner surface of the bottom ring 433 of the device 400 configured to surround and engage with an upper rim of a canister (see FIG. 15).

Again with respect to FIGS. 1B, 2, and 3, the cartridge 413 and the device 400 may communicate with one another by incorporation of a data element 424 on the cartridge 413 configured to be in communication with the communication port 515 of the device. As an example, the data element 424 can store data about the cartridge 413 such as contents, volume, date of manufacture, the intended brand of and size of wipe the cartridge 413 is to be used with, as well as any other information regarding the cartridge 413. The data can be stored within the element 424 and communicated to and received by the processor 510 of the device 400 upon "reading" the element 424 on the cartridge 413. The identification of the cartridge 413 can be initiated automatically by software run by the processor 510 of the device 400. The data element 424 of the cartridge 413 can include an encoder or bar code type strip configured to be scanned and read by a corresponding reader device of the device 400 that is in operative communication with the processor 510. The data element 424 may alternatively be an RFID chip, physical features such as bumps, ridges, or notches that can be detected or read by device 400, or the like that transmits data to a reader such as a data receiving processor or the like. Such encoder devices include the ability to securely transmit and store data, such as, via, encryption, to prevent unauthorized access or tampering with such data. The recognition of the element 424 also ensures genuine cartridges and/or the correct cartridge is installed with the device 400. For example, the element 424 can identify the contents of the reservoir and the device 400 can be programmed to ensure the content of the reservoir 414 is suitable for the type of wipe contained in the canister C. For example, the formula in the reservoir 414 of the cartridge may be suitable for a PDI bleach wipe with a 4 minute fading time or a Clorox bleach wipe with a 3 minute fading time, etc. Indicator compositions for different disinfectant wipes may require a particular volume be dispensed from the cartridge 413 in order to achieve the appropriate final formulation. For example, a bleach wipe may have a particular indicator composition dispensed at a certain volume (e.g., 1.5 mL) to achieve the proper final formulation for use. A quat/alcohol wipe may have a different indicator composition dispensed at a smaller volume (e.g., 0.75 mL). Communication between the cartridge 413 and the device 400 identifying what liquid composition is contained within the reservoir 414 and/or what type of wipe is contained within the canister can allow for the device 400 to automatically adjust the dispensing of that solution, for example, by adjusting the flow rate, volume, and/or wipe dispensing speed as appropriate to achieve a particular final formulation. The adjustment can be achieved mechanically such as via buttons, switches or electronically. It is useful for the device 400 to "read" the cartridge 413 to ensure proper setup before use. Other data can be contained within the element 424 such as a starting solution volume, expiration date, etc. The device 400 can be prevented from dispensing a solution to a wipe if the solution is determined to be incompatible. The data can be stored to track what solutions are used with which wipes, when they are installed together, whether used in its entirety, and whether the same device 400 is used with another type of wipe canister, etc.

In some implementations, wipe manufacturers can build readable features (mechanical, magnetic, optical, electronic, etc.) near the upper rim of the canister. Upon coupling the device 400 to the canister, the feature can trigger (e.g., by the mechanical sensor 705 or switch on the device 400 or adapter 700) automatic adjustments in the mechanics of the device 400 to accommodating the differences in the wipe contained in the canister. For example, a manufacturer of one type of disinfectant wipes may have one notch on the rim of the canister whereas a manufacturer of a different type of disinfectant wipes may have two notches on the canister rim. When the device 400 is mounted onto these different canisters, the device 400 can detect based on the presence of the notches the brand of wipe. The cartridge 413 can be customized for the brand and/or size of wipe as well.

One or more codes can be incorporated into a part of the cartridge 413 or into part of the canister that can be detected and "read" by a corresponding sensor on the device 400. The readable features can be mechanical, magnetic, optical, or electronic. For example, the cartridge 413 can include a data element 424 as described above. In other implementation, the one or more codes can be a tactile series of ridges and bumps, similar to Braille, that form a code detected by the sensor of the device 400. The code detected by the sensor can provide information about the wipe contained in the canister (or the cartridge 413). As an example, a first section of code can delineate wipe chemistry, a second section of code can delineate wipe dimension, and a third section of code can delineate a further wipe dimension, and so on. The first section of code can be a single horizontal line indicating the wipe is a bleach wipe or two horizontal lines indicating the wipe is a hydrogen peroxide wipe, etc. The second section of code can be a number of shapes indicating a width of the wipe. For example, six circles can indicate the wipe is six inches wide. The third section of code can be a number of a different shape indicating a length of the wipe. For example, ten squares can indicate the wipe is ten inches long.

The above are just examples of codes considered herein and is not intended to be limiting. Any of a variety of codes can be incorporated to communicate information between the components of the systems described herein as is known in the art. The communication of data between the device 400 and the canister and/or the cartridge 413 and the device 400 need not be automatic, but can also be manually inputted. For example, the device can incorporate a touchscreen or dedicated input to provide information related to the wipe dimension and/or chemistry.

The memory of the computing system 495 can be configured to maintain a record for a particular cartridge 413 and/or device 400. For example, the record can indicate when the cartridge 413 or device 400 is beyond its expiration date. Once a cartridge 413 and/or device 400 has reached a particular threshold, the software can be configured to write onto the memory of the data element 424 of the cartridge 413 such that upon subsequent use, the device 400 is alerted to the information that the cartridge 413 should not be used. Thus, information can be sent between the device 400 and the cartridge 413 in a two-way manner.

The cartridge 413 may also include one or more other sensing mechanisms configured to monitor the volume of solution within the reservoir 414 over time. The sensor(s) of the cartridge 413 can communicate such data to the processor 510 of the device 400 such that when the reservoir 414 is near to empty that information can be relayed to a user from the device 400. The processor 510 can be configured to activate one or more alerts such as a sound, a light, or other sort of display on the user interface 505 to indicate to the user the cartridge solution is running low and the cartridge 413 needs to be replaced. The sensor can be an optical sensor or a circuit chip that estimates volume levels within the reservoir 414 based on how much time it has spent dispensing solution, etc. Other sensors can be incorporated within the device 400 to track and display the approximate level of wipes remaining in the canister (i.e., weight or optical sensors).

In an implementation, a sensor in the base of the device 400, such as an optical sensor, can detect a dimension of the wipes remaining in the canister such as a diameter/radius of the wipe log. The measured dimension indicates how many wipes remain. For example, a wipe log with a radius of about 1 inch can be estimated to have 20 wipes left. The wipe log dimension can be calibrated based on a measured dimension prior to dispensing the first wipe in the log and the number of wipes known to be in the wipe log. The sensor in the base of the device 400 can also be configured to detect weight of the wipe log. The number of wipes remaining can also be calculated based on the number of wipes in a wipe log upon loading the wipe log in the canister minus the number of wipes dispensed through the device.

In still further implementations, an assembly formed by the device 400 having a cartridge 413 loaded therein and fastened onto a wipe canister can be mounted on a wall mount. The wall mount can include a sensor and a communication unit configured to communicate with the device 400. The sensor of the wall mount can be configured to assess weight of the assembly and relay that information to the device 400. The information can be used to estimate how much volume and how many wipes remain in the assembly. For example, an assembly including a new cartridge 413 installed within a device 400 that is attached to canister of wipes may have a starting weight of about 8 lbs. If 50% of the wipes of the assembly are consumed, the assembly may weigh 5.5 lbs. If 100% of the wipes of the assembly are used (i.e. no more wipes in the canister), the assembly may weigh only 3 lbs. The weight sensor in the wall mount can communicate to the device 400, which in turn may notify a user, when the weight of the assembly drops below a set lower threshold. The lower threshold may be when all the wipes are all consumed (e.g. weighs 3 lbs in the scenario described above). The lower threshold may be when the wipes are low, but not completely gone (e.g. weighs 3.1 lbs in the scenario described above).

In a further implementation, a moisture sensor can be positioned within the canister such that when the moisture content within the canister falls below a certain threshold indicating the wipes are nearly dry, the sensor can communicate information to the device 400 to alert the user. Any of a number of sensors can be incorporated within the cartridge 413, the device 400, the wall mount, and/or the canister holding the wipes.

The computing system 495 can collect data (e.g. from one or more sensors 520) related to the performance and internal mechanics of the device 400. For example, the speed of the drive motor 434 for the feed system, torque of gear rollers 438, performance of the pumping element 463, the volume of solution dispensed, battery life, etc. can all be monitored by the computing system 495. The data can be used for calibration or maintenance purposes. If, over time, certain functions of the device 400 change (e.g., gear rollers 438 rotate more slowly or undergo an increase in torque, or the volume of solution dispensed decreases due to pumping element malfunction or clogging), adjustments can be made to compensate. Or, if adjustments do not fix the problem, the device 400 can alert users that maintenance/repairs are needed. The device 400 can also monitor the expiry of a device 400 and/or cartridge 413. For example, upon first installation of a device 400 with a canister of wipes a time log entry can start a countdown in time (i.e. days, months, years) and/or in number of wipes dispensed from a particular device 400. The device 400 can then provide a user alert regarding an expiry of a shelf-life period or when a maximum number of wipes has been dispensed before optimal performance is no longer expected. The user alerts can vary including a displayed message, a sound, a blinking light, and the like to alert a user of various information regarding the device 400, the cartridge 413, and/or the wipes within the canister. For example, the alert can be triggered to notify the user when a cartridge or wipe canister should be replaced, approaching a shelf life of a particular device or canister of wipes, when a maximum number of wipes has been dispensed, etc.

As described herein, the devices 400 described herein can communicate wirelessly to a remote location such as an external computing device 600. That communication can provide information regarding the physical location of the device 400. The location data can be such that a device 400 is linked to a particular patient room, a floor, wing, or department within a building. The location data can be tracked via software such as on a remote computing device or server. Location data may be useful to a manager of a facility to keep track of where the devices 400 are located within a particular facility and whether distribution of devices within that facility is acceptable. For example, when using a software program to monitor the location of all devices 400 in a particular facility, a manager may notice that several devices were moved from one wing or department to another wing or department, which could leave that region without sufficient devices to meet the need. The manager can the more easily redistribute the devices 400 throughout the facility.

Tagging the devices 400 by location may allow the manager to monitor wipe usage in rooms with outbreaks. For example, if a patient in one room suffers an outbreak (e.g., *C. difficile*), the manager may look specifically at data transmitted by the device 400 at that particular location to inform the manager how many wipes may have been dispensed and used to disinfect the room at the time of the outbreak. This can help to correct breaches in protocol and/or to adjust cleaning habits accordingly. Additionally, upon an outbreak of a highly contagious pathogen such as *C. difficile*, the device 400 is preferably quarantined to that room or disinfected thoroughly before being moved out of the room. The device 400 can be "tagged" as having been located within a breakout room such as by a light, alert, or other switch or monitor system can be toggled back to an off position after fully disinfecting. Such location tracking also can help to identify stolen or misplaced devices 400. This may prompt a user to remotely disable the device 400.

A plurality of communication units within a facility can create a "geofence" that allows for instant alerts and/or disabling of devices 400. If a device 400 is detected to be located more than a threshold distance outside the geofence for a minimum threshold period of time, the device 400 can be flagged as "stolen" and be remotely disabled. The threshold distance and threshold period of time can vary and can be programmed by a user. As an example, the threshold distance can be at least about 10 feet outside the geofence and the threshold period of time can be 10 minutes since the device 400 was last detected. In some implementations, the geofence can be created by mounting a plurality of communication units within a facility such that each of the plurality of communication units tracks device activity in relationship to a specific location such as a specific hospital room. The communication unit can be mounted above the door of the room, for example, and flag when a device 400 enters and exits the room. This configuration allows for tracking of the devices 400 in a more specific manner on a room-by-room basis. The room-by-room tracking can also provide information as to whether one room has been skipped (i.e., no device 400 entered a particular room) or was left inside a room (i.e., the device 400 that entered the room did not exit the room). The computing system 495/600 can be programmed to use this information to determine an amount of time each device 400 was located inside each room for quality control auditing and/or workflow management purposes.

In other implementations, a communication unit can be mounted outside a door of a particular patient room. The unit can detect a device 400 as being within a particular radius (e.g., within a 5-foot radius) for a minimum threshold period of time (e.g., 30 seconds). The communication unit can detect a device 400 has met the thresholds and can tag the device 400 as having entered that particular room. This configuration allows for the scenario where a worker may clean a room with a wipe, but may not carry the canister of wipes into the room to perform the cleaning. A device 400 coupled to the canister may be left outside of the room, but within the minimum threshold radius for at least the threshold period of time and be tagged as having been used for that room.

In still further implementations, the communication unit can be embedded on a wall canister mount located outside a patient room. The communication unit can detect and track the presence or absence of a lid device 400 inside the wall mount. This configuration may be useful to track how often the lid device 400 is removed from the wall mount, for example, to replace a used canister with a fresh canister. This information can also be useful to assess whether a wall canister mount is empty and needs a new canister and lid device. The information can be used to identify when a particular canister of wipes (e.g., bleach wipes) should be replaced due to passing of an expiration date. The location tracking described herein can use Bluetooth, Wi-Fi, and/or GPS signaling.

Generally, disinfectant wipes require a certain contact time to fully inactivate pathogens on a surface. The device 400 can include a timer function that provides a visual and/or audio cue for users to keep track of elapsed time of contact. In some implementations, a countdown may begin at the time the wipe is dispensed and an alert after a time period identify the expiration of that time period. The user interface 505 can also display the countdown time. More than a single timer can be incorporated as well.

Any of a variety of features can be incorporated in the devices described herein. As described above, the computing system 495 can include a microphone. User queries or commands can be provided to the computing system 495 via the microphone. In some implementations, the processor 510 is programmed to provide coaching or guidance regarding what sort of disinfectant wipe is needed for a particular pathogen and can response to a query with such programmed information. As an example, a user can ask what type of disinfectant wipe is needed to treat a particular pathogen (e.g., *C. difficile*). The computing system 495 can respond via a speaker of the user interface 505 with the answer along with information regarding whether the device 400 contains appropriate wipes (e.g., "bleach wipe"). The speaker of the user interface 505 can also provide other audio instructions from the device 400.

As another example, a user can ask what contact time is optimal for the particular pathogen (e.g., *C. difficile*). The computing system 495 can respond via the speaker of the user interface 505 with the answer along with information regarding whether the device 400 contains appropriate wipes (e.g. "bleach wipe takes 3 minutes of contact time"). The user can ask any of a variety of questions such as which surfaces should be wiped in a certain type of room (e.g., inpatient room vs. operating room), what types of surfaces or equipment are compatible with certain types of disinfectants (e.g., "Is X machine compatible with bleach wipes?"), and about their own performance metrics (e.g., average number of wipes per room, time spent per room, etc.).

Optic sensors in a room or area or on device 400 can be incorporated to track color indicator on a particular surface and alert a user when the surface(s) is successfully disinfected. A camera system or full-room optical sensor system can be used to monitor the surfaces successfully wiped (e.g., initial color for coverage, and then when color indicator has faded indicating completion of disinfection). The data regarding successful disinfection can be tracked in a room-by-room manner providing information regarding thoroughness of cleaning. For example, the camera system can link with the device 400 in a wireless manner and communicate the information to a central server, for example, which in turn can store the data for analysis. For example, lid device A in room A tracked 75% of high-touch surfaces were cleaned whereas lid device B in room B tracked 95% of high-touch surfaces were cleaned, etc. The camera or optical sensor system can detect whether a surface was missed within a period of time after initiation of cleaning and alert a user with a visual or audio reminder with that information (e.g., no disinfectant was applied to a desk table within 5 minutes of the first wipe being dispensed in the room.

In some implementations, a cartridge 413 can be configured to dispense a mixture at the point-of-use. The mixture can include a mixture of dyes that can provide any of a variety of colors useful for identifying a treatment. The dyes can be primary colors that when combined produce a secondary color (e.g., a blue dye and a yellow dye combine to make a green color when spread or wiped onto a surface). The combined dyes can have different fade times, for example, a first dye that fades in 1 minute and a second dye that fades in 3 minutes, etc. Fading of one of the two dyes can result in the secondary color turning back into the primary color due the first dye fading faster than the second dye. The sequential fading of mixtures of dyes provides additional indication to the user about how much time has elapsed. As an example, the first dye can be yellow having a fading time of 1 minute and the second dye can be blue having a fading time of 3 minutes. When the yellow and blue dyes are combined at the point-of-use and are applied to a surface for disinfection, they provide a green color. After a first period of time (e.g., 1 minute), the yellow dye fades away causing the surface to turn from green to blue. After a second period of time (e.g., 2 minutes), the blue dye fades to colorless. Once the blue dye fades to colorless, the user understands that 3 total minutes has elapsed since the wipe was initially applied.

Disinfectant wipes can be used that have different contact times for different pathogens. For example, some bleach wipes may specify 1 minute contact time for norovirus and a 3 minute contact time for *C. difficile* spores. Therefore, a healthcare worker that is disinfecting a room with a known norovirus outbreak can confirm the appropriate amount of time for disinfecting for norovirus because the initial green color fades to blue, while a worker disinfecting a room with a known *C. difficile* outbreak will wait for the green to fade to colorless. Other color combinations are considered herein provided there is a visible change from an initial color (e.g., color A) to a second color (e.g., color B), and finally to colorless. Additional color stages are considered as well. For example, the dispensing cartridge may contain four dyes timed to fade after 30 seconds, 1 minute, 2 minute, and 3 minutes. Any water-soluble dye that may allow successive fading times and visibility may be used. Additionally, pH dyes may be used in the disinfectant solution.

Any of a variety of formulations can provide the timed functionality described above. For example, indigo carmine in combination with FDC Red 40 may provide an initial color that is purple. FDC Red 40 can be at a lighter concentration to fade faster than indigo carmine such that the purple turns to blue within a first period of time (e.g., 1 minute) and after a second period of time (e.g., 3 minutes), the remaining indigo carmine fades to colorless. Different dyes can be selected based on which are sensitive or resistant to bleach oxidation.

Compositions for use with the devices described here, and related methods, are described in more detail in the following sections.

Compositions and Methods

The present disclosure provides additional and improved indicator compositions relative to those disclosed in the inventors' earlier work published as WO 2018/022621, the contents of which are hereby incorporated by reference in their entirety. The compositions described here further take advantage of certain additional and improved features of the devices described here to provide improved performance and flexibility in surface disinfection and decontamination.

The present disclosure provides single and multi-component indicator compositions which impart a visible color to a disinfectant composition. In some implementations, the single and multi-component indicator compositions comprise a colorant and a catalyst, which catalyst may be provided by the disinfectant composition, or may form a component of the indicator composition, and one or more optional additives. The one or more optional additives may be selected from an alkyl amine, an anticaking agent, an anti-foaming agent, an antimicrobial agent and preservative, an antioxidant, a butter, a chelating agent, a co-emulsifier, a co-surfactant, a copolymer, a corrosion inhibitor, an emollient, an emulsifying or dispersing agent (these terms are used interchangeably), an emulsion stabilizer, a filler, a foaming agent (interchangeable with foam-boosting agent), a humectant, a moisture-absorbing agent, an occlusive, an oil, an opacifying agent, an oleochemical, an organic acid, a pearlizer, a perfume or fragrance, a polymer, a rheology modifier, a silicone, a silicone conditioner, a stabilizer, a stabilizing salt, a surfactant, a texturizer, a vitamin, a wax, and combinations or mixtures thereof, each of which is described in more detail below. In some implementations, the one or more optional additives includes at least one or both of a surfactant and a rheology modifier. The terms "thickener", "thickening agent", "viscosity modifier", "viscosity regulator" and "rheology modifier" are used interchangeably herein. In some implementations, the optional additive may comprise a pH modulator such as an acidic agent, an alkaline builder or base, or a suitable buffer system adapted to maintain a desired pH, which may be an acidic or basic pH, as described in more detail below. In some implementations, the optional additive may comprise a disinfectant.

The disclosure also provides methods for disinfecting a surface that comprise a step of combining (i) a single component indicator composition as described here with a disinfectant composition or (ii) the various elements of a multi-component indicator composition to form a single indicator composition that is mixed with a disinfectant composition to impart a color thereto, both methods further comprising a step of applying the colored disinfectant composition to a surface and allowing the colored disinfectant composition to remain in contact with the surface for a period of time until the color has faded to clear, thereby disinfecting the surface. In some implementations the surface is a porous or nonporous surface, for example a woven or non-woven fabric, concrete, steel, wood, ceramic, polypropylene, plastic, glass, metal, or granite. In some implementations, the surface is skin, for example, a user's skin where the indicator composition is in the form of a liquid or gel, such as an alcohol-based disinfecting hand gel. In some implementations, the surface is not the inside of a toilet bowl. Depending on the intended use and the disinfectant composition to be colored, the component indicator compositions can be adapted to impart color to the disinfectant composition which fades to clear after application to a surface over a period of time ranging from 5 seconds to 30 minutes or from 5 seconds to 60 minutes, for example from 5 to 120 seconds, or from 2-5 minutes, or from 5-10 minutes, or from 10-30 minutes, or from 10-60 minutes.

In some implementations, the at least one colorant of an indicator composition described here is a water-soluble oxidizable dye, preferably selected from an azo dye, a triarylmethane dye, a phenol dye (e.g., 3-nitrophenol), a cationic dye (also referred to as a "basic" dye), an anionic dye (also referred to as an "acid" dye, e.g., alizarine blue and acid red), a thiazine dye, an indigoid (e.g., indigo carmine), and a leuco dye (e.g., indigo, crystal violet). Azo dyes are organic compounds bearing the functional group R—N=N—R', in which R and R' are usually aryl. Triarylmethane dyes are synthetic organic compounds containing triphenylmethane backbones and include methyl violet dyes, fuchsine dyes, phenol dyes (e.g., phenolphthalein, phenol red, chlorophenol red, cresol red, bromocresol purple, bromocresol green), malachite green dyes (e.g., malachite green, brilliant green, brilliant blue), and victoria blue dyes. Thiazine dyes contain a thiazine ring, which is a six-membered ring of four carbons, a nitrogen and a sulfur (e.g., methylene blue, phenothiazine, thiomorpholine). The colorant may be present in any amount suitable to impart the desired color to the disinfectant composition.

In some implementations, the at least one colorant of an indicator composition described here is soluble in a polar or nonpolar solvent, such as an alcohol or dichloromethane. In some implementations, the at least one colorant of an indicator composition described here is in the form of an emulsion in aqueous solution or non-aqueous solution (e.g., oil-in-water emulsions, water-in-oil emulsions, silicone-in-water emulsions, oil-in-silicone emulsions, water-in-silicone emulsions, and silicone-in-oil emulsions). Such emulsions of the colorant(s) are advantageous for combining a colorant that is insoluble or poorly water soluble, such as crystal violet lactone, with catalysts and optional additives that are also insoluble or poorly water soluble, such as occlusives, waxes, butters, and oils, but which provide desired color intensity and color-fading properties. In some implementations, the desired color intensity is dark enough to visibly see the color on dark surfaces (e.g., brown, navy blue, etc.) and the desired color-fading property is such that the intense color completely fades to colorless after a period of time, leaving behind no visible color residue after the indicator composition has evaporated from the surface. Further explanation of the optional additives and their advantages are described below.

In some implementations, where the catalyst forms a separate component of a multi-component indicator composition described here, the catalyst may be selected from a strong base, a weak base, a combination of strong and/or weak bases, a metal salt, a reducing agent, and an additional amount of a disinfectant composition, such as additional hydrogen peroxide. In some implementations, where the catalyst may form a separate component of a multi-component indicator composition described here, the catalyst may be selected from a strong base, a weak base, a combination of strong and/or weak bases, a metal salt, a reducing agent, an oxidizing agent, a strong acid, a weak acid, a combination of strong and/or weak acids, and an additional amount of a disinfectant composition, such as additional hydrogen peroxide. In some implementations, the catalyst may comprise a reactive oxygen species generating agent, for example, sodium nitrate, potassium nitrate, sodium nitrite, and titanium dioxide. In embodiments, the total amount of catalyst in the composition is 3-40% w/w, preferably 3-10% w/w, based on total weight of the composition. In embodiments, the ratio of catalyst to water-soluble pigment in the composition is from 0.005:1 to 20:1 or from 0.50:1 to 5:1. In some implementations, the indicator composition may comprise one or more catalysts.

In some implementations, the one or more catalysts comprises a strong base selected from potassium hydroxide (KOH), sodium hydroxide (NaOH), lithium hydroxide (LiOH), rubidium hydroxide (RbOH), cesium hydroxide (CsOH), calcium hydroxide (Ca(OH)$_2$), strontium hydroxide (Sr(OH)$_2$), magnesium hydroxide (Mg(OH)$_2$), and barium hydroxide (Ba(OH)$_2$), preferably KOH, NaOH, LiOH, or Ca(OH)$_2$.

In some implementations, the one or more catalysts comprises a weak base selected from a base having a pK$_b$ of less than 7, preferably any bicarbonate salt, any carbonate salt, methyl amine, hydroxides of quaternary ammonium cations or other organic cations, pyridine, aniline, imidazole, histidine, benzimidazole, a phosphazene base, and a nucleobase.

In some implementations, the one or more catalysts comprises a metal salt in which the metal salt has an oxidation state of +1, +2, or +3, preferably +2. In some implementations, the metal salt is an iron, copper, zinc, or magnesium salt, preferably an iron salt. In some implementations, the metal salt is a sulfate, nitrate, bromide, chloride, gluconate, sulfide, fumarate, oxide, iodide, fluoride, acetate, oxalate, stearate, diethyldithiocarbamate, ethoxide, citrate, trifluoromethanesulphonate, or cyanide salt. In some implementations, the metal salt is a sulfate, nitrate, bromide, chloride, or fluoride salt. In some implementations, the metal salt is anhydrous or hydrated, preferably a mono-, di-, tri-, penta-, hexa-, hepta-, nona-hydrate salt. In implementations where a weak metal salt catalyst is used, such as copper, zinc, or magnesium, the composition may further comprise an optional reducing agent which serves to replenish the metal catalyst by returning it to a lower oxidation state.

In some implementations, certain surfactants may act in a dual role as catalysts via the generation of hydroxyl radicals, for example, cetylmethylammonium bromide (CTAB).

In some implementations, a single or multi-component indicator composition described here may contain an optional surfactant or mixture of surfactants. In some implementations, the surfactant is selected from one or more of an anionic, nonionic, cationic, zwitterionic, amphoteric, or polymeric surfactant. In some implementations, the surfactant is selected from one or more of a nonionic surfactant, such as a polyglycol ether (e.g., Tergitol™), tetramethyl decynediol (Surfynol™) and cocomonoisopropanolamide (Ninol™ M10); an anionic surfactant such as alkyldiphenyloxide disulfonate (Dowfax™ 2A1), sodium lauryl sulfate (SLES), and Stepanol™ WA-100; a cationic surfactant such as hexadecyltrimethylammonium bromide (HTAB), which may also be referred to as cetylmethylammonium bromide (CTAB); a zwitterionic or amphoteric surfactant such as lauryldimethylamine N-oxide and cocoamidopropyl betaine; and a polymeric surfactant such as polysiloxane, cetyldimethicone copolyol, and poly-glycerol-poly-ricinolate. In some implementations, the surfactant is sodium xylene sulfonate (SXS) or sodium toluene sulfonate (STS). In some implementations, the surfactant is a mixture of SXS and STS.

In some implementations, where a surfactant may cause instability in the disinfectant composition, (e.g., HTAB), and in some implementations, where a surfactant may cause instability in the colorant composition, (e.g., SDS, SXS, SLES), it is especially advantageous to add the surfactant to the disinfectant and/or colorant composition only at the point of use, for example by inclusion in a single or multi-component indicator composition as described herein.

Further examples of anionic surfactants considered herein include, but are not limited to, sodium dodecyl sulfate (SDS), sodium dodecylbenzenesulfonate (SDBS), sodium cocyl glutamate, sodium lauryl glucose carboxylate, sodium alkane sulfonate, sodium myreth sulfate (SMS), sodium cholate, alkyldiphenyloxide disulfonate, 1,1'-oxybis-tetrapropylene derivatives, sulfonated, sodium salts (e.g., DOWFAX™ 2A1 blend), sodium toluene sulfonate (STS), alkylbenzene sulfonates, di-alkyl sulfosuccinate, sodium stearate, sodium cocoamphoacetate, sodium lauroyl lactylate, or combinations thereof. Further examples of nonionic surfactants considered herein include, but are not limited to, glycerin, polysorbate 20, polysorbate 80, n-octylpyrrolidinone, an acetylenic diol (e.g., Surfynol 104S), benzene, Brij 721, Triton X 100, Tergitol™ 15-S-15, Tergitol™ 15-S-20, Tergitol™ 15-S-9, Tergitol™ 15-S-30, glyceryl monostearate, glyceryl monooleate, lauryl glucoside, decyl glucoside, ceteareth-20, or combinations thereof. Further examples of cationic surfactants considered herein include, but are not limited to, benzalkonium chloride, octenidine dihydrochloride, or combinations thereof. In some implementations, the indicator composition includes a surfactant blend of decyl glucoside and sodium lauroyl lactylate. In some implementations, the indicator composition includes a surfactant blend of sodium cocoamphoacetate, glycerin, lauryl glucoside, sodium cocyl glutamate, and sodium lauryl glucose carboxylate. In some implementations, the indicator composition includes a mixture of different isopropanolamides of cocoamide.

In some implementations, a single or multi-component indicator composition described here may contain an optional rheology modifier or thickener. In some implementations, the indicator composition may comprise one or more rheology modifiers or thickeners. As with many additives, rheology modifiers or thickeners may cause the disinfectant solution to become unstable over time (e.g., rheology modifiers such as gums and polysaccharides are reducing sugars that react with oxidizers like hypochlorite, reducing the potency of the disinfectant), which is mitigated by inclusion of the rheology modifier or thickener into a single or multi-component indicator compositions as described herein, which is combined with the disinfectant composition at point of use, for example dispensed directly onto a disinfectant article, such as a wipe.

Examples of rheology modifiers or thickeners that may be used include lambda carrageenan, iota carrageenan, kappa carrageenan, sodium alginate, guar gum, glycerol or glycerin, dextran, cellulose, sorbitol, propylene glycol, lactic acid, lithium chloride, polydextrose, sodium polymetaphosphate, sodium polyacrylate, sodium chloride, glucose, agar, starches, gum arabic, pectin, gum polysaccharides, fumed silica, talc, and carbomer, butylene glycol, propanediol, lecithin, sorbeth-230 tetraoleate, decyl glucoside, sorbitan laurate, PEG-120 methyl glucose dioleate, methyl gluceth-10, corn starch, triethanolamine, carbomer 940, copolymers (e.g. octylacrylamide, polyacrylic acid, methylacrylic acid), glyceryl stearate, glucose-D, glucose-SORB, glyceryl oleate, or combinations thereof. In some implementations, the rheology modifier or thickener is glycerol or glycerin. In some implementations, the rheology modifier or thickener is chloride salts (e.g. sodium chloride), cetearyl alcohol, carbomers (e.g., carbomer 920), or combinations thereof. In some implementations, the rheology modifiers have the additional benefit of acting to fade the dye more quickly, thus allowing fade time to be controlled (e.g., acrylates/octylacrylamide copolymer), the additional benefit of acting as a humectant (e.g., glycerin), the additional benefit of acting as a surfactant (e.g., glyceryl mono oleate), the additional benefit of acting as an oil (e.g. cocamide), the additional benefit of acting as a pH adjuster (e.g., Carbomer™ 940), and the additional benefit of acting as an emulsifier (e.g., glyceryl stearate).

In some implementations, a single or multi-component indicator composition described here comprises a pH modulator in the form of an acidic agent which imparts an acidic pH to the aqueous solution of the component comprising it, for example a pH less than 7, preferably a pH less than 5, or a pH of about 3 or less. In some implementations, a mixture of pH modulators may be used. In accordance with any of the implementations comprising an acidic agent, the acidic agent may comprise a strong acid, a weak acid, an acidic buffer, or a combination thereof, for example a zwitterionic compound, a strong acid and weak acid, and/or a weak acid and a conjugate base. In some implementations, the strong acid is selected from one of or a combination of $H_2SO_4$, HCl, HBr, HI, $HClO_4$, $HClO_3$, or $HNO_3$, preferably $H_2SO_4$, $HNO_3$, and/or HCl. In some implementations, the weak acid is an acid having a $pK_a$ of less than 7, preferably weak ionic acids and organic acids, preferably any amino acids, citric acid, acetic acid, ascorbic acid, benzenesulfonic acid, benzoic acid, folic acid, and polyphosphoric acids, and derivatives thereof.

In some implementations, the pH modulator is selected from a basic agent such as methylamine, pyridine, diethylamine, hydroxylamine, hydrazine, aniline, aluminium hydroxide, sodium phosphate, sodium carbonate, sodium bicarbonate, triethanolamine, sodium tripolyphosphate, imidazole, aqueous ammonia, basic buffers with a pH between 7-14, and mixtures thereof. In some implementations, the pH modulator can also act as an agent to produce faster fading of our colorant additive, for example triethanolamine. In some implementations, the pH modulator can also act as a solubilizing agent, for example sodium carbonate. In some implementations, the pH modulator can also act as a corrosion inhibitor, for example, sodium carbonate. In some implementations, the pH modulator can act as a catalyst, for example sodium bicarbonate and sodium tripolyphosphate.

In some embodiments, it is desirable for the present invention to initially yield an intense color, such as a color that is intense enough to be visible on a dark surface such as dark stained wood, navy blue furniture, etc., and then completely fade away. In some implementations, certain optional additives can be used to improve color intensity and lengthen the color-fading reaction time, including foaming and foam-boosting agents, pearlizers, opacifying agents, stabilizers, vitamins, and antioxidants. By "completely fade away", it is intended that no visible color residue remains on the surface after a period of time, which may range from seconds to minutes, for example from 1 to 30 seconds to 1 to 60 minutes. This can be quantified in any number of ways, for example by defining a color residue or "streak" as a non-fading color residue pattern visible to the human eye that is of a certain size, for example larger than 1 square inch, and that is remaining on the surface after a period of time following application of the indicator composition and disinfectant.

The problem of color residue is particularly apparent on certain surfaces, especially more porous surfaces as compared to non-porous surfaces (e.g., wood compared to stainless steel) and surfaces having a texture that is not smooth, for example a texture that is bumpy or even sticky, as compared to smooth surfaces. For example, it is easier to achieve more consistent color-fading reaction times on smooth, hard, non-porous surfaces, such as stainless steel, than on a porous or semi-porous, bumpy, sticky material such as rubber. This is because, for example, the pores of the material may absorb the composition and/or a surface that is not smooth may cause uneven distribution of the composition and/or its components, such as catalysts and thickeners, altering the fading reaction and leading to incomplete fading of the colorant. In addition, not all surfaces share the same geometry, shape, or continuity, wherein edges of surfaces, cracks or valleys, holes, and the like may make uniform application of the indicator compositions difficult, resulting in failure of the colorant to completely fade.

In some implementations, where we define a "streak" to mean a non-fading color residue pattern larger than 1 square inch, a reference aqueous solution of 1% w/v FD&C Blue 1, leaves about 1-5 streaks on a textured, sticky rubber surface. The present inventors have found that including one or more optional additives in an indicator composition comprising the same amount of FD&C Blue 1, or similar colorant such as Acid Blue 1, substantially reduces the color residue, for example the indicator composition leaves only 0-3 or 0-2 or fewer streaks on the same surface, as compared to the reference solution. Thus, in some implementations it is desirable to include one or more optional additives in an indicator composition described here, the one or more optional additives selected from a humectant, an occlusive, a wax, a butter, an oil, a co-surfactant, a filler, a texturizer, an organic acid, an emollient, a foaming and foam-boosting agent, a pearlizer, an opacifying agent, a vitamin, an antioxidant, an anti-foaming agent, an emulsifying agent, a co-emulsifier, an emulsion stabilizer, a chelating agent, an anticaking agent, a moisture-absorbing agent, a silicone, a silicone conditioner, an antimicrobial agent and preservative, a stabilizer, a stabilizing salt, a corrosion inhibitor, a fragrance, an alkyl amine, an oleochemical, a polymer, a copolymer, and combinations or mixtures thereof. For example, an aqueous solution of FD&C Blue 1 and glycerin leaves about 0-3 streaks. The number of streaks is further reduced by the addition of a wax, decyl glucoside and sodium lauroyl lactylate, kaolin, malic acid, glycol stearate, and PEG-8 dimethicone, to about 0-2 streaks. Similarly, an aqueous solution of FD&C Blue 1, glycerin, decyl glucoside, and sodium lauroyl lactylate leaves about 0-2 streaks.

In some implementations, humectants, occlusives, waxes, butters, oils, co-surfactants, fillers, texturizers, organic acids, emollients, alkyl amines, oleochemicals, polymers, and copolymers can aid in the reduction of colored residue or improved uniformity in color fading reaction time. For example, humectants, such as glycerin, are able to attract moisture from the atmosphere, keeping a surface treated by the present invention in medium for longer, thereby providing a longer-lasting medium in which the color-fading reaction can go to completion. Occlusives, such as petrolatum, waxes, such as castor wax, butters, such as shea butter, oils, such as *Prunus armeniaca* kernel oil, all work similarly by providing a thin protective layer over the medium, slowing the evaporation rate and allowing the medium to remain on the surface for longer. Surfactants such as SDS have been empirically observed to decrease color residue on porous and textured surfaces, making co-surfactants, such as decyl glucoside and sodium lauroyl lactylate, advantageous given their ability to keep surfactants stable in the medium. In some instances, the color does not uniformly fade on a surface due to the presence of textures or cracks, crevices, and/or wrinkles in the surface that cause pooling and create nonuniform layers of the medium. Fillers, such as arrowroot starch, and texturizers, such as kaolin, can modify the surface tension to prevent the medium from pooling. Organic acids, such as malic acid, may be used for the purpose of not changing the pH of the solution, but rather to prime the surface by smoothing surfaces. Emollients, such as glycol stearate and PEG-8 dimethicone, form a film barrier similar to occlusives and can also act as fillers and texturizers to smooth rough surfaces. Alkyl amines, such as triethanolamine, oleochemical, such as oleamide DEA and cocamide MEA, polymers, such as polyacrylate, and copolymers, such as acylates/octylacrylamide copolymer, all chemically react with an oxidizer, such as a hypochlorite disinfectant, to create a more oxidative species to speed up the color-fading reaction and prevent color residue. On a textured, sticky rubber surface, an indicator composition comprising FD&C Blue 1 and glycerin may leave about 0-3 streaks; FD&C Blue 1, glycerin, wax, SDS, decyl glucoside, sodium lauroyl lactylate, kaolin, malic acid, glycol stearate, and PEG-8 dimethicone may leave about 0-2 streaks; FD&C Blue 1, glycerin, decyl glucoside, and sodium lauroyl lactylate may leave about 0-2 streaks; FD&C Blue 1, cetearyl alcohol, PEG-8 dimethicone, and glycerin may leave about 0-2 streaks; FD&C Blue 1, tartaric acid, propylene glycol, and glyceryl mono oleate may leave about 0-2 streaks; FD&C Blue 1, triethanolamine, and cocamide MEA may leave about 0-2 streaks.

The optional additives that improve color-fading may increase the rate of color-fading or reduce the color intensity of an indicator composition described here. In some implementations, foaming and foam-boosting agents, pearlizer, opacifying agents, stabilizers, vitamins, and antioxidants, can be used to improve color intensity and lengthen the color-fading reaction time. Foaming and foam-boosting agents, such as castile soap and ammonium lauryl sulfate, empirically makes the color more visible. Pearlizers, such as bismuth oxychloride and glycol distearate, allow the color to be more reflective on surfaces, thus enhancing its visibility. Opacifying agents, such as titanium dioxide, titanium dioxide nanopowder, and mica, provides a base or body to the color making it look less translucent. Vitamins, such as vitamin E, and antioxidants, such as butylated hydroxytoluene, can react with the catalyst or the oxidizer and slow the rate of the reaction, allowing the color-fading time to take longer. For example, an indicator composition comprising FD&C Blue 1 may fade in about 2-4 minutes, while an indicator composition comprising FD&C Blue 1, ammonium lauryl sulfate, glycol distearate, vitamin E, and titanium dioxide nanopowder appears visibly darker and may fade in color completely in about 4-12 minutes. In some implementations, an anti-foaming agent, such as glycerin, propylene glycol, and cyclo-dimethicone, can be used to reduce excessive effervescence or foaminess of the foaming or foam-boosting agent.

Some of the optional additives, such as opacifying agents like titanium dioxide and mica, may not be readily soluble in a water based medium, resulting in uneven or inconsistent application on surfaces or clogging of the device 400. Accordingly, in some implementations, emulsifying agents, co-emulsifiers, emulsion stabilizers, chelating agents, and anticaking agents may be included in the indicator composition. Emulsifying or dispersing agents, such as PEG-8 dimethicone, dimethicone phosphates, polysorbates, polyacrylates and polyphosphates may be used to create emulsions and microemulsions that disperse and suspend desired non-polar or insoluble additives. Co-emulsifiers, such as cetearyl alcohol, boric acid, and cetyl alcohol, may improve the viscosity and stability of the resultant emulsion. Emulsion stabilizers, such as polyelectrolytes, similarly maintain the stability of the emulsion and prevent polar and non-polar additives from reforming separate layers in the medium. Chelating agents, such as EDTA, may bind with metal compounds to form a stable solution that does not separate. Anticaking agents, such as calcium stearate and magnesium stearate, may prevent lumps from forming in solution, such as when a non-polar additive is added to a polar solvent, preventing dissolution and maintaining homogeneity of the solution. For example, an indicator composition comprising FD&C Blue 1 and titanium dioxide may clog the device 400 in about 10-50% of uses and lead to settling of titanium dioxide after 3 hours, while an indicator composition comprising FD&C Blue 1, titanium dioxide, PEG-8 dimethicone, sodium polyacrylate, cetyl alcohol, polyelectrolytes, EDTA, and magnesium stearate is less likely to clog the device 400 and prevent any settling of titanium dioxide.

In some embodiments, the addition of an optional additive to the indicator composition, such as wax or glycerin, may leave behind an oily residue on the surface which is undesirable to the user. Moisture-absorbing agents, such as PEG-400 stearate and corn starch, may be used to bind to oily or waxy compounds. For example, an indicator composition comprising FD&C Blue 1 and wax may leave behind a visible oily film, while an indicator composition comprising FD&C Blue 1, wax, and corn starch may not leave behind any visible residue.

In some implementations, silicones, such as PEG/PPG-20/23 dimethicone, PEG/PPG-23/6 dimethicone, PEG/PPG 18-18 dimethicone, and PEG/PPG 15-15 dimethicone, may be used as an emulsifying agent, anticaking agent, emulsion stabilizer, or surfactant given its properties as a film former, slip modifier, and surface modifier. Silicone conditioners, such as dimethicone satin, help silicones remain stable and solubilized in the medium.

In some implementations, antimicrobial agents and preservatives, such as acrylic acid copolymer, phenoxyethanol, and iodopropynyl butacarbamate, are advantageous when the medium is water-based, being conducive to growth of unwanted organisms that may interfere in the color-changing reaction or are otherwise undesirable for use in healthcare settings. For example, an indicator composition comprising FD&C Blue 1 and vitamin E may have a usable shelf life of about 6 months, while an indicator composition comprising FD&C Blue 1, vitamin E, phenoxyethanol, and iodopropynyl butacarbamate may have a usable shelf life of about 12 months or longer.

In some implementations, stabilizers, such as tris(2,4-di-tert-butylphenyl)phosphite and hindered amine light stabilizers (HALS), and stabilizing salts, such as trisodium citrate, monosodium phosphate, and disodium phosphate, are advantageous to preserve the stability of fragile additives, such as structurally delicate colorants (e.g., crystal violet lactone), and protect components of the product from aging and weathering. For example, an indicator composition comprising crystal violet lactone in an alcohol based solvent may only remain colored for about less than 1 minute, while an indicator composition comprising crystal violet lactone, tris(2,4-di-tert-butylphenyl)phosphite, and trisodium citrate in an alcohol based solvent may remain colored for about 10 minutes.

In some implementations, a corrosion inhibitor, such as sodium carbonate or FD&C Blue 1, may be desirable for reducing corrosion on surfaces such as finished wood, to prevent the surface from losing texture or coating and subsequently turning from non-porous to semi-porous. For example, a sodium hypochlorite wipe may cause severe corrosion at a rate of greater than 5 mpy over a month on stainless steel, while a sodium hypochlorite wipe with FD&C Blue 1 and sodium carbonate may cause negligible corrosion at a rate of less than 2 mpy over a month on stainless steel.

In some implementations, a fragrance or perfume, such as *Citrus grandis* seed extract, may be used to mask the harsh smell of the disinfectant, such as bleach, making the product easier to use.

The examples above are used illustratively and are not limiting. Further examples of each of the optional additives are included below.

In some implementations, a single or multi-component indicator composition described here may contain one or more optional humectants. In some implementations, the humectant is glycerin or glycerol.

In some implementations, a single or multi-component indicator composition described here may contain one or more optional occlusives. In some implementations, the occlusive is selected from petrolatum, lanolin, argan oil, safflower oil, mineral oil, olive oil, jojoba oil, or combinations thereof.

In some implementations, a single or multi-component indicator composition described here may contain one or more optional waxes. In some implementations, the wax is selected from castor wax, bees wax, candelilla wax, carnauba wax, lanolin alcohol, lauryl laurate, PEG-8 beeswax, polyhydroxystearic acid, sunflower wax, ozokerite wax, microcrystalline wax, tribehenin, or combinations thereof.

In some implementations, a single or multi-component indicator composition described here may contain one or more optional butters. In some implementations, the butter is selected from avocado butter, cocoa butter, green tea butter, shea butter, mango butter, or combinations thereof.

In some implementations, a single or multi-component indicator composition described here may contain one or more optional oils. In some implementations, the oil is selected from *Prunus armeniaca* kernel oil, *Prunus amygdalus dulcis* oil, *Borago officinalis* oil, or combinations thereof.

In some implementations, a single or multi-component indicator composition described here may contain one or more optional co-surfactants, whose purpose is to complement surfactants in any way necessary (i.e., help dissolve a surfactant). In some implementations, the co-surfactant is selected from glyceryl mono oleate, decyl glucoside, glyceryl monostearate, or combinations thereof. In some implementations, the co-surfactant is 0.005%-50% undefined blend of decyl glucoside and sodium lauroyl lactylate.

In some implementations, a single or multi-component indicator composition described here may contain one or more optional fillers. In some implementations, the filler is selected from mica powder, tapioca starch polymethylsilsesquioxane, LiPeptide, isohexadecane, ethylene/propylene/styrene copolymer, butylene/ethylene/styrene copolymer, sodium hyaluronate, xanthan gum, phenoxyethanol, tripeptide-1, magnesium hydroxide, or combinations thereof.

In some implementations, a single or multi-component indicator composition described here may contain one or more optional texturizers. In some implementations, the texturizer is selected from arrowroot starch, bentonite, bismuth oxychloride, charcoal powder, colloidal oatmeal, dead sea mud, hydroxypropyl starch phosphate, kaolin, *Oryza sativa*, or combinations thereof.

In some implementations, a single or multi-component indicator composition described here may contain one or more optional organic acids. In some implementations, the organic acid does not affect or maintain the pH of the solution. In some implementations, the organic acid is selected from acids with carboxylic or sulfonic groups, such as malic acid, tartaric acid, lactic acid, and butyric acid, and combinations of any of the foregoing.

In some implementations, a single or multi-component indicator composition described here may contain one or more optional emollients. In some implementations, the emollient is selected from cyclopentasiloxane, dimethicone, dimethicone coated titanium dioxide, isododecane, phenyltrimethicone, alcohol benzoates, isononyl isononanoate, PEG-8 dimethicone, octyldodecanol, PEG-8 dimethicone meadowfoamate, cetyl palmitate, naturally-derived oils (e.g. borage seed oil, *Prunus armeniaca* kernel oil, grape seed oil, apricot kernel oil, avocado oil, argan oil, apple seed oil, squalene oil), or combinations thereof.

In some implementations, a single or multi-component indicator composition described here may contain one or more optional foaming or foam-boosting agents. In some implementations, the foaming agents is selected from castile soap, ammonium lauryl sulfate, cocamidopropyl hydroxysultaine, glycerin, cocamidopropylamine oxide, cocamidopropyl betaine, or combinations thereof.

In some implementations, a single or multi-component indicator composition described here may contain one or more optional pearlizers. In some implementations, the pearlizer is selected from glycol distearate, bismuth oxychloride, and combinations thereof.

In some implementations, a single or multi-component indicator composition described here may contain one or more optional opacifying agents. In some implementations, the opacifying agent is selected from transition metal oxides, both in regular form and in nanopowder form (e.g. TiO2 (titanium dioxide), ZnO (zinc oxide)), glyceryl monostearate, dimethicone coated titanium dioxide, glycol distearate, micas (e.g. sericite mica, white sericite mica, silk mica, pearl white mica), or combinations thereof.

In some implementations, a single or multi-component indicator composition described here may contain one or more optional vitamins. In some implementations, the vitamin is selected from retinol, phytonadione, menaquinone, ascorbic acid, ascorbate salts, thiamin, riboflavin, niacin, niacinamide pyridoxine, cyanocobalamin, folic acid, biotin, pantothenic acid, ergocalciferol, cholecalciferol, tocopherols, tocotrienols, phylloquinone, hydroxocobalamin, adenosylcobalamin, methylcobalamin, carotenoids, or combinations thereof.

In some implementations, a single or multi-component indicator composition described here may contain one or more optional antioxidants. In some implementations, the antioxidant is selected from butylated hydroxytoluene, beta carotene, or combinations thereof.

In some implementations, a single or multi-component indicator composition described here may contain one or more optional anti-foaming agents. In some implementations, the anti-foaming agent is glycerin, propylene glycol, cyclomethicone, dimethicone, or combinations thereof.

In some implementations, a single or multi-component indicator composition described here may contain one or more optional emulsifying agents. In some implementations, the emulsifying agent is selected from sodium phosphate (e.g. monosodium phosphate, sodium tripolyphosphate), dimethicone copolyols (e.g. PEG/PPG-18/18 dimethicone), stearic acid, polyglyceryl-4 isostearate, triethanolamine, ceteareth-25, cetearyl alcohol, sodium lauroyl lactylate, alcohol (e.g. propanol, ethanol, 1-decanol), denatured alcohol, ceteareth-20, PEG-100 stearate, PEG-400 stearate, isopropanolamides of coconut acid (cocamide MIPA), sorbitan stearate, non-foaming emulsifying wax, sorbitan salts (e.g. sorbitan olivate), cetearyl salts (e.g. cetearyl olivate), 2-phenoxyethanol, polyhydroxystearic acid, polyglyceryl-6 polyricinoleate, or combinations thereof.

In some implementations, a single or multi-component indicator composition described here may contain one or more optional co-emulsifiers. In some implementations, the co-emulsifier is boric acid, cetyl alcohol, cetearyl alcohol, or combinations thereof.

In some implementations, a single or multi-component indicator composition described here may contain one or more optional emulsion stabilizers. In some implementations, the emulsion stabilizer is selected from dimethicone copolyols (e.g. PEG/PPG-20/23 dimethicone, PEG/PPG-23/6 dimethicone), chloride salts (e.g. sodium chloride, potassium chloride), disteardimonium hectorite, polyethylene, fumed silica, magnesium sulfate, or combinations thereof.

In some implementations, a single or multi-component indicator composition described here may contain one or more optional chelating agents. In some implementations, the chelating agent is selected from EDTA salts (e.g., disodium EDTA), phosphonates, citric acid, or combinations thereof.

In some implementations, a single or multi-component indicator composition described here may contain one or more optional anticaking agents. In some implementations, the anticaking agent is selected from dimethicone copolyols (e.g., PEG/PPG-15/15 dimethicone), corn starch, or combinations thereof.

In some implementations, a single or multi-component indicator composition described here may contain one or more optional moisture-absorbing agents. In some implementations, the moisture-absorbing agent is selected from corn starch, talc, or combinations thereof.

In some implementations, a single or multi-component indicator composition described here may contain one or more optional silicones. In some implementations, the silicone is selected from amodimethicone, a dimethicone, or a combination thereof.

In some implementations, a single or multi-component indicator composition described here may contain one or more optional silicone conditioners. In some implementations, the silicone conditioner is dimethicone satin.

In some implementations, a single or multi-component indicator composition described here may contain one or more optional antimicrobial agents or preservatives. In some implementations, the antimicrobial agent or preservative is selected from 2-phenoxyethanol, benzyl alcohol, caprylyl glycol, ethylhexyl glycerin, hexanediol, EDTA salts (e.g., disodium EDTA), parabens (e.g., methylparaben, propylparaben), iodopropynyl butacarbamate, or combinations thereof.

In some implementations, a single or multi-component indicator composition described here may contain one or more optional stabilizers. In some implementations, the stabilizer is selected from EDTA, sodium gluconate, butylated hydroxytoluene, or combinations thereof.

In some implementations, a single or multi-component indicator composition described here may contain one or more optional stabilizing salts. In some implementations, the stabilizing salt is selected from sodium sulfate, magnesium chloride, sodium chloride, potassium chloride, or combinations thereof.

In some implementations, a single or multi-component indicator composition described here may contain an optional corrosion inhibitor, or a mixture of corrosion inhibitors. In some implementations, the corrosion inhibitor is selected from sodium carbonate, calcium chloride, zinc chloride, sodium polyacrylate, silicate, benzimidazole, benzotriazole, calcium succinate, calcium sulfate, ascorbic acid, glucaric acid, gluconic acid, zinc sulfate, cerium chloride, sodium chromate, nitrates, phosphates, magnesium salts, nickel salts, calcium salts, succinic acid, tryptamine, and mercaptobenzothiazole or combinations thereof. In some implementations, the colorant itself may act as a corrosion inhibitor, for example the dye, FD&C Blue #1, can be used as the anti-corrosion or corrosion inhibitor. In addition, pH modifiers such as acids and bases, can be added as anti-corrosion agents or corrosion inhibitors.

In some implementations, a single or multi-component indicator composition described here may contain one or more optional perfumes or fragrances. In some implementations, the perfume or fragrance is selected from citric acid, anise oil, pinene, bay leaf oil, benzoic acid, acetic acid, camphor oil, florex, geranium oil, grapefruit oil, juniper lactone, lemon oil, myristic oil, orange oil terpenes, *Citrus grandis* seed extract, sandalwood, and vanillin, or combinations thereof.

In some implementations, a single or multi-component indicator composition described here may contain one or more optional alkyl amines. In some implementations, the alkyl amine is selected from triethanolamine, diethanolamine, triethylamine, methylamine, or combinations thereof.

In some implementations, a single or multi-component indicator composition described here may contain one or more optional oleochemicals. In some implementations, the oleochemical is selected from cocamide DEA, oleamide DEA, lauramide DEA, linoleamide DEA, or combinations thereof.

In some implementations, a single or multi-component indicator composition described here may contain one or more optional polymers. In some implementations, the polymer is selected from polyacrylic acid, polyvinylamides, polyacrylates, polymethacrylates, and cross-linked polymers (e.g., ethers of pentaerythritol, divinylbenzene), or combinations thereof.

In some implementations, a single or multi-component indicator composition described here may contain one or more optional copolymers. In some implementations, the copolymer is selected from acylates/octylacrylamide copolymer, acrylates/steareth-20 methacrylate copolymer, or combinations thereof.

In embodiments where disinfectants are included in the single or multi-component indicator composition, examples of disinfectants include sodium hypochlorite, calcium hypochlorite, sodium dichloroisocyanurate, didecyldimethylammonium chloride, chlorhexidine gluconate, a phenol, an aldehyde, a terpene, hydrogen peroxide, chlorine dioxide, a peroxy and peroxo acid such as peracetic acid, a quaternary ammonium compound, an inorganic compound such as metals and acids, and alcohols such as ethanol and isopropyl alcohol. These disinfectant compositions may be combined with or separated from other components as described here in a single or multi-chamber article of manufacture. Disinfectant compositions may also come from a disinfectant article of manufacture. In embodiments, disinfectant compositions contained within single or multi-chamber articles of manufacture may be added to the same or different disinfectant compositions contained on a disinfectant article of manufacture. In some embodiments, adding the same disinfectant composition onto a disinfectant article of manufacture is advantageous to provide a different indicator composition to disinfectant composition ratio, as described further below.

The present disclosure includes indicator compositions diluted in disinfectant compositions. The disinfectant composition may come from a disinfectant article of manufacture or may be contained in a single or multi-chamber article of manufacture. The ratio of indicator composition to disinfectant composition ranges from 0.0001:1 to 10:1, including, but not limited to, 0.001:1, 0.01:1, 0.1:1, 0.5:1, 1:1, 2:1, 5:1, and 10:1.

In some implementations, where the indicator composition is a multi-component composition, the colorant is preferably contained in a separate component from the catalyst, for example in a separate compartment or reservoir of an article of manufacture comprising the multi-component composition. It is generally undesirable to include colorants in the same component with either reducing agents, oxidizing agents, a base, or a strong metal catalyst. However, in some implementations, the colorant may be contained in the same component with a weak metal salt, such as a $Cu^I$ salt. In implementations where the catalyst comprises an iron salt, the component comprising the iron salt preferably further comprises a pH modulator, such as an acid, sufficient to maintain the iron salt in an acidic aqueous environment. In implementations where the catalyst of a multi-component composition comprises a reducing agent and a surfactant, preferably the reducing agent and surfactant are contained in the same component of the composition, for example in the same compartment or reservoir of an article of manufacture comprising the multi-component composition. In implementations where the catalyst comprises both a reducing agent and an oxidizing agent, the oxidizing and reducing agents are preferably contained in two separate components, for example in two separate compartments or reservoirs of an article of manufacture comprising the multi-component composition.

In some implementations, and as described above, the disclosure provides a device for use with the multi-component indicator compositions described here. The device may comprise a reservoir having at least two separate compartments, optionally having 2, 3, or 4 separate compartments, further optionally having more than 4 separate compartments, at least one applicator element comprising an automatic or manual mechanism, for example a spray mechanism, and a pump element, for example one that pumps an amount of the contents of each of the separate compartments towards either a further compartment in which they are mixed, or to the applicator element where they are mixed simultaneously with dispensing from the device. In some implementations, the device is actuated when a user pushes on an actuator such as a lever, button, or other mechanism, which mechanism may be manual or automatic.

In some implementations, the disclosure provides an article of manufacture comprising a multi-component indicator composition described here, in which the article of manufacture comprises separate compartments for each component of the multi-component indicator composition and is optionally adapted to work with, or within, a device as described here.

Indicator compositions adapted for use with various disinfectant compositions, including hypochlorite and troclosene based disinfectants, quaternary ammonium and alcohol based disinfectants, hydrogen peroxide based disinfectants, and peracetic acid based disinfectants, are described in more detail in the following sections.

Indicator Compositions for Hypochlorite and Troclosene Based Disinfectants

In some implementations, the disclosure provides a single or multi-component indicator composition adapted for use with hypochlorite and troclosene based disinfectant compositions. For example, the indicator composition may consist of two, three, four or more separate components which are combined at the point of use, for example using a device described herein. In some implementations, the multi-component composition comprises at least two separate components, the first component comprising a disinfectant composition in the form of an aqueous solution of sodium dichloroisocyanurate ("NaDCC" also referred to as "troclosene") or a disinfectant composition in the form of an aqueous solution of a metal salt of hypochlorous acid, for example sodium or calcium hypochlorite (NaOCl or $Ca(OCl)_2$), optionally comprising a pH modulator sufficient to maintain an alkaline pH of about 10-11; and the second component comprising at least one colorant and an acidic agent or acidifying agent as a pH modulator sufficient to maintain the pH of the second component at a pH of about 4-5, optionally a pH of between 4 and 7; and further optionally comprising one or more additives selected from a surfactant or mixture of surfactants, a rheology modifier, a stabilizer or corrosion inhibitor, a solubilizing agent, an antimicrobial agent, an opacifying agent, and a perfume or fragrance, as additives in either the first or second components, or both, or optionally as a third aqueous component comprising the one or more additives. In some implementations, the one or more additives may be selected from one or more of a surfactant, rheology modifier or thickener, a humectant, an occlusive, a wax, a butter, an oil, a co-surfactant, a filler, a texturizer, an organic acid, an emollient, a foaming and foam-boosting agent, a pearlizer, an opacifying agent, a vitamin, an antioxidant, an anti-foaming agent, an emulsifying agent, a co-emulsifier, an emulsion stabilizer, a chelating agent, an anticaking agent, a moisture-absorbing agent, a silicone, a silicone conditioner, an antimicrobial agent and preservative, a stabilizer, a stabilizing salt, a corrosion inhibitor, a fragrance, an alkyl amine, an oleochemical, polymers, copolymers, and mixtures of two or more of any of the foregoing, as additives in either the first or second components, or both, or optionally as a third aqueous component comprising the one or more additives.

In one implementation, a device for use with the multi-component indicator compositions described here comprises two separate compartments, the first compartment comprising a disinfectant composition in the form of an aqueous solution of sodium dichloroisocyanurate ("NaDCC" also referred to as "troclosene") or a disinfectant composition in the form of an aqueous solution of a metal salt of hypochlorous acid, for example sodium or calcium hypochlorite (NaOCl or Ca(OCl)$_2$), optionally comprising a pH modulator sufficient to maintain an alkaline pH of about 10-11; and the second compartment comprising at least one colorant and an acidic agent as a pH modulator sufficient to maintain the pH of the component in the second compartment at a pH of about 4-5; and further optionally comprising one or more of a surfactant or mixture of surfactants, a rheology modifier, a buffering agent, a stabilizer or a corrosion inhibitor, a solubilizing agent, an antimicrobial agent, an opacifying agent, and a perfume or fragrance, in either the first or second compartments. In some implementations the acidic component may be formed from citric acid, benzoic acid, acetic acid, and mixtures thereof. In some implementations, the composition may optionally comprise one or more of a surfactant, a rheology modifier, a humectant, an occlusive, a wax, a butter, an oil, a co-surfactant, a filler, a texturizer, an organic acid, an emollient, a foaming and foam-boosting agent, a pearlizer, an opacifying agent, a vitamin, an antioxidant, an anti-foaming agent, an emulsifying agent, a co-emulsifier, an emulsion stabilizer, a chelating agent, an anticaking agent, a moisture-absorbing agent, a silicone, a silicone conditioner, an antimicrobial agent and preservative, a stabilizer, a stabilizing salt, a corrosion inhibitor, a fragrance, an alkyl amine, an oleochemical, polymers, copolymers or a mixture of two or more of any of the foregoing, in either the first or second compartments.

Preferably, the components of a multi-component composition are provided separately, e.g., in separate chambers of a cartridge as described above, specifically when their combination before use would otherwise result in degradation of one or more of the components or the composition itself, such as by unfavorable precipitation of one or more of the components or oxidation of one or more of the components. For example, where the point of use composition comprises a disinfectant that is a strong oxidizer, such as sodium hypochlorite or hydrogen peroxide, a colorant such as Acid Blue 1, and a combination of cationic and anionic surfactants such as sodium mono oleate and hexadecyltrimethylammonium bromide (HTAB), it is advantageous to keep the colorant separate from the disinfectant, since upon their combination the colorant will fade. In addition, the combination of cationic and anionic surfactants is likely to result in undesirable precipitation of the surfactants over time, making it advantageous to keep them separate until they are combined for use. Certain thickeners are also advantageously stored separately, such as PEG-400 and glyceryl stearate, which may precipitate when combined. To illustrate this specific example, the multi-chambered cartridge would contain sodium hypochlorite in one chamber, Acid Blue 1 and sodium mono oleate in a second separate chamber, and HTAB in a third separate chamber.

In some implementations, the disinfectant composition is selected from sodium hypochlorite, calcium hypochlorite, and troclosene sodium, in amounts ranging from 0.05%-20%, preferably 0.1-5%, or 0.4-2%.

In some implementations the acidic agent or the acidifying agent may comprise citric acid, benzoic acid, acetic acid, such as glacial acetic acid, 5% acetic acid, and mixtures thereof. Other suitable acids can be used including for example hydrochloric, sulfuric, ascorbic, nitric, hydrobromic, perchloric, chloric, hydrofluoric, formic, nitrous, phosphoric, oxalic, vinegar, peracetic, boric, carbonic, ethanoic, and tartaric acids. In some implementations, the indicator composition in the dispensing cartridge 413 comprises an additive in the form of an acidic agent or acidifying agent as described herein.

In some implementations, the pH modulator sufficient to maintain an alkaline pH of the disinfectant composition comprises an alkaline builder, for example one or more of sodium hydroxide (NaOH), calcium hydroxide (Ca(OH)$_2$), potassium hydroxide (KOH), lithium hydroxide (LiOH), and mixtures thereof.

In some implementations, the at least one colorant of the indicator composition is a water-soluble oxidizable dye, preferably selected from an azo dye, a triarylmethane dye, a cationic dye, an anionic dye, a thiazine dye, and a leuco dye. In some implementations, the colorant is selected from FD&C Blue 1, Acid Blue 1, Direct Blue 1, Acid Green 50, Acid Green 25, Patent Blue V, FD&C Yellow 6, Fast Green FCF, Indigo Carmine, Acid Blue 80, Remazol Brilliant Blue R, Coomassie Brilliant Blue, Crystal Violet Lactone, Thymolphthalein, Bromothymol Blue, Methylene Blue, FD&C Red 2, and mixtures thereof. In some implementations, the colorant is FD&C Blue 1, Acid Blue 1, or Acid Green 50. In some implementations, the colorant is FD&C Blue 1. Generally, the amount of the colorant may range from about 0.01%-25% w/v, based on the volume of the disinfectant solution to be colored, preferably about 0.05-2%, or about 0.1%-1%, or about 0.1%-0.5%, depending on the particular colorant and strength of the disinfectant composition, as well as the desired strength of the initial color and desired fade time of the colored disinfectant following its application to a surface. For example, in some implementations the colorant is 0.1%-0.5% FD&C Blue 1, or 0.1%-1% FD&C Blue 1, Acid Blue 1, or Acid Green 50.

In some implementations, the one or more optional surfactants may be selected from sodium dodecyl sulfate (SDS), sodium xylene sulfonate (SXS), sodium laureth sulfate (SLES), sodium myreth sulfate (SMS), sodium cholate, an acetylenic diol (e.g., Surfynol™ 104S), glyceryl monostearate, glyceryl monooleate, sodium stearate, sodium cocoamphoacetate, lauryl glucoside, sodium cocoyl glutamate, sodium lauryl glucose carboxylate, decyl glucoside, sodium lauroyl lactylate, ceteareth-20, HTAB, benzene, 1,1'-oxybis-tetrapropylene derivatives, sulfonated, sodium salts (e.g., DOWFAX™ 2A1 blend), and sodium toluene sulfonate (STS), and mixtures thereof; the optional stabilizer or corrosion inhibitor may be selected from sodium chloride, sodium chlorate, sodium polyacrylate, sodium carbonate, lauramine oxide, and sodium orthosilicate; and the perfume or fragrance may be selected from citric acid, anise oil, pinene, bay leaf oil, benzoic acid, acetic acid, camphor oil, florex, geranium oil, grapefruit oil, juniper lactone, lemon oil, myristic oil, orange oil terpenes, *Citrus grandis* seed extract, sandalwood, and vanillin, or combinations thereof.

In some implementations, the one or more optional rheology modifiers is selected from sodium alginate, glycerin, glycerol, guar gum, locust bean, dextran, cellulose, carrageenan (lambda, iota, kappa), sodium carbonate, fumed silica, alkali swellable emulsions (ASE), hydrophobically modified alkali swellable emulsions (HASE), hydrophobically modified polyurethanes (HEUR), hydrophobically modified polyethers (HMPE), inorganic rheology modifiers (attapulgites), castor oil based thixotropes, sodium polyacrylate, ethylene glycol, propylene glycol, butylene glycol, propanediol, lecithins, orbeth-230 tetraoleate, PEG-120 methyl glucose dioleate, methyl gluceth-10, corn starch, triethanolamine, and mixtures thereof. In embodiments, the rheology modifier is glycerin or lambda carrageenan. The rheology modifier may generally be present in an amount of from about 0.05-5 wt %, or from 0.2-0.4 wt % e.g., for lambda carrageenan, or from 1-5% for glycerin.

In some implementations, the one or more optional rheology modifiers is selected from a polymer, a copolymer, and mixtures thereof. In some implementations, the polymer or copolymer is selected from one or more of a polyvinyl carboxy polymer crosslinked with ethers of pentaerythritol (e.g., Carbomer™ 940), an octylacrylamide/acrylates copolymer, a poly(acrylic acid) copolymer including copolymers of differing molecular weights comprised of monomers of octylacrylamide, acrylic acid, methyl acrylic acid, and other acrylates. In some implementations, the rheology modifiers have the additional benefit of acting to fade the dye more quickly, thus allowing fade time to be controlled (e.g., acrylates/octylacrylamide copolymer), the additional benefit of acting as a humectant (e.g., glycerin), the additional benefit of acting as a surfactant (e.g., glyceryl mono oleate), the additional benefit of acting as an oil (e.g. cocamide), the additional benefit of acting as a pH adjuster (e.g., Carbomer™ 940), and the additional benefit of acting as an emulsifier (e.g., glyceryl stearate).

In some implementations, the one or more optional rheology modifiers is selected from glycerin, glyceryl stearate, glyceryl oleate, chloride salts (e.g., magnesium chloride, sodium chloride), cetearyl alcohol, carbomers (e.g., Carbomer™ 940), and mixtures thereof.

In some implementations, the one or more optional humectants is glycerin or glycerol.

In some implementations, the one or more optional occlusives is selected from petrolatum, lanolin, olive oil, jojoba oil, or combinations thereof.

In some implementations, the one or more optional waxes is selected from castor wax, bees wax, candelilla wax, carnauba wax, lanolin alcohol, lauryl laurate, PEG-8 beeswax, polyhydroxystearic acid, sunflower wax, ozokerite wax, microcrystalline wax, tribehenin, or combinations thereof.

In some implementations, the one or more optional butters is selected from avocado butter, cocoa butter, green tea butter, shea butter, mango butter, or combinations thereof.

In some implementations, the one or more optional oils is selected from *Prunus armeniaca* kernel oil, *Prunus amygdalus dulcis* oil, *Borago officinalis* oil, or combinations thereof.

In some implementations, the one or more optional co-surfactants is selected from glyceryl mono oleate, decyl glucoside, glyceryl monostearate, or combinations thereof.

In some implementations, the one or more optional fillers is selected from mica powder, tapioca starch polymethylsilsesquioxane, LiPeptide, isohexadecane, ethylene/propylene/styrene copolymer, butylene/ethylene/styrene copolymer, sodium hyaluronate, xanthan gum, phenoxyethanol, tripeptide-1, magnesium hydroxide, or combinations thereof.

In some implementations, the one or more optional texturizers is selected from arrowroot starch, bentonite, bismuth oxychloride, charcoal powder, colloidal oatmeal, dead sea mud, hydroxypropyl starch phosphate, kaolin, *Oryza sativa*, or combinations thereof.

In some implementations, the one or more optional organic acids is selected from acids with carboxylic or sulfonic groups, such as malic acid and butyric acid.

In some implementations, the one or more optional emollients is selected from cyclopentasiloxane, dimethicone, dimethicone coated titanium dioxide, isododecane, phenyltrimethicone, alcohol benzoates, isononyl isononanoate, PEG-8 dimethicone, octyldodecanol, PEG-8 dimethicone meadowfoamate, cetyl palmitate, naturally-derived oils (e.g. borage seed oil, *Prunus armeniaca* kernel oil, grape seed oil, apricot kernel oil, avocado oil, argan oil, apple seed oil, squalene oil), or combinations thereof.

In some implementations, the one or more optional foaming agents is selected from castile soap, ammonium lauryl sulfate, cocamidopropyl hydroxysultaine, glycerin, cocamidopropylamine oxide, cocamidopropyl betaine, or combinations thereof.

In some implementations, the one or more optional pearlizer is glycol distearate.

In some implementations, the one or more optional opacifying agents is selected from transition metal oxides, both in regular form and in nanopowder form e.g., titanium dioxide ($TiO_2$), zinc oxide (ZnO), glyceryl monostearate, dimethicone coated titanium dioxide, glycol distearate, micas (e.g., sericite mica, white sericite mica, silk mica, pearl white mica), or combinations thereof.

In some implementations, the one or more optional vitamins is selected from retinol, phytonadione, menaquinone, ascorbic acid, ascorbate salts, thiamin, riboflavin, niacin, niacinamide pyridoxine, cyanocobalamin, folic acid, biotin, pantothenic acid, ergocalciferol, cholecalciferol, tocopherols, tocotrienols, phylloquinone, hydroxocobalamin, adenosylcobalamin, methylcobalamin, carotenoids, or combinations thereof.

In some implementations, the one or more optional antioxidants is selected from butylated hydroxytoluene, beta carotene, or combinations thereof.

In some implementations, the one or more optional antifoaming agents is glycerin, propylene glycol, cyclomethicone, dimethicone, or combinations thereof.

In some implementations, the one or more optional emulsifying agents is selected from sodium phosphate (e.g. monosodium phosphate, sodium tripolyphosphate), dimethicone copolyols (e.g. PEG/PPG-18/18 dimethicone), stearic acid, polyglyceryl-4 isostearate, triethanolamine, ceteareth-25, cetearyl alcohol, sodium lauroyl lactylate, alcohol (e.g. propanol, ethanol, 1-decanol), denatured alcohol, ceteareth-20, PEG-100 stearate, PEG-400 stearate, isopropanolamides of coconut acid (cocamide MIPA), sorbitan stearate, non-foaming emulsifying wax, sorbitan salts (e.g. sorbitan olivate), cetearyl salts (e.g. cetearyl olivate), 2-phenoxyethanol, polyhydroxystearic acid, polyglyceryl-6 polyricinoleate, or combinations thereof.

In some implementations, the one or more optional co-emulsifiers is boric acid, cetyl alcohol, cetearyl alcohol, or combinations thereof.

In some implementations, the one or more optional emulsion stabilizers is selected from dimethicone copolyols (e.g. PEG/PPG-20/23 dimethicone, PEG/PPG-23/6 dimethicone), chloride salts (e.g. sodium chloride, potassium chloride), disteardimonium hectorite, polyethylene, fumed silica, magnesium sulfate, or combinations thereof.

In some implementations, the one or more optional chelating agents is selected from EDTA salts (e.g., disodium EDTA), phosphonates, citric acid, or combinations thereof.

In some implementations, the one or more optional anti-caking agents is selected from dimethicone copolyols (e.g. PEG/PPG-15/15 Dimethicone), corn starch, or combinations thereof.

In some implementations, the one or more optional moisture-absorbing agents is selected from corn starch, talc, or combinations thereof.

In some implementations, the one or more optional silicones is selected from amodimethicone, a dimethicone, or a combination thereof.

In some implementations, the one or more optional silicone conditioner is dimethicone satin.

In some implementations, the one or more optional antimicrobial agents or preservatives is selected from 2-phenoxyethanol, benzyl alcohol, caprylyl glycol, ethylhexyl glycerin, hexanediol, EDTA salts (e.g. disodium EDTA), parabens (e.g. methylparaben, propylparaben), iodopropynyl butacarbamate, or combinations thereof.

In some implementations, the one or more optional stabilizers is selected from EDTA, sodium gluconate, butylated hydroxytoluene, or combinations thereof.

In some implementations, the one or more optional stabilizing salts is selected from sodium sulfate, magnesium chloride, sodium chloride, potassium chloride, or combinations thereof.

In some implementations, the one or more optional corrosion inhibitors is selected from sodium carbonate, calcium chloride, zinc chloride, sodium polyacrylate, silicate, benzimidazole, benzotriazole, calcium succinate, calcium sulfate, ascorbic acid, glucaric acid, gluconic acid, zinc sulfate, cerium chloride, sodium chromate, nitrates, phosphates, magnesium salts, nickel salts, calcium salts, succinic acid, tryptamine, and mercaptobenzothiazole or combinations thereof. In some implementations, the colorant itself may act as a corrosion inhibitor, for example the dye, FD&C Blue #1, can be used as the anti-corrosion or corrosion inhibitor. In addition, pH modifiers such as acids and bases, can be added as anti-corrosion agents or corrosion inhibitors.

In some implementations, the one or more optional perfumes or fragrances is selected from citric acid, anise oil, pinene, bay leaf oil, benzoic acid, acetic acid, camphor oil, florex, geranium oil, grapefruit oil, juniper lactone, lemon oil, myristic oil, orange oil terpenes, *Citrus grandis* seed extract, sandalwood, and vanillin, or combinations thereof.

In some implementations, the one or more alkyl amines is selected from triethanolamine, diethanolamine, triethylamine, methylamine, or combinations thereof.

In some implementations, the one or more oleochemicals is selected from cocamide DEA, oleamide DEA, lauramide DEA, linoleamide DEA, or combinations thereof.

In some implementations, the one or more polymers is selected from polyacrylic acid, polyvinylamides, polyacrylates, polymethacrylates, and cross-linked polymers (e.g., ethers of pentaerythritol, divinylbenzene), or combinations thereof.

In some implementations, the one or more copolymers is selected from acylates/octylacrylamide copolymer, acrylates/steareth-20 methacrylate copolymer, or combinations thereof.

In some implementations, the disclosure provides a two-component composition comprising an indicator composition and an acidified hypochlorite based disinfectant composition, optionally further comprising a surfactant or rheology modifier, or both, the indicator composition comprising a colorant selected from any of a triarylmethane, azo, or acid dye, for example, indigo carmine, Acid Blue 1, FD&C Blue 1, etc., in amounts ranging from about 0.001-15% w/v, preferably from about 0.05-0.50% w/v, or 0.10-0.50% w/v based on the volume of the disinfectant solution to be colored wherein upon combination of the two components, for example via actuation of a device as described herein, the resulting colored disinfectant composition has a fade time of about 30 seconds to 2 minutes, or from about 30 seconds to 10 minutes after its application to a surface.

In some implementations, the disclosure provides a two-component composition comprising an acidified indicator composition and a hypochlorite based disinfectant composition, optionally further comprising a surfactant or rheology modifier, or both, the indicator composition comprising a colorant selected from any of a triarylmethane, azo, or acid dye, for example, indigo carmine, Acid Blue 1, FD&C Blue 1, etc., in amounts ranging from about 0.001-15% w/v, preferably from about 0.05-2.0% w/v, or 0.10-1.0% w/v based on the volume of the disinfectant solution to be colored wherein upon combination of the two components, for example via actuation of a device as described herein, the resulting colored disinfectant composition has a fade time of about 30 seconds to 2 minutes, or from about 30 seconds to 10 minutes after its application to a surface.

In some implementations, the indicator composition comprises a colorant selected from any of a triarylmethane, azo, or acid dye, preferably selected from indigo carmine, Acid Blue 1, or FD&C Blue 1, in amounts ranging from about 0.001-15% w/v, preferably from about 0.05-2.0% w/v, or from about 0.10-1.0%, or from about 0.05-0.50% w/v, or from about 0.10-0.50% w/v, and a surfactant or rheology modifier, or both. In some implementations, the indicator composition comprises a colorant selected from any of a triarylmethane, azo, or acid dye, preferably selected from indigo carmine, Acid Blue 1, or FD&C Blue 1, and the indicator composition further comprises a rheology modifier. In some implementations the rheology modifier is glycerin. The glycerin may be present, for example, at about 1-5% in the indicator composition.

In some implementations, the indicator composition comprises a colorant selected from any of a triarylmethane, azo, or acid dye, preferably selected from indigo carmine, Acid Blue 1, or FD&C Blue 1, most preferably indigo carmine, and the composition further comprises a corrosion inhibitor, preferably sodium carbonate.

In some implementations, the disclosure provides for point of use generation of chlorine dioxide, which is unstable in solution and must prepared fresh for optimal efficacy. Chlorine dioxide may be generated by channeling into a separate compartment of the dispensing device sodium hypochlorite, contained in one chamber of a disinfectant cartridge 413, and sodium chlorite contained in a separate chamber of the same cartridge 413 and mixed before dispensing onto a disinfectant article, such as a wet or dry wipe. Chlorine dioxide can also be generated by mixing as described above sodium dichloroisocyanurate and sodium chlorite before dispensing onto a dry wipe. Chlorine dioxide can also be generated by mixing, as described above, sodium chlorite, hydrochloric acid, and water before dispensing onto a dry wipe.

In some implementations, the disclosure provides a single component indicator composition adapted for use with hypochlorite and troclosene based disinfectant compositions, the composition comprising at least one colorant and one or more of abrasins, or surfactants, or rheology modifiers (thickeners), or bleach activators, or acids, or polyphosphate salts, or rheology builders, or carbonate salts, or bicarbonate salts, or humectants, or antioxidants, or dispersants, or anti-foaming agents, or solubilizing agents, or stabilizers, or corrosion inhibitors, or wetting agents, or enzymes, or hardeners, or softeners, or coating agents, or emulsifiers, or oils, or fragrances, optionally comprising a second component with additional additives as listed above without colorant for better long term storage as additives in either the first or second components, or both, or optionally as a third aqueous component comprising the one or more additives.

In some implementations, the single or multi-component indicator composition comprises a colorant selected from any of a triarylmethane, azo, or acid dye, preferably selected from indigo carmine, Acid Blue 1, or FD&C Blue 1, in amounts ranging from about 0.001-15% w/v, preferably from about 0.05-2.0% w/v, or from about 0.10-1.0%, or from about 0.05-0.50% w/v, or from about 0.10-0.50% w/v, and a rheology modifier. In some implementations the rheology modifier is glycerin. The glycerin may be present, for example, at about 1-5% in the indicator composition.

In some implementations, the single or multi-component indicator composition comprises a colorant selected from a triarylmethane dye, an azo dye, or an acid dye, preferably selected from indigo carmine, Acid Blue 1, or FD&C Blue 1, and the composition further comprises one or more of a rheology modifier selected from glycerin, glyceryl stearate, glyceryl oleate, and mixtures thereof; a polymer or copolymer selected from a polyvinyl carboxy polymer crosslinked with ethers of pentaerythritol (e.g., Carbomer™ 940), an octylacrylamide/acrylates copolymer, and a poly(acrylic acid) copolymer; a solubilizing agent selected from denatured alcohol, triethanolamine, 2-phenoxyethanol, and mixtures thereof; and an antimicrobial agent such as iodopropynyl butacarbamate. In some implementations, the composition may further comprise an opacifying agent selected from mica, titanium dioxide, and mixtures thereof.

In one implementation, a device for use with the multi-component indicator compositions described here comprises two separate compartments, the first compartment comprising a disinfectant composition in the form of an aqueous solution of sodium dichloroisocyanurate ("NaDCC" also referred to as "troclosene") or a disinfectant composition in the form of an aqueous solution of a metal salt of hypochlorous acid, for example sodium or calcium hypochlorite (NaOCl or Ca(OCl)$_2$), optionally comprising a pH modulator sufficient to maintain an alkaline pH of about 10-11; and the second compartment comprising at least one colorant and one or more of any abrasins, or surfactants, or thickeners, or bleach activators, or acids, or polyphosphate salts, or rheology builders, or carbonate salts, or bicarbonate salts, or humectants, or antioxidants, or dispersants, or anti-foaming agents, or solubilizing agents, or wetting agents, or enzymes, or hardeners, or softeners, or coating agents, or emulsifiers, or oils, or fragrances; and further optionally comprising one or more of a surfactant or mixture of surfactants, a buffering agent, a stabilizer or corrosion inhibitor, and a perfume or fragrance, in either the first or second compartments. In some implementations the acidic component may be formed from citric acid, benzoic acid, acetic acid, and mixtures thereof.

In some implementations, the second compartment comprises an indicator composition comprising an aqueous solution of a colorant selected from any of a triarylmethane, azo, or acid dye, preferably selected from indigo carmine, Acid Blue 1, or FD&C Blue 1, most preferably indigo carmine, and a corrosion inhibitor, preferably sodium carbonate.

In some implementations, the disclosure provides a solid or aqueous liquid indicator composition comprising a triarylmethane dye such as brilliant green or acid green 50, a hydroxide base or mixture thereof, such as NaOH and Ca(OH)$_2$, and optionally a hypochlorite or troclosene based disinfectant composition, such as NaDCC, which may further optionally comprise one or more surfactants, either as additives in the indicator composition or the disinfectant composition, or both. In some implementations, the solid form is in the form of a tablet or powder.

In some implementations, the indicator composition comprises a triarylmethane, azo, or acid dye and either (i) a reducing agent such as formic acid, oxalic acid, citric acid, or ascorbic acid, or (ii) a cationic surfactant such as HTAB, SDS, or SXS, and combinations of such surfactants, wherein the composition has a fade time of from 30 seconds to 2 minutes or from 30 seconds to 10 minutes after its combination with a hypochlorite based disinfectant composition.

Indicator Compositions for Quaternary Ammonium/Alcohol Based Disinfectants

In some implementations, the disclosure provides a single or multi-component indicator composition adapted for use with quaternary ammonium compounds and quaternary ammonium compound/alcohol based disinfectant compositions. In some implementations, the multi-component composition comprises at least two separate components, the first component comprising an aqueous solution of quaternary ammonium compounds or alcohol/quaternary ammonium compounds and optionally one or more catalysts; and a second component comprising at least one colorant; and further optionally comprising one or more additives in either the first or second components, or both, or optionally as a third aqueous component comprising the one or more additives. In some implementations, the one or more additives is selected from a surfactant or mixture of surfactants, a base, a buffering agent, and a perfume or fragrance.

Generally, multi-component compositions will sequester the colorant in a separate compartment or reservoir from the catalyst, e.g., separate from any oxidizing agent and/or reducing agent in the composition. In some implementations, it is advantageous to provide the optional surfactant as a separate component from the catalyst, especially metal salts, and also separate from any optional acid in the composition. In multi-component compositions comprising an acid and a base, the acid and base are preferably provided as separate components, i.e., in separate compartments or reservoirs.

In some implementations, the optional base is added to a component of the composition in order to increase the pH of a quaternary ammonium based disinfectant composition at its point of use, e.g., after the components of the multi-component composition have been mixed for use in disinfecting a surface. Preferably, the colorant is sequestered in a separate compartment or reservoir from the base. Some quaternary ammonium based disinfectants perform better at alkaline pH, even though they are less stable at alkaline pH. Accordingly, the multi-component compositions described here provide a method to increase the pH of the disinfectant just prior to use, thereby increasing its effectiveness without losing potency. Suitable bases that may optionally be used to increase the pH of a disinfectant composition include hydroxide bases such as sodium hydroxide, potassium hydroxide, lithium hydroxide, calcium hydroxide, magnesium hydroxide, ammonium hydroxide, and barium hydroxide; carbonate and bicarbonate bases such as sodium bicarbonate, bicarbonate, and calcium carbonate; and other bases such as methyl amine and ammonia; and combinations of any of the foregoing.

In some implementations, the catalyst is selected from an oxidizing agent, a reducing agent, a metal salt, and mixtures thereof. Suitable oxidizing agents include peracetic acid, sodium perchlorate, hydrogen peroxide, and bismuth silver oxide, preferably hydrogen peroxide. Suitable reducing agents include a reducing sugar, water, hydrogen gas, metals, dithionates, thiosulfates, formic acid, oxalic acid, cyanides, hydrazine, iodide salts, sodium dithionite stabilized by sodium sulfite, maltose monohydrate, citric acid, thiourea dioxide, riboflavin, hydroquinone, and ascorbic acid. Preferably, the reducing agent is selected from ascorbic acid, sodium sulfite, dithionite and sodium sulfite, maltose monohydrate, and combinations thereof. Suitable metal salts are those described above, namely those in which the metal salt has an oxidation state of +1, +2, or +3, preferably +2. In some implementations, the metal salt is an iron, copper, zinc, or magnesium salt, preferably an iron salt.

In some implementations, the disclosure provides a device configured to apply a single or multi-component indicator composition as described herein, and a quaternary ammonium salts-based disinfectant composition onto a disinfectant article, such as a wipe, where the article has not been pre-saturated with the disinfectant composition. This configuration is particularly advantageous where the fabric of the disinfectant article affects the disinfectant active ingredient over time and reduces its shelf-life compared to the disinfectant in solution alone. For example, quaternary ammonium salts-based disinfectants lose potency when exposed to cellulosic wipe materials, and for that reason are instead often packaged with polypropylene wipes.

TABLE 1

Representative Examples for Quaternary Ammonium or Alcohol based disinfectants

| | Colorant | Catalyst(s) | Optional Additive(s) | Fade Time (min) |
|---|---|---|---|---|
| 1 | acid dyes, e.g., acid green 25 | Oxidizing agent, e.g., hydrogen peroxide and metal salt, e.g., $Fe^{2+}$ salts | Surfactants, e.g., CTAB Acid, pH 0-6.9 or 0-7 | 3:30-5:00 |
| 2 | thiazine dyes, e.g., methylene blue, toluidine blue O, azure blue | Reducing agent, e.g. vitamin E, nicotinamide | Surfactant, e.g., CTAB and SDS Acid, pH 0-6.9 or 0-7 | 2:00 |
| 3 | acid dyes, e.g., acid green 25, direct blue 86, acid red 1 | Oxidizing agent, e.g., hydrogen peroxide | Surfactants, e.g., CTAB, Tergitols Base, e.g., bicarbonate, hydroxide, pH 7-14 | 20:00-40:00 |
| 4 | indigo carmine, other similar organic salts | Oxidizing agent, e.g., hydrogen peroxide | Base, e.g., hydroxide, pH 7-14 | 20:00-40:00 |
| 5 | anthraquinone dye, e.g., remazol blue | Oxidizing agent, e.g., hydrogen peroxide and metal salt, e.g., $Fe2^{2+}$ salts | Base, e.g., bicarbonate, pH 7-14 | 1:00-15:00 |
| 6 | thiazine dyes, e.g., methylene blue, toluidine blue O, azure blue | Reducing agent, e.g. riboflavin | Base, e.g., hydroxide, pH 7-14 | 20:00-40:00 |
| 7 | cationic dye, e.g., astrazon pink, methyl green | Oxidizing agent, e.g., hydrogen peroxide and metal salt, e.g., $Fe^{2+}$ salts and/or Reducing agent, e.g., sodium dithionite and sodium sulfite | Surfactant, e.g., CTAB and SDS Acid, pH 0-6.9 or 0-7 | 2:30-5:00 |
| 8 | triarylmethane dye, e.g., brilliant green, acid green 50 | Base, e.g., hydroxide, pH 7-14 | Surfactants, e.g., CTAB | 2:00-5:00 (brilliant green) 10:00-40:00 (acid green 50) |
| 9 | leuco dye, e.g., crystal violet lactone | Reducing agent, e.g., sodium dithionite and sodium sulfite | Base, e.g., hydroxide, pH 7-14 | 0:30-8:00 |
| 10 | azo dyes, e.g., orange II, amaranth, napthol green | Oxidizing agent, e.g., hydrogen peroxide | Base, e.g., bicarbonate, hydroxide, pH 7-14 | 20:00-40:00 |
| 11 | cationic dye, e.g., astrazon red, astrazon pink | Oxidizing agent, e.g., hydrogen peroxide | Surfactant, e.g., CTAB and SDS Base, e.g., bicarbonate, pH 7-14 | 1:30-3:00 |
| 12 | triarylmethane dye, e.g., brilliant green, crystal violet | Reducing agent, e.g., sodium dithionite and sodium sulfite | | 2:00 |

TABLE 1-continued

Representative Examples for Quaternary Ammonium or Alcohol based disinfectants

| | Colorant | Catalyst(s) | Optional Additive(s) | Fade Time (min) |
|---|---|---|---|---|
| 13 | triarylmethane and thiazine dyes, e.g., FD&C Blue 1, methylene blue | Oxidizing agent, e.g., metal salt, e.g., $Cu^{2+}$ salts | Base, e.g., hydroxide, pH 7-14 | 2:00-15:00 |
| 14 | fluorone dye, e.g., rhodamine b | Oxidizing agent, e.g., hydrogen peroxide and metal salt, e.g., $Fe^{2+}$ salts | Acid, pH 0-6.9 or 0-7 | 8:00-9:00 |
| 15 | triarylmethane, azo, or acid dyes e.g., acid blue 1, brilliant green, acid blue 83 | Oxidizing agent, e.g., hydrogen peroxide | Base, e.g., hydroxide or bicarbonate, pH 7-14 Surfactant, e.g., CTAB and SDS | 0:30-5:00 |
| 16 | thiazine dyes, e.g., methylene blue, toluidine blue O, azure blue | Oxidizing agent, e.g., metal salt, e.g., $Fe^{2+}$ salts | Base, e.g., hydroxide, pH 7-14 | 20:00-40:00 |
| 17 | leuco dye, e.g., crystal violet lactone | alcohol | | 00:45 |
| 18 | inorganic compounds such as potassium permanganate | alcohol | Acid, pH 0-6.9 or 0-7 Surfactants, e.g., CTAB | 2:00-3:00 |

In some implementations, the catalyst is an oxidizing agent, preferably hydrogen peroxide, the colorant is a water-soluble oxidizable dye, preferably selected from an azo dye, a triarylmethane dye, and an acid dye, and one or more components of the composition further comprises a base, such as a hydroxide base, sufficient to maintain an alkaline pH of the point of use composition.

In some implementations, the catalyst is a combination of an oxidizing agent, preferably hydrogen peroxide, a reducing agent, preferably sodium dithionite and sodium sulfite, and a metal salt, preferably an iron salt such as iron sulfate, and the colorant is a cationic dye, such as Astrazon Pink or Astrazon Red.

In some implementations, the composition comprises hydrogen peroxide as the catalyst, a cationic dye such as Astrazon Pink or Astrazon Red, a surfactant, and an alkaline salt such as sodium triphosphate, also referred to as sodium tripolyphosphate (STPP).

In some implementations, the catalyst may comprise a strong base, a weak base, or a combination of strong and/or weak bases.

In some implementations, the indicator composition comprises a triarylmethane, azo, or acid dye, a catalyst, preferably hydrogen peroxide, and a base, preferably a hydroxide or bicarbonate base sufficient to maintain an alkaline pH, wherein the composition has a fade time of from 1-2 minutes.

In some implementations, the indicator composition comprises a cationic dye, a catalyst, such as hydrogen peroxide or a metal salt, and combinations of such catalysts, and one or more of a reducing agent, such as sodium dithionite and sodium sulfite, citric acid, or ascorbic acid, and combinations of such reducing agents, and a cationic surfactant such as HTAB, SDS, or SXS, and combinations of such surfactants, wherein the composition has a fade time of from 2-4 minutes.

In some implementations, the indicator composition comprises a cationic dye, a catalyst, preferably hydrogen peroxide, and a base, preferably a hydroxide or bicarbonate base sufficient to maintain an alkaline pH, a surfactant, preferably a nonionic surfactant such as a polyglycol ether, a cationic surfactant, such as HTAB, and combinations of such surfactants, wherein the composition has a fade time of from 1-3 minutes.

In some implementations, the catalyst comprises or consists of a base, for example, where the colorant is a triarylmethane dye, such as brilliant green or acid green 50, a base is sufficient to fade the dye to clear, with stronger bases reducing the fade time. For other colorants, where an oxidizing or reducing agent provides the main catalyst, additional base may be added to reduce the fade time.

In some implementations, the catalyst is provided by the disinfectant composition, or a component thereof, for example alcohol in an optionally acid environment will fade the color of inorganic compounds such as potassium permanganate; and alcohol will fade the color of leuco dyes such as crystal violet and lactone.

Generally, the desired fade time is achieved by modulating the concentrations and volumes of the catalyst, however the concentration and volume of the colorant may also be used to affect fade time.

Indicator Compositions for Hydrogen Peroxide Based Disinfectants

In some implementations, the disclosure provides a single or multi-component indicator composition adapted for use with a hydrogen peroxide based disinfectant solution, for example aqueous solutions of from about 0.01 to 75% w/v hydrogen peroxide, preferably from about 0.1 to 10% w/v, from 0.1 to 5% w/v, or from 0.1 to 2% w/v hydrogen peroxide. In some implementations, the multi-component composition comprises at least two separate components, the first component comprising a colorant and the second component comprising a catalyst effective to generate hydroxyl radicals in the presence of hydrogen peroxide. Such radicals are short-lived but powerful oxidizers. Accordingly, the disclosure also provides methods of disinfecting and/or decontaminating a surface that both increases the strength of a hydrogen peroxide based disinfectant and provides a visible indicator of the completeness of the disinfection and/or decontamination. In some implementations, the multi-component composition comprises at least two separate components, the first component comprising a colorant, and the second component comprising a catalyst and/or additional hydrogen peroxide. The single or multi-component composition may further optionally comprise one or more optional additives in either the first or second components, or both, or optionally as a third aqueous component comprising the one or more additives. In some implementations, the one or more additives is selected from a surfactant or mixture of surfactants, a base, a buffering agent, and a perfume or fragrance.

In some implementations, the colorant is selected from a triarylmethane dye, such as lissamine green, a synthetic basic dye, an anthraquinone dye, a nitroso dye, and a double azo dye. In some implementations, the colorant is a dye having at least two aromatic rings connected by at least one covalent bond, preferably an ethyl moiety, for example indigo carmine, quinoline yellow, crysophenine, astrazon pink, astrazon red, or Rhodamine B. In some implementations the colorant is selected from astrazon pink, indigo carmine, orange II, FD&C Blue, lissamine green, brilliant green, methylene blue, remazol blue, bromophenol blue, acid blue, naphtol green, crystal violet lactone, and quinoline yellow.

In some implementations, the one or more catalysts is selected from a strong base, a weak base, a combination of strong and/or weak bases, an oxidizing agent, a reducing agent, and a metal salt. In some implementations, the strong base is selected from potassium hydroxide (KOH), sodium hydroxide (NaOH), lithium hydroxide (LiOH), rubidium hydroxide (RbOH), cesium hydroxide (CsOH), calcium hydroxide ($Ca(OH)_2$), strontium hydroxide ($Sr(OH)_2$), magnesium hydroxide ($Mg(OH)_2$), and barium hydroxide ($Ba(OH)_2$), preferably KOH, NaOH, LiOH, or $Ca(OH)_2$. In some implementations, the weak base is selected from a base having a $pK_b$ of less than 7, preferably any bicarbonate salt, any carbonate salt, methyl amine, hydroxides of quaternary ammonium cations or other organic cations, pyridine, aniline, imidazole, histidine, benzimidazole, any phosphazene base, and any nucleobase.

In some implementations, the catalyst comprises a metal salt in which the metal salt has an oxidation state of +1, +2, or +3, preferably +2. In some implementations, the metal salt is an iron, copper, zinc, or magnesium salt, preferably an iron salt. In some implementations, the metal salt is a sulfate, nitrate, bromide, chloride, gluconate, sulfide, fumarate, oxide, iodide, fluoride, acetate, oxalate, stearate, diethyldithiocarbamate, ethoxide, citrate, trifluoromethanesulphonate, or cyanide salt. In some implementations, the metal salt is a sulfate, nitrate, bromide, chloride, or fluoride salt. In some implementations, the metal salt is anhydrous or hydrated, preferably a mono-, di-, tri-, penta-, hexa-, hepta-, nona-hydrate salt. In implementations where a weak metal salt catalyst is used, such as copper, zinc, or magnesium, the composition may further comprise an optional reducing agent which serves to replenish the metal catalyst by returning it to a lower oxidation state. In some implementations, the metal salt is $FeSO_4$. In some implementations, the amount of the metal salt in the composition is adapted to provide a final concentration of the metal catalyst in the range of from about 0.001 to 20 M, preferably from about 0.010 to 0.100 M, or from 0.015 to 0.075 M.

In some implementations, the catalyst comprises a reducing agent. In some implementations, the reducing agent is selected from one or more of a reducing sugar, a dithionate, a thiosulfate, formic acid, oxalic acid, cyanides, hydrazine, iodide salts, sodium dithionite stabilized by sodium sulfite, maltose monohydrate, citric acid, thiourea dioxide, riboflavin, hydroquinone, and ascorbic acid.

In some implementations, the catalyst comprises an oxidizing agent. In some implementations, the oxidizing agent is selected from one or more of a peroxide, oxone, bleach, riboflavin, nitrate salts, persulfate salts, dichromate salts, and nitrite salts. In some implementations the oxidizing agent is selected from oxone and additional hydrogen peroxide, that is in addition to that of the disinfectant composition itself with which the indicator composition is mixed at point of use.

In some implementations, the optional surfactant is selected from one or more of a one or more of a nonionic surfactant, such as a polyglycol ether, tetramethyl decynediol, and cocomonoisopropanolamide; an anionic surfactant such as alkyldiphenyloxide disulfonate, sodium lauryl sulfate (SLES), and Stepanol™ WA-100; and a cationic surfactant such as hexadecyltrimethylammonium bromide (HTAB), which may also be referred to as cetylmethylammonium bromide (CTAB). In some implementations, the surfactant is sodium xylene sulfonate (SXS) or sodium toluene sulfonate (STS). In some implementations, the surfactant is sodium dodecyl sulfate (SDS), sodium xylene sulfonate (SXS), and mixtures thereof.

In some implementations, the disclosure provides a single or multi-component indicator composition adapted for use with a hydrogen peroxide based disinfectant solution comprising a colorant, a metal catalyst, and a reducing agent, and optionally one or more surfactants and an additional oxidizing agent in the form of additional hydrogen peroxide. In some implementations, the single or multi-component indicator composition comprises a colorant such as indigo carmine, a metal catalyst such as cupric sulfate pentahydrate/ferrous sulfate anhydrous or heptahydrate, a reducing agent such as maltose monohydrate or citric acid, preferably maltose monohydrate, an additional oxidizing agent in the form of additional hydrogen peroxide, and optionally one or more surfactants selected from SDS, SXS, and mixtures thereof.

In some implementations, the disclosure provides a single or multi-component indicator composition adapted for use with a hydrogen peroxide based disinfectant solution comprising a colorant, a metal catalyst, such as an Fe' salt, and a pH modulator adapted to maintain the metal catalyst in an acidic aqueous solution of pH 5, preferably pH less than 3, and optionally one or more of a reducing agent, and an additional oxidizing agent. In some implementations, the colorant is selected from astrazon pink, orange II, triarylmethane dye, and quinoline yellow. In some implementations, the single or multi-component indicator composition adapted to color an aqueous solution of from about 0.01 to 75% w/v hydrogen peroxide, preferably from about 0.1-11% w/v, from 0.1-6% w/v, or from 0.1-3% w/v hydrogen peroxide, such that the color fades to clear within about 30 seconds to 30 minutes, or 1-30 minutes, upon application of the colored hydrogen peroxide solution to a surface. In some implementations, the color fades to clear within about 30 seconds to 1 minute, or within about 2-15 minutes, or about 10-30 minutes.

In some implementations, the disclosure provides a single or multi-component indicator composition adapted for use with a hydrogen peroxide based disinfectant solution comprising a colorant, a metal catalyst, such as an Fe' salt, and a pH modulator, such as an acid or combination of acids, adapted to maintain the metal catalyst in an acidic aqueous solution of pH 5, preferably pH less than 3, and optionally comprising an additional oxidizing agent. In some implementations, the colorant is selected from brilliant green, methylene blue, remazol blue, bromophenol blue, acid blue, naphthol green, and crystal violet lactone.

In some implementations, the disclosure provides an article of manufacture comprising the single or multi-component indicator compositions described herein, either in a single compartment, or contained within two or more separate compartments or chambers, which are adapted to be mixed upon together to form a single component indicator composition at the point of use, as described above. For example, the article may further comprise a tubing and nozzle system that allows contents from different compartments to communicate into a single solution before communicating with the disinfectant.

In some implementations, a multi-component composition is provided wherein each of at least two components is provided in physically separate reservoirs or chambers, one containing a hydrogen peroxide solution and a separate chamber containing a catalyst, such as a metal salt, for example, $FeSO_4$, in an aqueous solution. In some implementations, the two components are contained in a cartridge 413 adapted to fit within a device as described here and may be dispensed simultaneously onto a disinfectant article, such as a wipe. Alternatively, the hydrogen peroxide solution and the catalyst solution can be fed from their respective chambers into a mixing chamber within the cartridge 413 or device before dispensing onto the disinfectant article. In a further implementation, the hydrogen peroxide solution and the metal catalyst solution may be dispensed sequentially onto the article. As described above and illustrated in Table 2 below, other metal salts are suitable catalysts, including for example salts of $Zn^{2+}$, $Co^{2+}$, $Cu^{2+}$, $Ni^{2+}$, $Mn^{2+}$, and $Cr^{3+}$.

TABLE 2

Representative Examples for Hydrogen Peroxide Based Disinfectants.

| | Colorant | Catalyst(s) | Optional Additive(s) | Fade Time (min) |
|---|---|---|---|---|
| 1 | azo dyes, e.g., orange II | Oxidizing agent, e.g., metal salt, e.g., $Fe^{2+}$ salts | Acidic agent or buffer at pH 3 or pH 1.5 | 2:00-15:00 |
| 2 | indigo carmine, other similar organic salts | Oxidizing agent, e.g., metal salt, e.g., $Fe^{2+}$ or $Zn^{2+}$ salts and Reducing agent, e.g., magnesium gluconate | Acidic agent or buffer at pH 3 or pH 1.5 | 20:00-40:00 |
| 3 | triarylmethane dye, e.g., lissamine green | Oxidizing agent, e.g., $Fe^{2+}$ salts | Acidic agent or buffer at pH 3 or pH 1.5 | 2:00-15:00 |
| 4 | thiazine dyes, e.g., methylene blue, toluidine blue O, azure blue | Oxidizing agent, e.g., hydrogen peroxide* | Acidic agent or buffer at pH 3 or pH 1.5 | 2:00-10:00 |
| 5 | brilliant green methylene blue remazol blue bromophenol blue acid blue 113 naphthol green crystal violet lactone | Oxidizing agent, e.g., $Fe^{2+}$ salts and hydrogen peroxide* | Acidic agent or buffer at pH 3 or pH 1.5 | 1:00-30:00 |
| 6 | triarylmethane dye, e.g., FD&C Blue | Oxidizing agent, e.g., $Fe^{2+}$ salts and oxone | Acidic agent or buffer at pH 3 or pH 1.5 | 11:00 |
| 7 | indigo carmine, other similar organic salts | Oxidizing agent, e.g., hydrogen peroxide* | Surfactant, e.g., SXS, SDS Base, e.g., hydroxide, bicarbonate, and mixtures thereof | 1:00-1:30 |
| 8 | indigo carmine, other similar organic salts | Oxidizing agent, e.g., metal salt, e.g., $Cu^{2+}$ salts, hydrogen peroxide* and Reducing agent, e.g., sodium dithionite and sodium sulfite, maltose, an acid or combination of acids, hydroquinone | Surfactant, e.g., Tergitols, SXS, SDS Acidic agent or buffer at pH 3 or pH 1.5 | 0:45-1:15 0:45-2:30 with pH 3 buffer 0:45 with pH 1.5 buffer |
| 9 | acid green 50, amaranth | Oxidizing agent, e.g., $Fe^{2+}$ salts | Acidic agent or buffer at pH 3 or pH 1.5 Surfactant, e.g., CTAB | 20:00-40:00 |
| 10 | quinoline yellow | Oxidizing agent, e.g., $Fe^{2+}$ salts | Acidic agent or buffer at pH 3 or pH 1.5 | 10:00-30:00 |
| 11 | triarylmethane dye, e.g., brilliant green | Oxidizing agent, e.g., hydrogen peroxide* or Reducing agent, e.g., riboflavin | Base, e.g., hydroxide | 20:00-40:00 |
| 12 | cationic dye, e.g., astrazon pink | Oxidizing agent, e.g., metal salt, e.g., $Fe^{2+}$ salts | Acidic agent or buffer at pH 3 or pH 1.5 | 1:00 |

*hydrogen peroxide may be additional, as a component of a multi-component composition, or it may be provided by the disinfectant composition, or both.

In some implementations, the composition comprises a colorant that is an organic salt, such as indigo carmine or a similar organic salt, a catalyst, preferably hydrogen peroxide or a metal salt, or a combination of such catalysts, and further comprising a nonionic surfactant, preferably a polyglycol ether, a cationic surfactant, preferably SDS, SXS, or a combination of such surfactants, a reducing agent, such as sodium dithionite and sodium sulfite, maltose monohydrate, citric acid, hydroquinone, or ascorbic acid, and combinations of such reducing agents, wherein the composition has a fade time of from 30 seconds to 2 minutes.

In some implementations, the composition comprises a colorant that is an organic salt, such as indigo carmine or a similar organic salt, a combination of catalysts including hydrogen peroxide and a metal salt, preferably a copper salt such as copper sulfate (Cu(II)SO$_4$), a cationic surfactant, preferably SDS or a combination of SDS and SXS, and a reducing agent, preferably maltose monohydrate.

In some implementations, the composition comprises a colorant that is an organic salt, such as indigo carmine or a similar organic salt, a combination of catalysts including hydrogen peroxide and one or more metal salts, preferably a copper salt such as copper sulfate (Cu(II)SO$_4$) and/or an iron salt such as iron sulfate (Fe(II)SO$_4$), a surfactant selected from a cationic and nonionic surfactant, such as SDS, SXS, tergitol, and mixtures thereof, and a reducing agent selected from maltose monohydrate, citric acid, and mixtures thereof.

Indicator Compositions for Peracetic Acid Based Disinfectants

In some implementations, the disclosure provides a single or multi-component indicator composition adapted for use with peracetic acid based disinfectant compositions. In some implementations, the multi-component composition comprises at least two separate components, the first component comprising an aqueous solution of peracetic acid; and a second component comprising at least one colorant and one or more catalysts; and further optionally comprising one or more optional additives in either the first or second components, or both, or optionally as a third aqueous component comprising the one or more additives. In some implementations, the one or more additives is selected from a surfactant or mixture of surfactants, a base, a buffering agent, and a perfume or fragrance.

In accordance with this embodiment, it is noted that certain surfactants may act in a dual role as catalysts via the generation of hydroxyl radicals, for example, cetylmethylammonium bromide (CTAB).

As with chlorine dioxide, peracetic acid is known to degrade rapidly in solution, and peracids and peroxides are known to decompose even faster in solution when incorporated into a disinfectant article, such as a wet wipe. Accordingly, in some implementations, the disclosure provides for point of use generation of peracetic acid by combining acetic acid and hydrogen peroxide. For example, in a disinfectant dispensing cartridge 413, one reservoir chamber can contain acetic acid and the other reservoir chamber can contain hydrogen peroxide that when mixed such as by channeling into a mixing compartment, generate peracetic acid ready for dispensing onto a disinfectant article, such as wet or dry wipe. Peracetic acid also can be released from certain solid compounds, for example, peracetyl borate (PAB). Dry wipes embedded with PAB or some other peracetic acid-releasing solid may be dispensed through the device described herein. For example, the device can add water and/or solvent at the indicator to activate the solid peracetic acid.

TABLE 3

Representative Examples for Peracetic Acid Based Disinfectants

| Colorant | Catalyst(s) | Optional Additive(s) | Fade Time (min) |
| --- | --- | --- | --- |
| 1 indigo carmine, other similar organic salts | Oxidizing agent, e.g., metal salt, e.g., Cu$^{2+}$ salts, Fe$^{2+}$ salts | Reducing agent, e.g., citric acid, ascorbic acid | 0:30-1:00 |
| 2 quinophthalone pigments, e.g., quinolone yellow | | | 1:00 |
| 3 triarylmethane dyes, acid dyes, e.g., acid green 50, FD&C blue, acid green 25 | Oxidizing agent, e.g., metal salt, e.g., Cu$^{2+}$ salts, Fe$^{2+}$ salts | Surfactant, e.g., CTAB | 0:30-10:00 |
| 4 triphenylmethane dyes, e.g., patent blue V | | Surfactant, e.g., CTAB | 5:00 |
| 5 organoiodine compounds, e.g., erythrosine supra (red no. 3) | | | 2:00 |

In some implementations, the indicator composition comprises an acid dye, such as acid green and a surfactant.

In some implementations, the indicator composition comprises an acid dye, such as acid green, e.g., Acid Green 25 or Acid Green 50, or Acid Blue 1, and a surfactant, preferably CTAB.

In some implementations, the indicator composition comprises an organic salt such as indigo carmine, a catalyst, preferably a metal salt, and a reducing agent, preferably citric acid, ascorbic acid, and combinations thereof, wherein the composition has a fade time of from 3-10 minutes.

Hand Sanitizer Compositions

In some implementations, a single or multi-component indicator composition as described here can be adapted for use with a hand soap or sanitizer, including liquid soaps, alcohol-based hand rubs, hand sanitizer foams, etc., to impart transient color to the soap or sanitizer and allow its visualization following application to skin or glove surfaces.

The indicator composition may be mixed directly with a conventional hand soap or sanitizer solution, for example by actuation of the device housing the soap/sanitizer and indicator composition at point-of-use. In some implementations, the disclosure provides an article of manufacture in the form of a dispenser comprising a pump element, the dispenser adapted to hold the indicator composition in one or more containers or reservoirs. The dispenser article may be adapted to as a replacement or attachment that replaces or attaches to a containing holding the soap/sanitizer composition. In accordance with this implementation, the dispenser article dispenses an amount of the indicator composition to the soap/sanitizer upon actuation, for example via channels, reservoirs, etc. In some embodiments, the dispenser article is adjustable so that it can be adapted to fit different sized containers of hand soap/sanitizer. In some embodiments, the dispenser article may further include a switch mechanism adapted to place the dispenser article into an "active" or "inactive" configuration, which configurations either allow or block the addition of the indicator composition to the soap/sanitizer upon actuation of the device, thereby enabling the user to select whether the dispensed hand soap or sanitizer is colored or remains uncolored.

In some implementations, the disclosure also provides a composition adapted to impart a permanent color rather than a transient color. Such compositions may be used, for example, in a training environment to provide a visual record of a user's efficiency in applying the disinfectant composition, for example to a glove or other disposable item. In some implementations, these compositions may also comprise one or more of a surfactant, a thickener, a rheology builder, a humectant, a dispersant, an abrasin, a fragrance, aromatic oil, or perfume, a hardener, a softener, a wax, an emulsifier, and a coating agent. In some implementations, the colorant is a color-producing organic salt or acid.

Exemplary indicator compositions for use with alcohol-based hand sanitizers include 0.01-5% colorant, and an optional additive such as a surfactant, thickening agent, e.g., glycerin, and a pH modulator, such as an alkaline builder, e.g., sodium hydroxide or potassium hydroxide, and mixtures thereof. In some implementations, the composition further comprises a catalyst. In some implementations, the catalyst is selected from hexadecyltrimethylammonium bromide (HTAB or CTAB), copper (II) sulfate pentahydrate, and iron (III) nitrate nonahydrate. In some implementations, the colorant may be selected from a triarylmethane dye such as FD&C Blue #1, a phenol dye such as phenolphthalein, thermochromic 32, and Celsius blue dye, and combinations thereof. In some implementations, the colorant is selected from FD&C Blue #1, fast green FCF, erythrosine, allura red AC, tartrazine, sunset yellow FCF, indigo carmine, ultramarine, cobalt blue, phthalocyanine, and Coomassie Brilliant Blue, Acid Green 25, Bromothymol Blue, Acid Green 50, Acid Blue 80, Remazol Brilliant Blue R, crystal violet lactone, patent blue V, thymolphthalein, rhodamine B, acid orange 7, astrazon red, astrazon pink, or a mixture of one or more thereof. In some implementations the surfactant is selected from sodium dodecyl sulfate, sodium dodecylbenzenesulfonate, hexadecyltrimethylammonium bromide (HTAB or CTAB), sodium 3,4-dichlorobenzoate, sodium laureth sulfate, sodium xylene sulfonate, and sodium toluene sulfonate.

In some implementations, the indicator composition is a non-fading composition. In one implementation, the non-fading composition comprises or consists of a colorant selected from Acid Orange II, Astrazon Pink, Astrazon Red, Acid Blue 1, and FD&C Blue 1, and a surfactant, preferably SDS.

As discussed above, in some implementations the dispenser article is adapted as a replacement or attachment that replaces or attaches to a containing holding the soap/sanitizer composition. In some implementations, the dispenser article adapted for attachment comprises a funnel with a top opening and a bottom opening, the funnel having a reservoir for holding an indicator composition as described herein; and an adhesive ring deposed at the top end of the funnel attachment. The funnel is affixable to the liquid dispenser through the adhesive ring such that when the liquid dispenser dispenses an aliquot of the liquid, it is captured through the top opening of the funnel and travels through the indicator composition so as to emerge from the bottom opening of the funnel having been imbued with a colorant.

In some implementations, the dispenser article is a motion-activated hand sanitizer dispenser. In some implementations, the adhesive ring is circular. In certain embodiments, the adhesive ring is not circular. In some implementations, the funnel attachment is affixed to the liquid dispenser through a clamp.

In some implementations, dispenser article is a pump dispenser for dispensing a liquid. The pump dispenser includes: a piston chamber; a piston housed in the piston chamber, the piston is characterized by a habitual position and a depressed position when pressed; a first reservoir for holding the liquid to be dispensed, the first reservoir comprising: an inlet for fluid communication between the piston chamber and the first reservoir, and an outlet for fluid communication out of the piston chamber; a second reservoir for holding an additive composition, the second reservoir comprising: an inlet for fluid communication between the piston chamber and the second reservoir, and an outlet for fluid communication out of the second reservoir; and a spring attached to the piston. The spring is depressed when a pressure is applied to the piston and returns the piston to the habitual position upon relief of the pressure. The pump dispenser is configured such that a movement of the piston from the habitual position to the depressed position causes the liquid to be dispensed to move from the first reservoir to the piston chamber, from the piston chamber to the second reservoir, and eventually exiting the second reservoir.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A device for applying a composition to a wipe dispensed through the device, the device comprising:
   a housing at least partially surrounding an interior volume and comprising:
      (i) an exterior wall defining a dispensing aperture extending through the exterior wall;
      (ii) a lower end region comprising an opening through which at least one wipe of a plurality of wipes is drawn into the interior volume of the housing from a canister holding the plurality of wipes; and
      (iii) one or more connecting features on the lower end region;
   a dispensing mechanism positioned within the interior volume of the housing, the dispensing mechanism comprising a plurality of rollers configured to capture and direct the at least one wipe through the interior volume of the housing towards the dispensing aperture;
   an application mechanism positioned within the interior volume of the housing relative to the dispensing aperture;
   a processor in operative communication with a sensor and an input, the sensor configured to communicate to the processor information related to the at least one wipe directed towards the dispensing aperture; and
   a removable cartridge configured to be coupled to the housing, the cartridge comprising:
      a cartridge housing defining a reservoir; and
      a penetrable barrier extending through a portion of the housing;
   wherein the reservoir comprises a first chamber sized to contain a first composition, a second chamber sized to contain a second composition, and a third chamber sized to contain a third composition.

2. The device of claim 1, wherein the processor is configured to monitor, analyze, and record in a memory of the device the information.

3. The device of claim 1, wherein the processor is configured to control automatically at least one function of the device based on the information.

4. The device of claim 1, wherein the information communicated from the sensor to the processor is synchronized with a time log.

5. The device of claim 4, wherein the information synchronized with the time log indicates productivity of a user and/or activity of the device.

6. The device of claim 1, wherein the information communicated from the sensor to the processor is analyzed by software program running on the processor.

7. The device of claim 1, wherein the information communicated from the sensor indicates a number of the plurality of wipes dispensed through the dispensing aperture.

8. The device of claim 7, wherein the number of the plurality of wipes dispensed is based on an amount time spent actuating the input of the device.

9. The device of claim 7, wherein the number of the plurality of wipes dispensed is based on a number of revolutions made by the plurality of rollers.

10. The device of claim 7, wherein the number of the plurality of wipes dispensed is based on perforations between each of the plurality of wipes dispensed detected by the sensor.

11. The device of claim 7, wherein the number of the plurality of wipes dispensed is synchronized with a time log.

12. The device of claim 1, wherein the information communicated from the sensor to the processor indicates timing between when a first wipe of the plurality of wipes is dispensed and a second wipe of the plurality of wipes is dispensed.

13. The device of claim 1, wherein the information communicated from the sensor to the processor indicates a frequency of wipes dispensed over time.

14. The device of claim 1, wherein the information communicated from the sensor to the processor indicates when multiple wipes are dispensed simultaneously.

15. The device of claim 1, wherein the sensor is an optical sensor or a mechanical sensor.

16. The device of claim 1, wherein the information communicated is a presence of the at least one wipe of the plurality of wipes within the dispensing aperture.

17. The device of claim 16, wherein at least a portion of the at least one wipe interfaces with the sensor.

18. The device of claim 1, wherein the device further comprises a movable, mechanical cover located relative to the dispensing aperture that is configured to interface with the sensor.

19. The device of claim 18, wherein the information communicated by the sensor is displacement of the cover relative to the dispensing aperture.

20. The device of claim 18, wherein the processor is programmed to inactivate one or both of the application mechanism and the dispensing mechanism based on the information communicated from the sensor.

21. The device of claim 18, wherein the information communicated from the sensor indicates the cover is displaced and has not moved for a period of time.

22. The device of claim 21, wherein the processor is programmed to cause the plurality of rollers to automatically withdraw the at least one wipe of the plurality of wipes away from the dispensing aperture after the period of time.

23. The device of claim 21, wherein the period of time is between 10 seconds and 30 seconds, between 30 seconds and 1 minute, between 1 minute and 2 minutes, between 1 minute and 5 minutes, between 1 minute to about 20 minutes, or between 1 minute to about 60 minutes.

24. The device of claim 21, wherein the device further comprises a user interface and the period of time is programmable by a user on the user interface.

25. The device of claim 1, wherein the sensor comprises a first sensor configured to interface with the at least one wipe of the plurality of wipes within the dispensing aperture and the device further comprises a second sensor configured to interface with a movable, mechanical cover located relative to the dispensing aperture.

26. The device of claim 1, wherein the exterior wall of the housing forms an upper surface of the device or a side surface of the device.

27. The device of claim 1, wherein the lower end region of the housing is sized to couple to the canister holding the plurality of wipes.

28. The device of claim 27, wherein the one or more connecting features on the lower end region are configured to removably couple the lower end region to the canister.

29. The device of claim 27, wherein when the device is coupled to the canister, an interior of the canister is in fluid communication with the interior volume of the housing through the opening.

30. The device of claim 27, wherein the device forms a removable lid for the canister.

31. The device of claim 1, further comprising an adapter comprising a first lip on an upper region of the adapter and a second lip on a lower region of the adapter, wherein the first lip is sized to reversibly couple to the lower end region of the housing and the second lip is sized to reversibly couple to the canister.

32. The device of claim 31, wherein the one or more connecting features on the lower end region of the housing are configured to removably couple the lower end region of the housing to an adapter.

33. The device of claim 31, wherein the adapter comprises a sensor configured to interface with one or both of the device and the canister.

34. The device of claim 1, wherein the sensor of the device is configured to interface with a corresponding element on the canister holding the plurality of wipes.

35. The device of claim 34, wherein the sensor of the device is a mechanical sensor or an optical sensor.

36. The device of claim 34, wherein the corresponding feature on the canister is a tactile series of ridges and bumps forming a code configured to be detected by the sensor.

37. The device of claim 36, wherein the code provides information about the plurality of wipes contained within the canister.

38. The device of claim 36, wherein the code delineates one or both of a chemistry of the plurality of wipes and wipe dimension.

39. The device of claim 1, wherein the compositions in the first, second or third chambers are the same compositions, different compositions, or components of a single composition.

40. The device of claim 1, wherein the cartridge comprises a sensor configured to detect liquid volume within the reservoir of the cartridge.

41. The device of claim 40, wherein the sensor of the cartridge is an optical sensor or a mechanical sensor.

42. The device of claim 1, wherein the reservoir is refillable.

43. The device of claim 1, wherein the compositions in the first, second and/or third chambers are the same compositions or different compositions.

44. The device of claim 43, wherein the application mechanism is configured to apply the first, second, and third composition to the at least one of the plurality of wipes.

45. The device of claim 43, wherein the application mechanism is configured to apply the first, second, and third compositions simultaneously.

46. The device of claim 43, wherein the application mechanism is configured to apply the first, second, and third compositions.

47. The device of claim 43, wherein the application mechanism comprises a first applicator for the first composition, a second applicator for the second composition; and a third applicator for the third composition.

48. The device of claim 47, wherein the first, second, and third applicators are arranged to dispense in parallel, in series, or in combination.

49. The device of claim 43, wherein the first composition comprises a colorant selected from any of a triarylmethane, azo, indigoid, or acid dye; optionally further comprising an acidic agent or acidifying agent, a corrosion inhibitor, or both an acidic agent or acidifying agent and a corrosion inhibitor.

50. The device of claim 49, wherein the second composition is a hypochlorite based disinfectant composition, optionally further comprising a surfactant or rheology modifier, or both.

51. The device of claim 43, wherein the application mechanism comprises at least one applicator; and a transfer element including a pump.

52. The device of claim 51, wherein the transfer element transfers the amount of the first and second compositions from the reservoir towards the at least one applicator.

53. The device of claim 52, wherein the transfer element creates a pressure differential relative to an interior of the reservoir to transfer the amount.

54. The device of claim 51, wherein the input is an actuator configured to simultaneously activate the pump of the dispensing mechanism and the application mechanism.

55. The device of claim 54, wherein the dispensing mechanism further comprises a motor.

56. The device of claim 55, wherein the actuator activates the motor.

57. The device of claim 56, further comprising a removable cover positioned over the dispensing aperture.

58. The device of claim 57, wherein the actuator opens the cover exposing the dispensing aperture.

59. The device of claim 57, further comprising one or more grippers configured to engage the wipes during dispensing.

60. The device of claim 59, wherein the actuator activates the one or more grippers.

61. The device of claim 59, wherein the actuator activates one or more of the transfer element, the at least one applicator, the motor, the cover, and the grippers simultaneously.

62. The device of claim 51, wherein the pump of the transfer element is powered by an electric motor upon actuation of the input to create a pressure differential relative to the interior volume of the reservoir.

63. The device of claim 62, wherein the pump is a positive displacement pump, reciprocating pump, rotary pump, piston pump, diaphragm pump, peristaltic pump, dynamic pump, centrifugal pump, or hydraulic pump.

64. The device of claim 51, wherein the at least one applicator is configured to apply the amount of first and second composition to the wipe by directly contacting the wipe.

65. The device of claim 43, wherein the application mechanism provides for one-sided or two-sided application of the amount of the first, second, and third compositions to the wipe.

66. The device of claim 1, wherein the reservoir further comprises one or more additional chambers.

67. The device of claim 49, wherein the acidic agent or acidifying agent is selected from citric acid, benzoic acid, acetic acid, hydrochloric acid, sulfuric acid, nitric acid, hydrofluoric acid, hydrobromic acid, perchloric acid, chloric acid, hydroiodic acid, sulfurous acid, methanoic acid, phosphoric acid, nitrous acid, benzenesulfonic acid, metaperiodic acid, ascorbic acid, trimethoxybenzoic acid, peracetic acid, oxalic acid, formic acid, glucaric acid, gluconic acid, tartaric acid, lactic acid, boric acid, carbonic acid, acrylic acid, phenylsuccinic acid, succinic acid, propanoic acid, and acidic buffers within the range of pH 0-7 comprised of said acids and their necessary conjugate bases as well as optional stabilizing salts.

68. The device of claim 50, wherein the surfactant, if present, comprises one or more sodium xylene sulfonate, disodium decyl phenyl ether disulfonate, disodium oxybis [decylbenzenesulfonate].

69. The device of claim 49, wherein the colorant is selected from indigo carmine, Acid Blue 1, Direct Blue 1, or FD&C Blue 1.

70. The device of claim 49, wherein the corrosion inhibitor is sodium carbonate.

\* \* \* \* \*